US008129532B2

(12) United States Patent
Loew et al.

(10) Patent No.: US 8,129,532 B2
(45) Date of Patent: Mar. 6, 2012

(54) AMINO(OLIGO)THIOPHENE DYES, PREPARATION THEREOF, AND OPTICAL METHODS OF USE

(75) Inventors: Leslie M. Loew, West Hartford, CT (US); Ping Yan, Middletown, CT (US)

(73) Assignee: The University of Connecticut, Farmington, CT (US)

( * ) Notice: Subject to any disclaimer, the term of this patent is extended or adjusted under 35 U.S.C. 154(b) by 801 days.

(21) Appl. No.: 12/182,599

(22) Filed: Jul. 30, 2008

(65) Prior Publication Data

US 2009/0042227 A1 Feb. 12, 2009

Related U.S. Application Data

(60) Provisional application No. 60/953,733, filed on Aug. 3, 2007.

(51) Int. Cl.
    C07D 221/06    (2006.01)
    C07D 215/12    (2006.01)
    C07D 401/00    (2006.01)
    C07D 409/00    (2006.01)
    C07D 411/00    (2006.01)
    A61K 31/44     (2006.01)
    A61K 31/47     (2006.01)
    G01N 1/30      (2006.01)

(52) U.S. Cl. ............ 546/102; 546/176; 546/276.4; 546/281.1; 546/281.4; 514/297; 514/314; 514/336; 514/337; 514/340; 435/40.5

(58) Field of Classification Search .......... 435/11, 435/29; 436/86
    See application file for complete search history.

(56) References Cited

U.S. PATENT DOCUMENTS

| 5,605,732 | A | * | 2/1997  | Mihara et al. ............... 428/64.8 |
| 5,837,783 | A | * | 11/1998 | Arnold et al. ............... 525/471 |
| 2004/0118681 | A1 | * | 6/2004 | Hellinga et al. ......... 204/403.01 |

OTHER PUBLICATIONS

Liakatas, I et al. Stilbazolium-based zwitterionic chromophores for electrooptical polymers. Ferroelectrics. 1997, vol. 202, p. 299-306.*
Salama, G et al. Properties of New, Long-Wavelength, Voltage-sensitive Dyes in the Heart. J. Membrane Biol. 2005, vol. 208, p. 125-140.*
Zhou, WL et al. Intracellular long-wavelength voltage-sensitive dyes for studying the dynamics of action potential in axons and thin dendrites. Journal of Neuroscience Methods. May 8, 2007, vol. 164, pp. 225-239.*
L.B. Cohen et al., "Changes in axon fluorescence during activity: molecular probes of membrane potential", J. Membr. Biol. 19, 1-36 (1974), Abstract, 2 pages.
I. Tasaki, "Energy transduction in the nerve membrane and studies of excitation processes with extrinsic fluorescence probes", Ann. N.Y. Acad. Sci. 227, 247-267 (1974), Abstract, 1 page.
R. Araya et al., "The spine neck filters membrane potentials", PNAS. 103, 17961-17966 (2006).
I. Ben-Oren et al., "Infrared nonlinear optical measurements of membrane potential in photoreceptor cells", Biophys. J. 71, 1616-1620 (1996), Abstract, 1 page.
O. Bouevitch et al., "Probing membrane potential with non-linear optics", Biophys. J. 77, 3341-3349 (1999), Abstract, 1 page.
D.A. Dombeck et al., "Optical recording of fast neuronal membrane potential transients in acute mammalian brain slices by second-harmonic generation microscopy", J. Neurophysiol. 94, 3628-3636 (2005), Abstract, 1 page.
A.C. Millard et al., "Direct measurement of the voltage sensitivity of second-harmonic generation from a membrane dye in patch-clamped cells", Opt. Lett. 28, 1221-1223 (2003).
A.C. Millard et al., "Sensitivity of second harmonic generation from styryl dyes to trans-membrane potential", Biophys. J. 86, 1169-1176 (2004), Abstract, 1 page.
A.C. Millard et al., "Wavelength- and Time-Dependence of Potentiometric Non-linear Optical Signals from Styryl Dyes", J. Membr. Biol. 208, 103-111 (2005), Abstract, 2 pages.
M. Nuriya et al., "Imaging membrane potential in dendritic spines", PNAS 103, 786-790 (2006), Abstract, 1 page.
P. Yan et al., "Unique Contrast Patterns from Resonance-Enhanced Chiral SHG of Cell Membranes", J. Am. Chem. Soc. 128, 11030-11031 (2006), Abstract, 1 page.
A.C. Millard et al., "Second Harmonic Imaging Microscopy", Meth. Enzymol. 361, 47-69 (2003).
T.Z. Teisseyre et al., Non-linear Optical Potentiometric Dyes Optimized for Imaging with 1064 nm Light, Journal of Biomedical Optics, vol. 12, 044001 (2007), Abstract, 1 page.
A.C. Millard et al., "Second Harmonic Generation Imaging Microscopy with a High Power Ultrafast Fiber Laser", Commercial and Biomedical Applications of Ultrafast Lasers, 5714-5716, 92-98 (2005), Abstract, 1 page.
M. Mladenova et al., Tetrahedron Lett 1999, 40, 6923-6926, Abstract, 2 pages.
L. Jin et al., "Characterization and Application of a New Optical Probe for Membrane Lipid Domains", Biophysical Journal 2006, 90, 2563-2575, Abstract, 1 page.
A.C. Millard et al., "Second Harmonic Imaging of Exocytosis at Fertilization", Biophysical Journal: Biophysical Letters 2005, 88, L46-L48, Abstract, 1 page.
R.M. De Lorimier et al., "Construction of a fluorescent biosensor family", Protein Science 2002, 11, 2655-2675, Abstract, 1 page.
D. Prim et al., Synlett, 1998, 383-384.
Zhikuan Lu and Robert J. Twieg, Tetrahedron, vol. 61, Issue 4, Jan. 2005, 903-918, Abstract, 2 pages.
H. Zhang et al., J. Org. Chem., 70, 2005, 5164-5173, Abstract, 1 page.
M. Adamczyk et al., J. Org. Chem. 1998, 63, 5636.
L. Moreaux et al., "Coherent Scattering in Multi-Harmonic Light Microscopy", Biophys. J. 80, 1568-1574 (2001), Abstract, 1 page.
L. Moreaux et al., "Membrane Imaging by Second Harmonic Generation Microscopy", J. Opt. Soc. Am. B. 17, 1685-1694 (2000), Abstract, 2 pages.

(Continued)

*Primary Examiner* — Rita Desai
*Assistant Examiner* — Ben S Michelson
(74) *Attorney, Agent, or Firm* — Cantor Colburn LLP

(57) ABSTRACT

Amino(oligo)thiophene dyes useful for studying the electrophysiology of organelles, cells, and tissues are described. Compared to previously known dyes, the amino(oligo)thiophene dyes exhibit improved (faster) response to membrane potential changes, as well as the ability to be excited by 1064 nanometer femtosecond pulses. Methods of preparing the amino( oligo )thiophene dyes are also described.

16 Claims, 24 Drawing Sheets

OTHER PUBLICATIONS

L.M. Loew, "How to choose a potentiometric membrane probe", in "Spectroscopic Membrane Probes", L.M. Loew, Ed., pp. 139-152, CRC Press, Boca Raton (1988).

A. Hassner et al., "Charge Shift Probes of Membrane Potential Synthesis", J. Org. Chem. 49, 2546-2551 (1984).

S.D. Antic et al., "Voltage-sensitive Dyes for Intracellular Application", Biol. Bull. 183, 350-351 (1992).

J.P. Wuskell et al., "Synthesis, spectra, delivery and potentiometric responses of new styryl dyes with extended spectral ranges", J. Neurosci. Methods, 151, 200-215 (2006), Abstract, 2 pages.

S.D. Antic, "Action potentials in basal and oblique dendrites of rat neocortical pyramidal neurons", Journal of Physiology, 550, 35-50 (2003), Abstract, 1 page.

S. Antic et al., "Fast optical recordings of membrane potential changes from dendrites of pyramidal neurons", Journal of Neurophysiology 82, 1615-1621 (1999), Abstract, 1 page.

W.N. Ross et al., "Species-Specific Effects on the Optical Signals of Voltage-Sensitive Syes", Journal of Membrane Biology, 48, 343-356 (1979), Abstract, 2 pages.

L.B. Cohen et al., "Optical monitoring of membrane potential: methods of multisite optical measurement", Society of General Physiologists, Series 40, 71-99 (1986).

V. Montana et al., "Dual-wavelength ratiometric fluorescence measurements of membrane potential", Biochemistry, 28, 4536-4539 (1989).

E. Fluhler et al., "Spectra, membrane binding, and potentiometric responses of new charge shift probes", Biochemistry, 24 5749-5755 (1985).

A. Bullen and P. Saggau, "High-speed, random-access fluorescence microscopy: II. Fast quantitative measurements with voltage-sensitive dyes", Biophysical Journal 76, 2272-2287, Abstract, 1 page, (1999).

H. Markram et al., "Dendritic calcium transients evoked by single back-propagating action potentials in rat neocortical pyramidal neurons", Journal of Physiology, 485, 1-20 (1995).

L.B. Cohen et al., "Changes in axon fluorescence", Biological Bulletin, 141, 382-383 (1971).

B.M. Salzberg et al., "Optical recording of neuronal activity in an invertebrate central nervous system: simultaneous monitoring of several neurons", Journal of Neurophysiology, 40, 1281-1291 (1977).

M. Djurisic et al., "Voltage imaging from dendrites of mitral cells: EPSP attenuation and spike trigger zones", J. Neurosci. 24, 6703-6714 (2004), Abstract, 1 page.

M. Zochowski et al., "Imaging membrane potential with voltage-sensitive dyes", Biological Bulletin, 198, 1-21 (2000), Abstract, 1 page.

M.E. Larkum et al., "Dendritic mechanisms underlying the coupling of the dendritic with the axonal action potential initiation zone of adult rat layer 5 pyramidal neurons", Journal of Physiology, 533, 447-466 (2001), Abstract, 1 page.

B.M. Kampa and G.J. Stuart, "Calcium spikes in basal dendrites of layer 5 pyramidal neurons during action potential bursts", J. Neurosci., 26, 7424-7432 (2006).

S. Antic et al., "Functional profile of the giant metacerebral neuron of Helix apersa: temporal and spatial dynamics of electrical activity in situ", Journal of Physiology 2000, 527, 55-69.

L.M. Palmer and G.J. Stuart, "Site of action potential initiation in layer 5 pyramidal neurons", J. Neurosci., 26, 1854-1863 (2006).

J.B. Feix and B. Kalyanaraman, "Production of singlet oxygen-derived hydroxyl radical adducts during merocyanine-540-mediated photosensitization: analysis by ESR-spin trapping and HPLC with electrochemical detection", Archives of Biochemistry & Biophysics, vol. 291, pp. 43-51 (1991).

G. Salama et al., "Properties of New, Long-Wavelength, Voltage-sensitive Dyes in the Heart", Journal of Membrane Biology, 2005, 208, 125, Abstract, 2 pages.

Ping Yan et al., "Amino(oligo)thiophene-Based Environmentally Sensitive Biomembrane Chromophores", Journal of Organic Chemistry, published on web Jul. 30, 2008, 8 pages.

Wen-Liang Zhou et al., Intracellular long-wavelength voltage-sensitive dyes for studying the dynamics of action potentials in axons and thin dendrites, Journal of Neuroscience Methods, vol. 164, Issue 2, Aug. 2007, Abstract, 2 pages.

Patrick et al., "Enhanced aqueous solubility of long wavelength voltage-sensitive dyes by covalent attachment of polyethylene glycol", Organic & Biomolecular Chemistry 5, 2007, pp. 3347-3353.

* cited by examiner

FIG. 2A
FIG. 2B
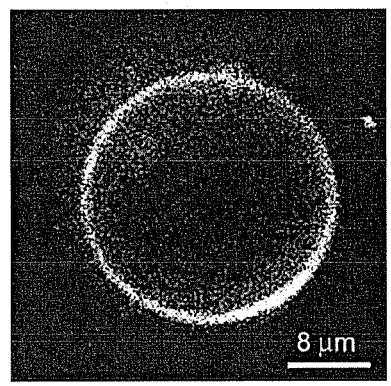 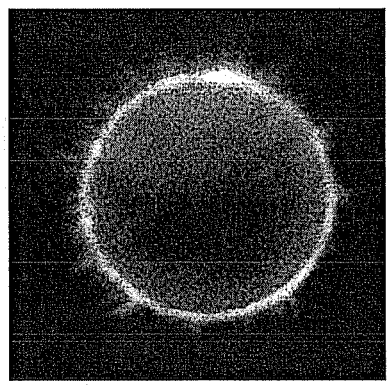
FIG. 2C
FIG. 2D
FIG. 2E
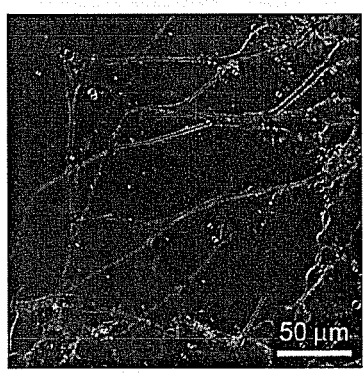 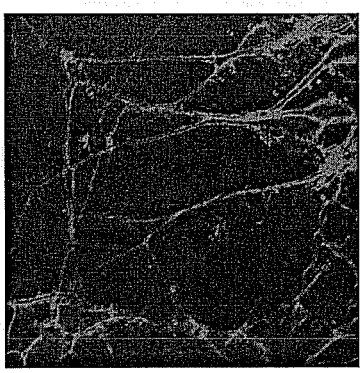 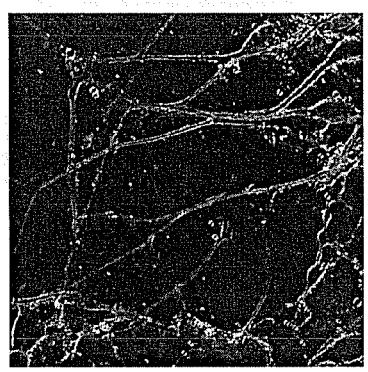
FIG. 2F
FIG. 2G
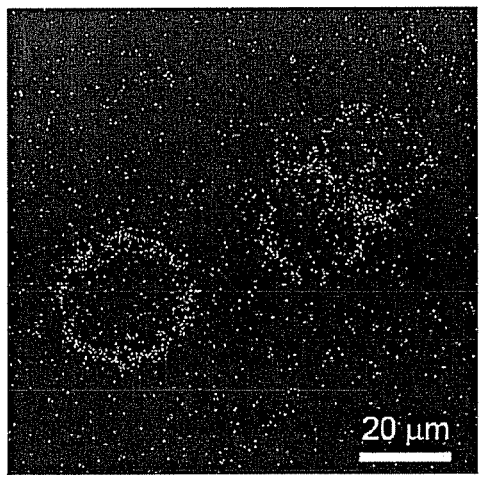 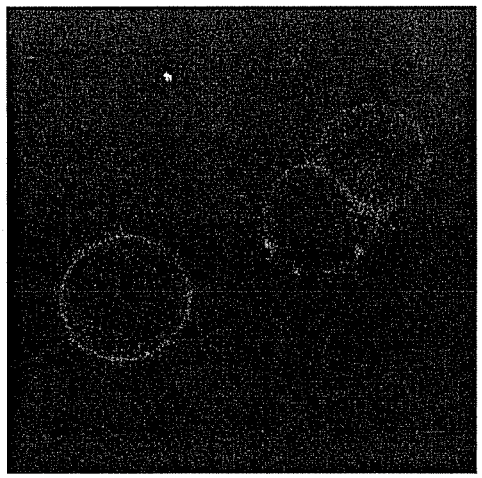

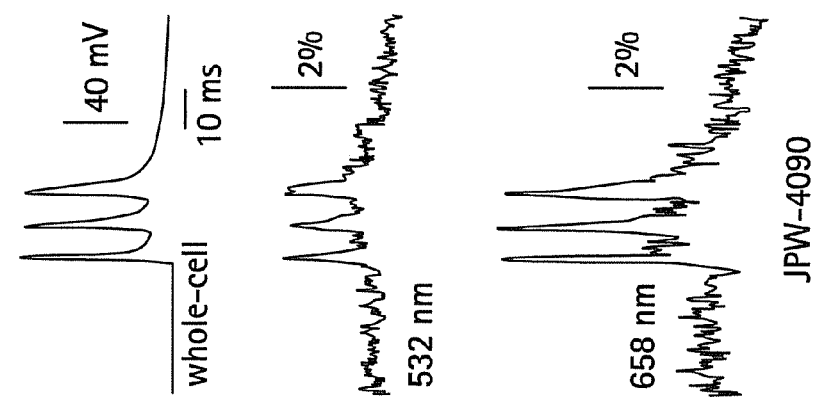
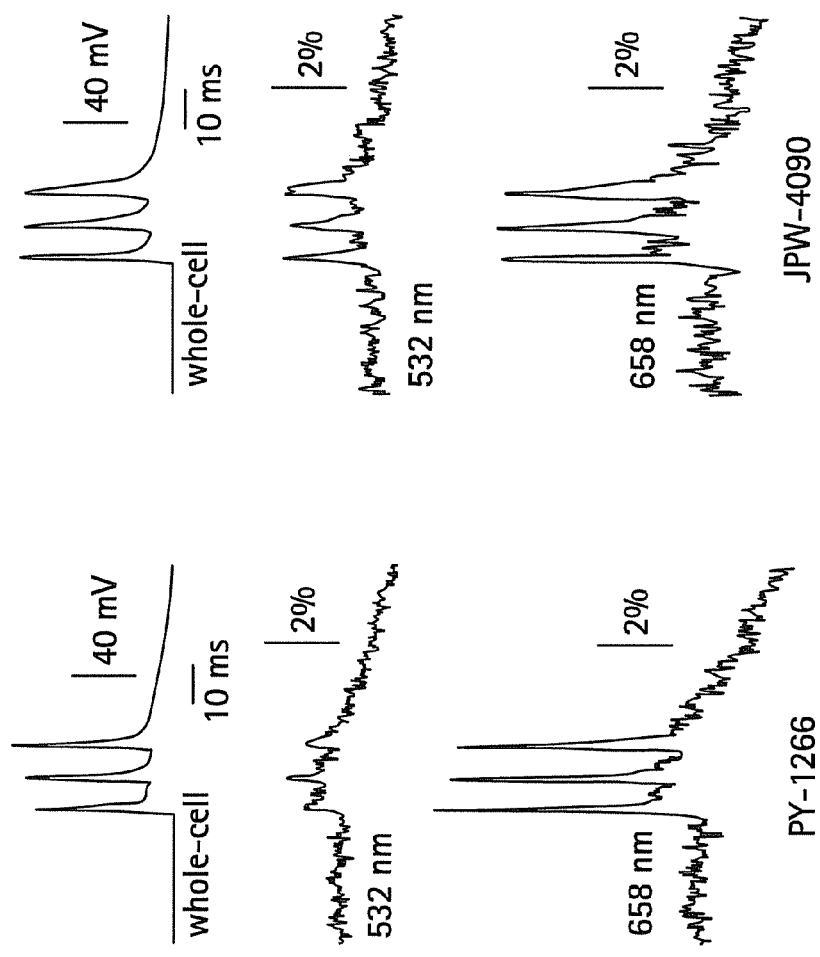
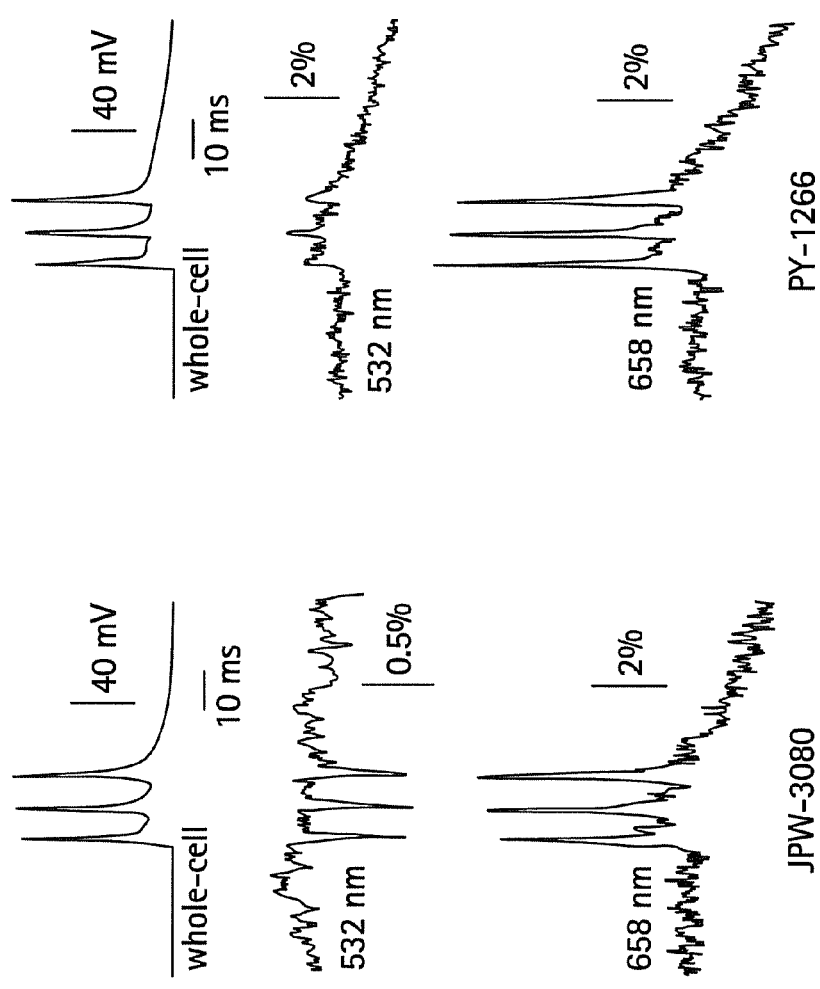

Spectral shift for JPW-3080

Spectral shift for JPW-4090

JPW-4090

JPW-4090

JPW-4090

JPW-3028 electrical

JPW-3028 optical

JPW-3028 scaled

FIG. 12A
FIG. 12B
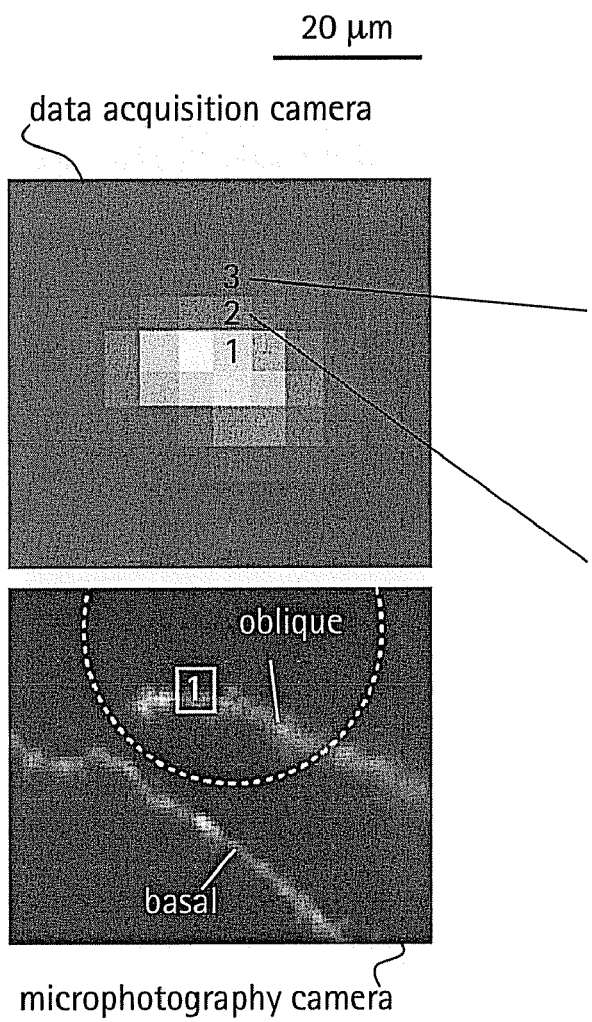
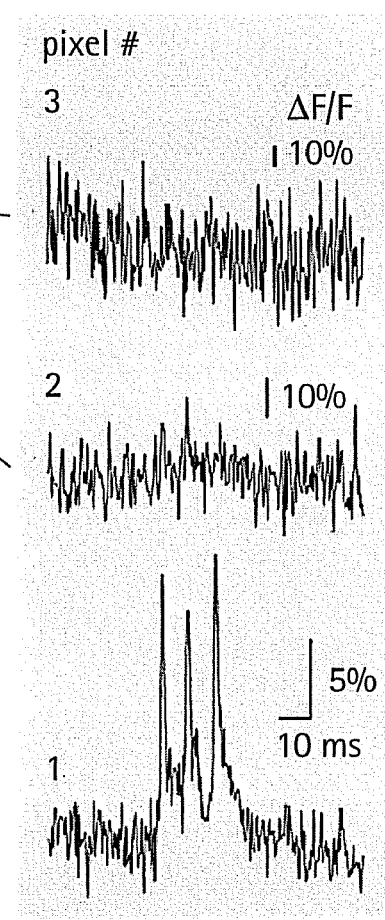

FIG. 13A
FIG. 13B
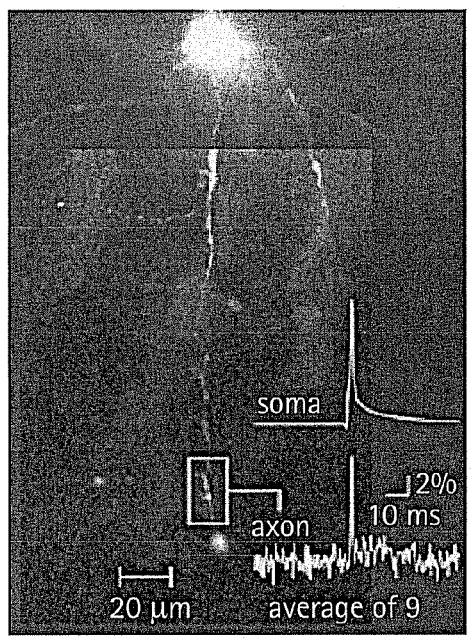
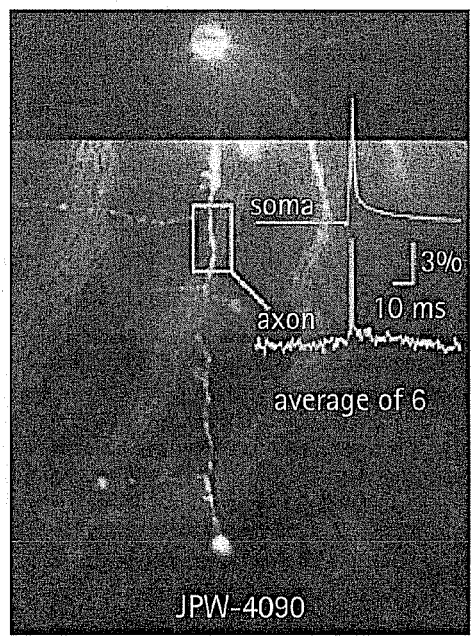

Optical recording session

JPW-3028

JPW-3028

AMINO(OLIGO)THIOPHENE DYES, PREPARATION THEREOF, AND OPTICAL METHODS OF USE

CROSS REFERENCE TO RELATED APPLICATION

This application claims the benefit of U.S. Provisional Patent Application Ser. No. 60/953,733 filed Aug. 3, 2007, which is fully incorporated herein by reference.

STATEMENT REGARDING FEDERALLY SPONSORED RESEARCH & DEVELOPMENT

This invention was made with government support under Grant Nos. U54RR022232 and EB001963 awarded by the National Institutes of Health. The government has certain rights in the invention.

BACKGROUND OF THE INVENTION

Traditional methods for monitoring electrical activity in complex systems, such as the neurons in living brains, use electrodes and therefore preclude the acquisition of high resolution spatiotemporal maps of activity. Even for single cells, the use of patch clamp technology, although very sensitive and capable of recording single action potentials, is invasive and does not permit recordings from very thin processes such as axons or dendritic spines. This has prompted the development of voltage-sensitive dyes (VSDs) whose optical properties change in response to membrane potential. These membrane-specific molecular probes can then be imaged with high speed cameras or laser scanning microscopes and the time-courses at multiple points within a specimen can be analyzed. Since the initial work on the squid giant axon (L. B. Cohen, B. M. Salzberg, H. V. Davila, W. N. Ross, D. Landowne, A. S. Waggoner, C. H. Wang, "Changes in axon fluorescence during activity: molecular probes of membrane potential," *J. Membr. Biol.* 19, 1-36 (1974); I. Tasaki, "Energy transduction in the nerve membrane and studies of excitation processes with extrinsic fluorescence probes," *Ann. N.Y. Acad. Sci.* 227, 247-267 (1974)), a variety of VSDs have been developed to study trans-membrane potential (TMP) primarily by linear optical measurements such as absorbance or fluorescence. These dyes can be excited with visible light and provide an effective method to image cell membranes and their physiology.

Non-linear optical phenomena are observed when a high intensity laser interacts with an optical material and are characterized by a probability that is proportional to the incident light intensity raised to a power greater than one. The use of these phenomena to detect TMP changes has been demonstrated. R. Araya, J. Jiang, K. B. Eisenthal, and R. Yuste, "The spine neck filters membrane potentials," *PNAS.* 103, 17961-17966 (2006); I. Ben-Oren, G. Peleg, A. Lewis, B. Minke, and L. M. Loew, "Infrared nonlinear optical measurements of membrane potential in photoreceptor cells," *Biophys. J.* 71, 1616-1620 (1996); O. Bouevitch, A. Lewis, I. Pinevsky, J. P. Wuskell, and L. M. Loew, "Probing membrane potential with non-linear optics." *Biophys. J.* 65, 672-679 (1993); P. J. Campagnola, M.-d. Wei, A. Lewis, and L. M. Loew, "High resolution optical imaging of live cells by second harmonic generation," *Biophys. J.* 77, 3341-3349 (1999); D. A. Dombeck, L. Sacconi, M. Blanchard-Desce, and W. W. Webb. "Optical recording of fast neuronal membrane potential transients in acute mammalian brain slices by second-harmonic generation microscopy." *J. Neurophysiol.* 94, 3628-3636 (2005); A. C. Millard, L. Jin, A. Lewis, and L. M. Loew, "Direct measurement of the voltage sensitivity of second-harmonic generation from a membrane dye in patch-clamped cells," *Opt. Lett.* 28, 1221-1223 (2003); A. C. Millard, L. Jin, M.-d. Wei, J. P. Wuskell, A. Lewis, and L. M. Loew, "Sensitivity of second harmonic generation from styryl dyes to trans-membrane potential," *Biophys. J.* 86, 1169-1176 (2004); A. C. Millard, L. Jin, J. P. Wuskell, D. M. Boudreau, A. Lewis, and L. M. Loew, "Wavelength- and Time-Dependence of Potentiometric Non-linear Optical Signals from Styryl Dyes," *J. Membr. Biol.* 208, 103-111 (2005); M. Nuriya, J. Jiang, B. Nemet, K. B. Eisenthal, and R. Yuste, "Imaging membrane potential in dendritic spines," *PNAS* 103, 786-790 (2006).

Second harmonic generation (SHG) and two-photon excitation fluorescence (2PF) are both non-linear optical processes taking place in proportion to the square of the incident light intensity. 2PF is the non-linear form of one-photon excitation fluorescence and operates on a similar principle. In 2PF, two photons excite a fluorophore into a state corresponding to twice their individual energies; the fluorophore then relaxes to the lowest energy electronic excited state before emitting a fluorescent photon. The emission spectrum for this non-linear process is the same as in one-photon excitation. In contrast, SHG occurs instantaneously, when two photons are converted into one of twice the energy. SHG does not involve an excited state and therefore conserves energy; the harmonic photon is emitted coherently. There are several other interrelated differences between the two methods. The first is based on the order of the term that generates each optical phenomenon. The polarization of an optical material in the presence of a high intensity electric field is a power series with coefficients associated with the material's higher order electric susceptibilities. 2PF comes from the imaginary portion of the third-order term, depending linearly on the concentration of chromophore. SHG comes from the second-order term, depending quadratically on the concentration of the SHG-active chromophores, or "harmonophores". Also, SHG is confined to loci lacking a center of symmetry, as provided, for example, by a cell membrane leaflet. P. Yan, A. C. Millard, M. Wei, and L. M. Loew, "Unique Contrast Patterns from Resonance-Enhanced Chiral SHG of Cell Membranes," *J. Am. Chem. Soc.* 128, 11030-11031 (2006). 2PF does not have this symmetry constraint.

The chromophore used to generate both non-linear phenomena can be synthesized in several forms. Previous work has shown that some aminonaphthylethenylpyridinium-based dyes ("ANEP-based dyes"; FIG. 1A-C) can exhibit a relative signal change of 43% per 100 mV for SHG signals. A. C. Millard, P. J. Campagnola, W. Mohler, A. Lewis, and L. M. Loew, "Second Harmonic Imaging Microscopy," *Meth. Enzymol.* 361, 47-69 (2003). It was also shown that SHG and 2PF signal sensitivity are wavelength dependent and scale linearly with applied voltage change. A. C. Millard, L. Jin, J. P. Wuskell, D. M. Boudreau, A. Lewis, and L. M. Loew, "Wavelength- and Time-Dependence of Potentiometric Non-linear Optical Signals from Styryl Dyes," *J. Membr. Biol.* 208, 103-111 (2005). However, the kinetics of some previous dyes were too slow to follow action potentials. The hydrophobic tail of the dye, which is characteristic of the chromophore, and the head can, however, be tailored to optimize the relative signal change and its speed. Indeed, FM4-64 (FIG. 1D), a dye that provides SHG responses to membrane potential fast enough to follow action potentials, has a similar styryl chromophore with ethyl groups attached to both the amino tail and the quaternary ammonium head. D. A. Dombeck, L. Sacconi, M. Blanchard-Desce, and W. W. Webb. "Optical recording of fast neuronal membrane potential transients in acute mammalian brain slices by second-harmonic generation microscopy."*J Neurophysiol.* 94, 3628-3636 (2005); M. Nuriya, J. Jiang, B. Nemet, K. B. Eisenthal, and R. Yuste, "Imaging membrane potential in dendritic spines," *PNAS* 103, 786-790 (2006). However, FM4-64 has a relatively small sensitivity to membrane potential of only 7.5-10% per 100 mV.

There remains a need for dyes with improved (faster) response to membrane potential for SHG and 2PF, as well as the ability to be excited by 1064 nanometer femtosecond pulses. There is also a need for dyes for use in studying the dynamics of action potentials in axons and dendrites and the compositions of lipid membranes.

BRIEF DESCRIPTION OF THE INVENTION

The above-described and other drawbacks are alleviated by an amino(oligo)thiophene dye having the structure

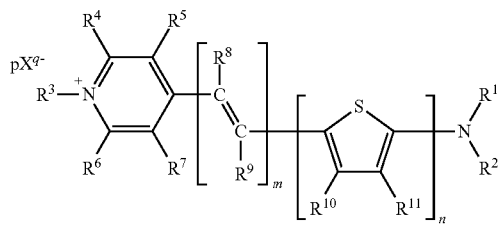

wherein m is 1, 2, 3, or 4; n is 1, 2, 3, 4, 5, or 6; $R^1$ and $R^2$ are each independently hydrogen or optionally substituted $C_1$-$C_{10}$ alkyl, $C_3$-$C_7$ cycloalkyl, or phenyl; $R^3$ is optionally substituted $C_1$-$C_{10}$ alkyl; $R^4$, $R^5$, $R^6$, and $R^7$ are each independently hydrogen or fluorine; or $R^4$ and $R^5$ collectively form a fused aromatic ring, and/or $R^6$ and $R^7$ collectively form a fused aromatic ring; each occurrence of $R^8$, $R^9$, $R^{10}$, and $R^{11}$ is independently hydrogen or halogen, or $R^{10}$ and $R^{11}$ collectively form ethylenedioxy (—OCH$_2$CH$_2$O—); provided that when n is 2, 3, 4, 5, or 6, at least two adjacent thiophene groups can, optionally, be linked via a fused ring to form a dithiophene unit having the structure

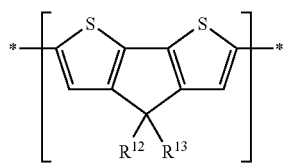

wherein $R^{12}$ and $R^{13}$ are each independently hydrogen or optionally substituted $C_1$-$C_6$ alkyl; $X^{q-}$ is an anionic counterion wherein q is 1 or 2 or 3; and p is 0, 1, 2, 3, or 4.

Another embodiment is an amino(oligo)thiophene dye having the structure

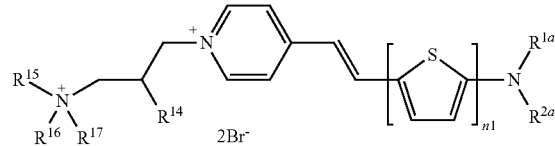

herein $R^{1a}$ and $R^{2a}$ are each independently $C_1$-$C_6$ alkyl; $R^{14}$ is hydrogen or hydroxy; $R^{15}$, $R^{16}$, and $R^{17}$ are each independently methyl, ethyl, or 2-hydroxyethyl; and n1 is 1, 2, or 3.

Another embodiment is an amino(oligo)thiophene dye having a structure selected from the group consisting of

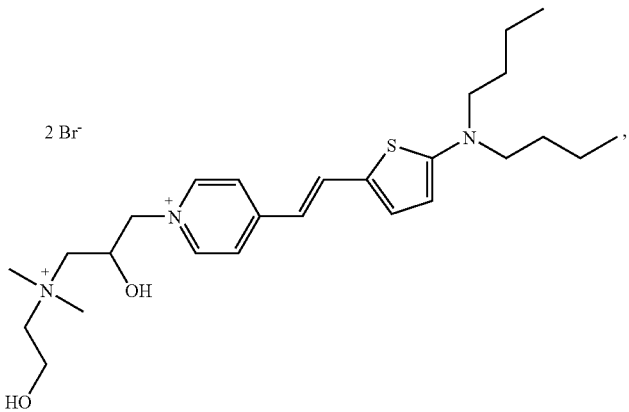

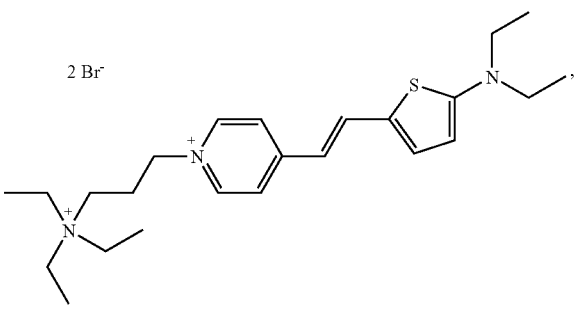

-continued
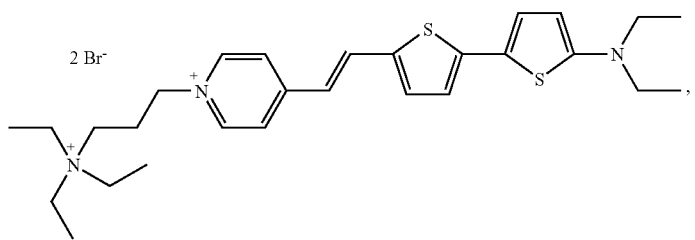
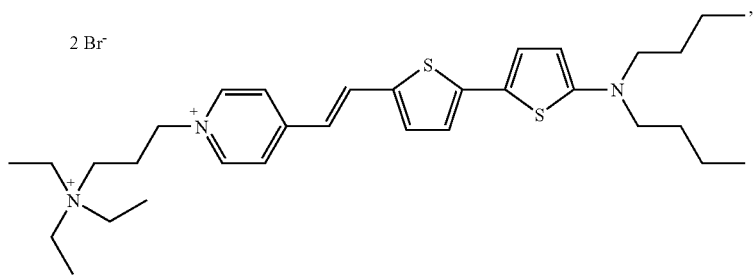
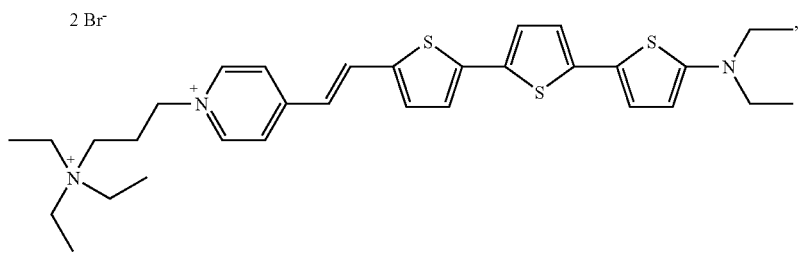
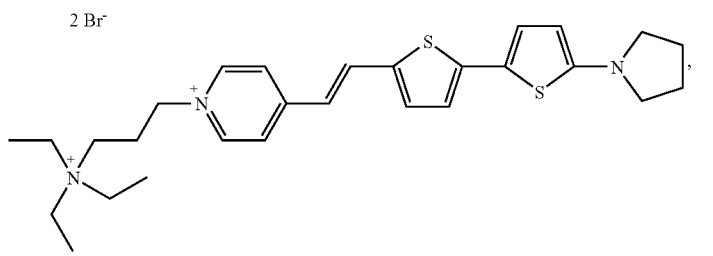
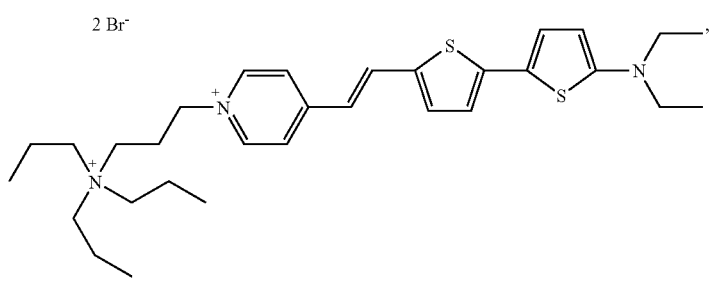
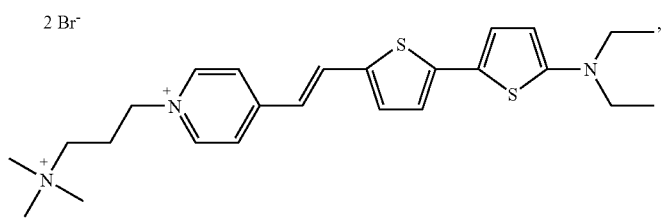

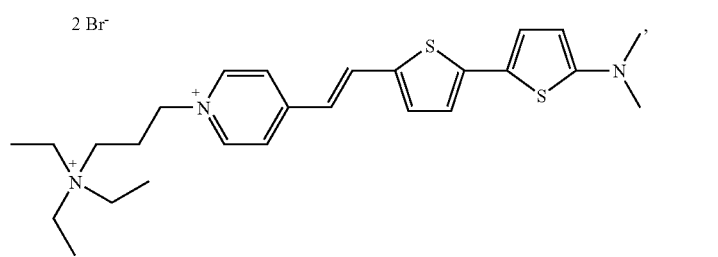
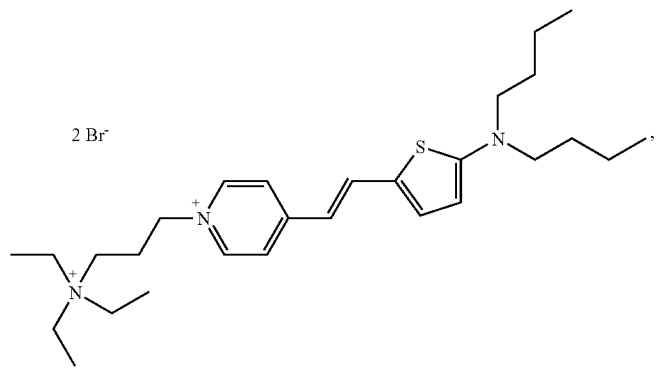
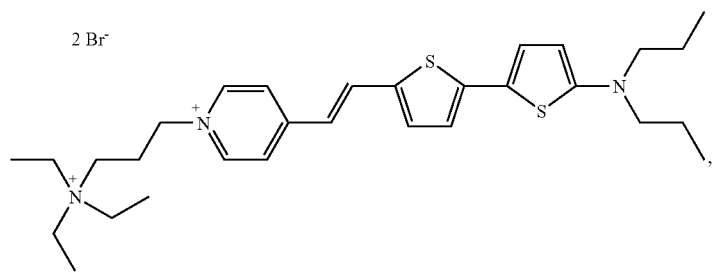
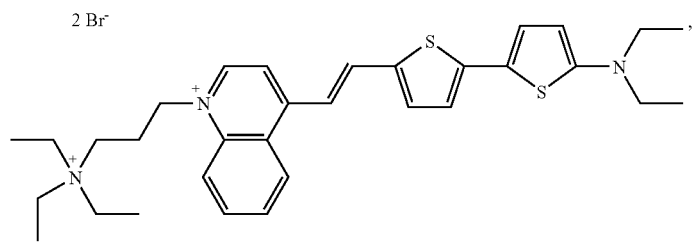
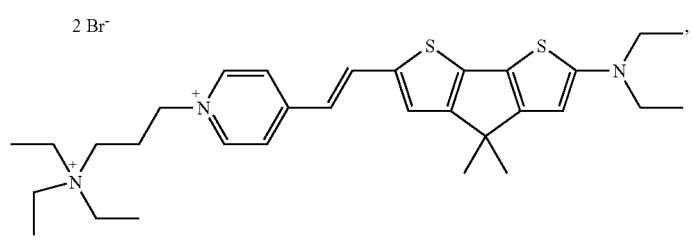
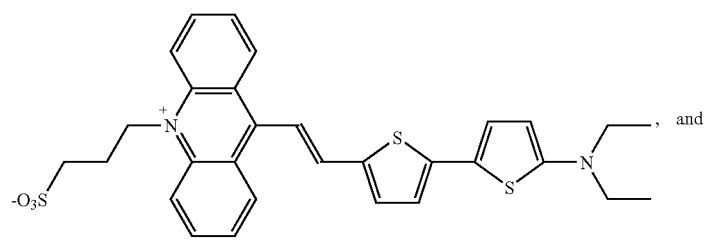

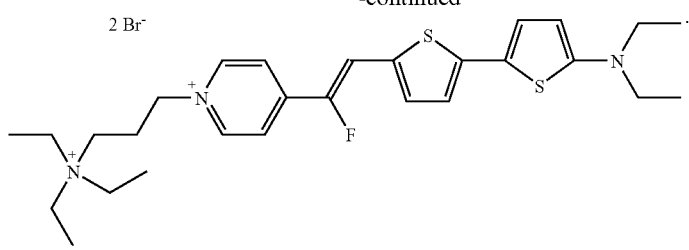

Another embodiment is a method of preparing an amino(oligo)thiophene dye, comprising: reacting an amine with a bromine-substituted (oligo)thiophene to form an amino-substituted (oligo)thiophene; and reacting the amino-substituted (oligo)thiophene with a 4-methyl-N-alkyl-pyridinium salt to form the amino(oligo)thiophene dye; wherein the amine has the structure $HN(R^1)(R^2)$, wherein $R^1$ and $R^2$ are each independently hydrogen or optionally substituted $C_1$-$C_{10}$ alkyl, $C_3$-$C_7$ cycloalkyl, or phenyl; wherein the bromine-substituted (oligo)thiophene has the structure

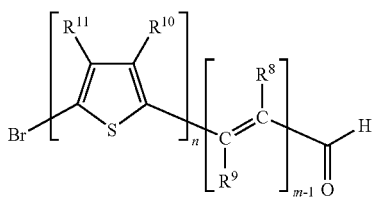

wherein m is 1, 2, 3, or 4; n is 1, 2, 3, 4, 5, or 6; each occurrence of $R^8$, $R^9$, $R^{10}$, and $R^{11}$ is independently hydrogen or halogen, or $R^{10}$ and $R^{11}$ collectively form ethylenedioxy (—$OCH_2CH_2O$—); provided that when n is 2, 3, 4, 5, or 6, at least two adjacent thiophene groups can, optionally, be linked via a fused ring to form a dithiophene unit having the structure

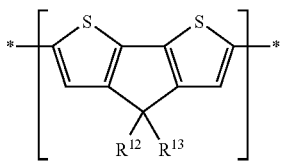

wherein $R^{12}$ and $R^{13}$ are each independently hydrogen or optionally substituted $C_1$-$C_6$ alkyl; wherein the amino-substituted (oligo)thiophene has the structure

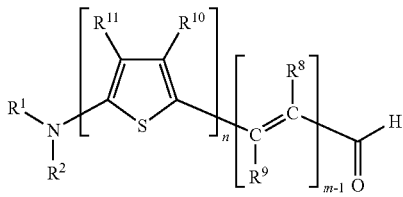

wherein $R^1$, $R^2$, $R^8$, $R^9$, $R^{10}$, $R^{11}$, m, and n are as defined above; and wherein the 4-methyl-N-alkyl-pyridinium salt has the structure

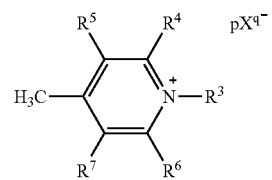

wherein $R^3$ is optionally substituted $C_1$-$C_{10}$ alkyl; $R^4$, $R^5$, $R^6$, and $R^7$ are each independently hydrogen or fluorine; or $R^4$ and $R^5$ collectively form a fused aromatic ring, and/or $R^6$ and $R^7$ collectively form a fused aromatic ring; $X^{q-}$ is an anionic counterion wherein q is 1 or 2 or 3; and p is 0, 1, 2, 3, or 4; and wherein the amino(oligo)thiophene dye has the structure

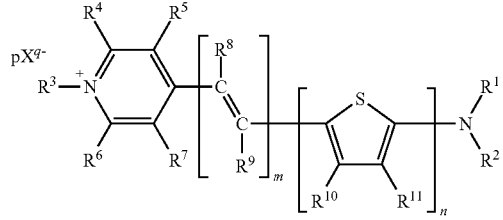

wherein $R^1$-$R^{11}$, X, m, n, p, and q are as defined above.

Another embodiment is a method utilizing one or more of the amino(oligo)thiophene dyes for the optical assessment, monitoring, and/or evaluation of electrophysiology of organelles, cells, or tissues.

Another embodiment is a clinical diagnostic method utilizing one or more of the amino(oligo)thiophene dyes for the optical assessment, monitoring, and/or evaluation of the electrophysiological state of organelles, cells, or tissues of a human or non-human mammalian subject of interest.

Another embodiment is a method utilizing one or more of the amino(oligo)thiophene dyes for the optical assessment, monitoring, and/or evaluation of the composition and/or structure of a lipid membrane.

Another embodiment is a method utilizing a conjugate of a protein and one or more of the amino(oligo)thiophene dyes for the optical assessment, monitoring, and/or evaluation of protein conformation; wherein the protein of the conjugate is covalently linked to one or more of the amino(oligo) thiophene dyes.

Another embodiment is a clinical diagnostic method utilizing one or more of the amino(oligo)thiophene dyes for monitoring cholesterol content in a lipid membrane in organelles, cells, or tissues of a human or non-human mammalian subject of interest.

Another embodiment is a clinical diagnostic method utilizing one or more of the amino(oligo)thiophene dyes for monitoring exocytosis-induced changes in the composition and/or structure of a lipid membrane in organelles, cells, or tissues of a human or non-human mammalian subject of interest.

Another embodiment is a clinical diagnostic method utilizing one or more of the amino(oligo)thiophene dyes for optical assessment, monitoring, and/or evaluation of protein conformation in organelles, cells, or tissues of a human or non-human mammalian subject of interest.

Another embodiment is a biosensor comprising one or more of the amino(oligo)thiophene dyes and, optionally, further comprising a conjugate of a protein and one or more of the amino(oligo)thiophene dyes of claims 1-14; wherein the protein of the conjugate is covalently linked to one or more of the amino(oligo)thiophene dyes.

These and other embodiments are described in detail below.

BRIEF DESCRIPTION OF THE DRAWINGS

FIG. 2 shows two forms of non-linear optical images of stained undifferentiated and differentiated neuroblastoma cells stained with PY-1261 or PY-1284 and excited with a 1064 nm fiber laser: (a) SHG for an undifferentiated neuroblastoma cell stained with PY-1261; (b) 2PF for an undifferentiated neuroblastoma cell stained with PY-1261 (acquired in parallel with image (a)); (c) SHG for a differentiated neuroblastoma cell stained with PY-1261; (d) 2PF for a differentiated neuroblastoma cell stained with PY-1261 (acquired in parallel with image (c)); (e) merged images (c) and (d); (f) SHG for an undifferentiated neuroblastoma cell stained with PY-1284; (g) 2PF for an undifferentiated neuroblastoma cell stained with PY-1284 (acquired in parallel with image (g)).

FIG. 12 relates to light scattering: (Aa) Same as in FIG. 3B1; The tip of the oblique branch is blown up to show individual pixels; (Ab) The same structure as in Aa captured with higher resolution camera; Dotted circle indicates the position and size of the laser illumination spot. The basal branch was intentionally left outside of the bright spot; (B) Optical signals from three neighboring pixels marked by numbers in Aa; Biological signal (triplet of APs) is only present in the pixel #1, which receives direct light from oblique dendrite; Note that amplitude scales in pixels #2 and #3 are ~3 and ~5 time-blowup of the scale in the bottom trace.

DETAILED DESCRIPTION OF THE INVENTION

Figure 1A:
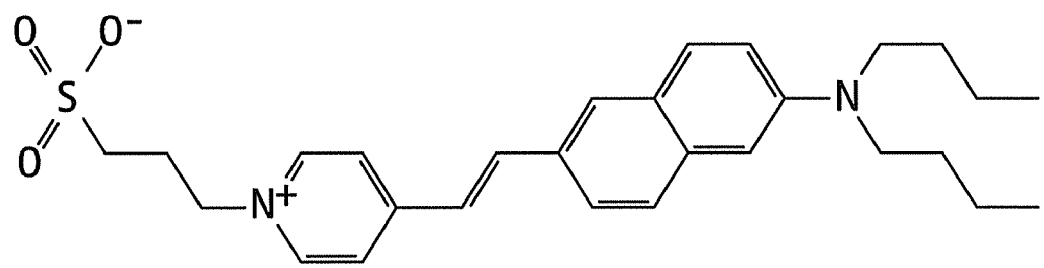
FIG. 1 shows molecular structures of dyes used in previous work: (a) di-4-ANEPPS. (b) Ebis(di-4-ANEP). (c) di-4-ANEPPDHQ. (d) FM4-64.
Figure 1B:
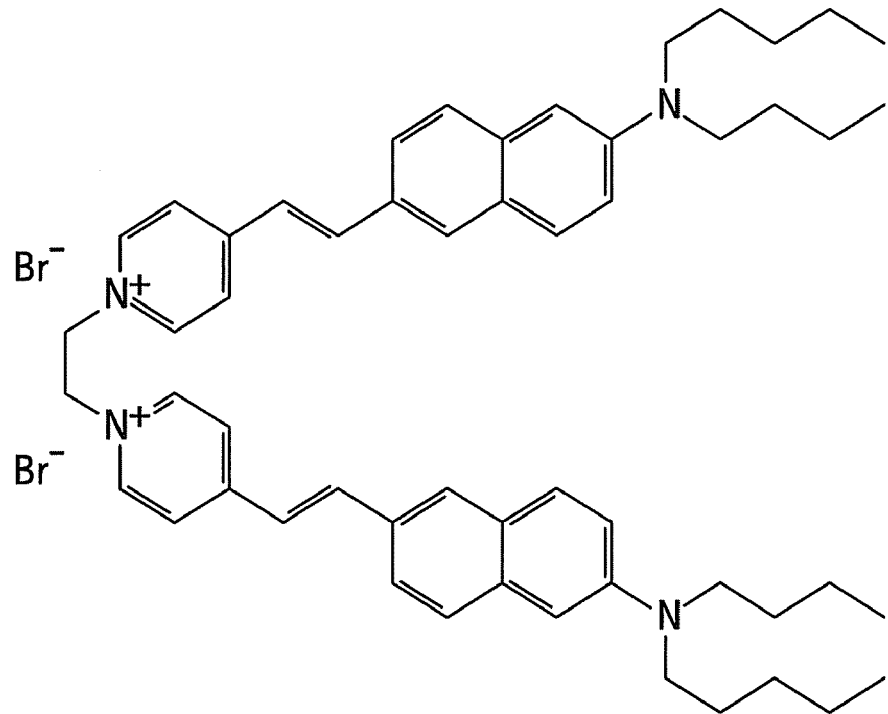
Figure 1C:
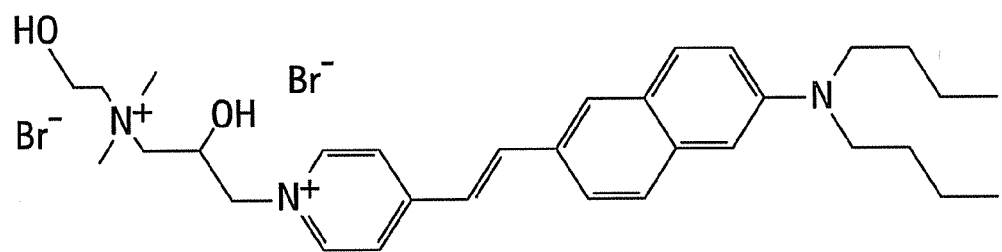

We have developed a new class of dyes with a chromophore comprising a pyridinium, quinolinium, or acridinium group, and a thiophene or oligothiophene group. The charge is oriented around the pyridinium group in the ground state and shifts during excitation. Some of these new dyes yield significantly improved fast responses to membrane potential for SHG as well as 2PF. The dyes under consideration show specific excitation by 1064 nanometer femtosecond pulses that can be generated with a relatively inexpensive and stable fiber laser. Millard, A. C., L. Jin, and L. M. Loew, "Second Harmonic Generation Imaging Microscopy with a High Power Ultrafast Fiber Laser," *Commercial and Biomedical Applications of Ultrafast Lasers.* 5714-5716, 92-98 (2005). We believe that the combination of the better dye responses and the simpler optical setup afforded by the fiber laser will allow this non-linear optical microscopy to become a more widespread tool for the neuroimaging of electrical activity.

One embodiment is an amino(oligo)thiophene dye having the structure

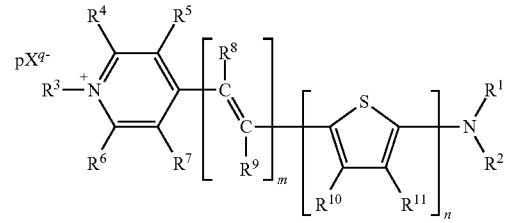

wherein m is 1, 2, 3, or 4; n is 1, 2, 3, 4, 5, or 6; $R^1$ and $R^2$ are each independently hydrogen or optionally substituted $C_1$-$C_{10}$ alkyl, $C_3$-$C_7$ cycloalkyl, or phenyl; $R^3$ is optionally substituted $C_1$-$C_{10}$ alkyl; $R^4$, $R^5$, $R^6$, and $R^7$ are each independently hydrogen or fluorine; or $R^4$ and $R^5$ collectively form a fused aromatic ring, and/or $R^6$ and $R^7$ collectively form a fused aromatic ring; each occurrence of $R^8$, $R^9$, $R^{10}$, and $R^{11}$ is independently hydrogen or halogen, or $R^{10}$ and $R^{11}$ collectively form ethylenedioxy (—$OCH_2CH_2O$—); provided that when n is 2, 3, 4, 5, or 6, at least two adjacent thiophene groups can, optionally, be linked via a fused ring to form a dithiophene unit having the structure

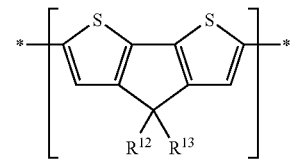

wherein $R^{12}$ and $R^{13}$ are each independently hydrogen or optionally substituted $C_1$-$C_6$ alkyl; $X^{q-}$ is an anionic counterion wherein q is 1 or 2 or 3; and p is 0, 1, 2, 3, or 4. As used herein, the term "optionally substituted" means that any unspecified group bonded to carbon can be a hydrogen atom or a substituent such as, for example, halogen (including fluorine, chlorine, bromine, or iodine), sulfonate, trialkylammonium, carboxylate, acryloyl, succinimide, maleimide, iodoacetamide, and the like. Among these, pendant acryloyl, succinimide, maleimide, and iodoacetamide groups are particularly useful for their reactions with the thiol groups of cysteine residues of proteins to form dye-protein conjugates. The fragment "(oligo)" within the term "amino(oligo)thiophene dye" means that the dye can be an aminothiophene dye (n=1) or an aminooligothiophene dye (n=2, 3, 4, 5, or 6).

When $R^4$ and $R^5$ collectively form a fused aromatic ring, a quinolinium group having the structure

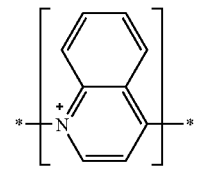

is formed. When $R^4$ and $R^5$ collectively form a fused aromatic ring, and $R^6$ and $R^7$ collectively form a fused aromatic ring, an acridinium group having the structure

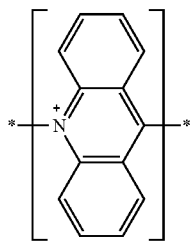

is formed. For brevity, the term "pyridinium group", but it will be understood that such usage encompasses quinolinium and acridinium groups. In some embodiments, the number of repeating ethenylene groups, m, is 1. In some embodiments, the number of repeating thiophene groups, n, is 1, 2, or 3, specifically 2 or 3. In some embodiments, the amino substituents $R^1$ and $R^2$ are each independently $C_1$-$C_4$ alkyl or $C_1$-$C_4$ perfluoroalkyl. In some embodiments, $R^3$ is a quaternary ammonium-substituted $C_1$-$C_{10}$ alkyl group or a quaternary ammonium-substituted $C_1$-$C_{10}$ perfluoroalkyl group. Suitable quaternary ammonium-substituted alkyl groups include the quaternary ammonium-substituted propyl groups having the structure

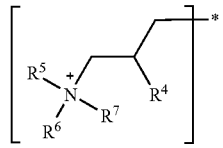

wherein $R^4$ is hydrogen or hydroxy; and $R^5$, $R^6$, and $R^7$ are each independently methyl, ethyl, or 2-hydroxyethyl. In some embodiments, $R^3$ is substituted with a sulfonate ion. Suitable sulfonate-substituted alkyl groups include the sulfonate-substituted propyl group having the structure

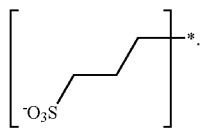

When a sulfonate group is present, its negative charge can be balanced by the positive charge of the pyridinium, quinolinium, or acridinium group; alternatively, the negative charge of the sulfonate group can be balanced by a separate cation, such as a proton (in which case the sulfonate group exists as a sulfonic acid), an alkali metal cation, or an optionally substituted ammonium ion.

The amino(oligo)thiophene dye includes one or more counterions, $X^{q-}$, to balance the positive charge(s) of the amino(oligo)thiophene cation (including any charged substituents on the amino(oligo)thiophene cation). In other words, the total negative charge, p×q, contributed by the anion(s) $pX^{q-}$, is equal to the net positive charge on the amino(oligo)thiophene-substituted cation. Suitable counterions, $X^{q-}$, include, for example, hydroxide, fluoride, chloride, bromide, and iodide, sulfite, sulfate, acetate, trifluoroacetate, propionate, succinate, glycolate, stearate, lactate, malate, tartrate, citrate, ascorbate, pamoate, maleate, hydroxymaleate, phenylacetate, glutamate, benzoate, salicylate, sulfanilate, 2-acetoxybenzoate, fumarate, toluenesulfonate, methanesulfonate, ethanesulfonate, ethane disulfonate, benzenesulfonate, toluenesulfonate, oxalate, malonate, succinate, glutarate, adipate, isethionate, and the like, and mixtures thereof. In some embodiments, $X^{q-}$ is bromide.

The amino(oligo)thiophene dyes exhibit an optical environmental sensitivity. For example, the wavelength and/or intensity of an amino(oligo)thiophene dye's fluorescence is sensitive to the molecular environment of the dye. In some embodiments, the optical environmental sensitivity is a second harmonic generation environmental sensitivity of at least 3 percent per 50 millivolts when stimulated with a 1064 nanometer femtosecond fiber laser. Specifically, this sensitivity can be at least 6 percent per 50 millivolts, more specifically at least 9 percent per 50 millivolts, even more specifically 3 to 12 percent per 50 millivolts. As another example of environmental sensitivity, in some embodiments, the optical environmental sensitivity is a two photon fluorescence environmental sensitivity of at least 3 percent per 50 millivolts at 615-665 nanometers. Specifically, this sensitivity can be at least 6 percent per 50 millivolts, even more specifically 3 to 17 percent per 50 millivolts.

In some embodiments, the amino(oligo)thiophene dye has the structure

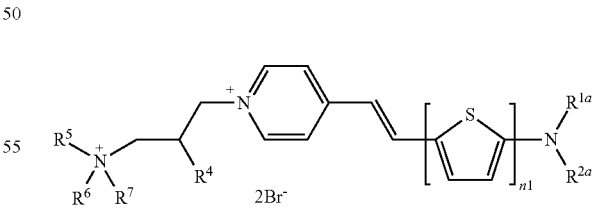

wherein $R^{1a}$ and $R^{2a}$ are each independently $C_1$-$C_6$ alkyl; $R^4$ is hydrogen or hydroxy; $R^5$, $R^6$, and $R^7$ are each independently methyl, ethyl, or 2-hydroxyethyl; and n1 is 1, 2, or 3.

Specific amino(oligo)thiophene dyes that have been synthesized and characterized include
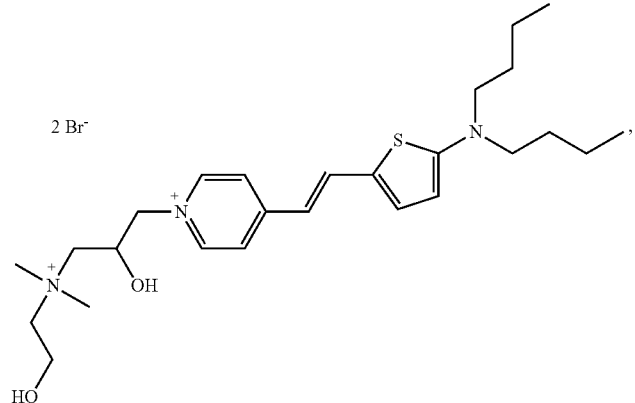
[PY-1237]
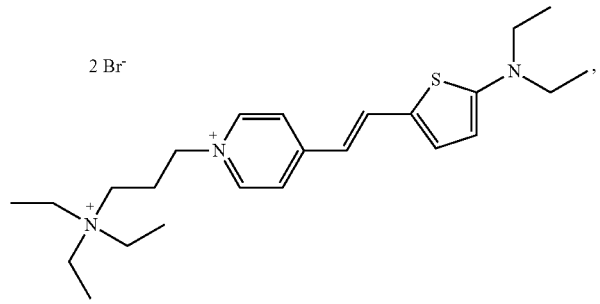
[PY-1248]
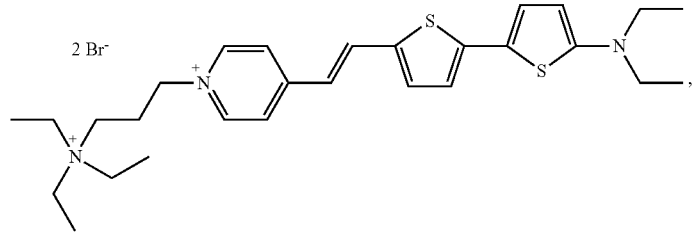
[PY-1261]
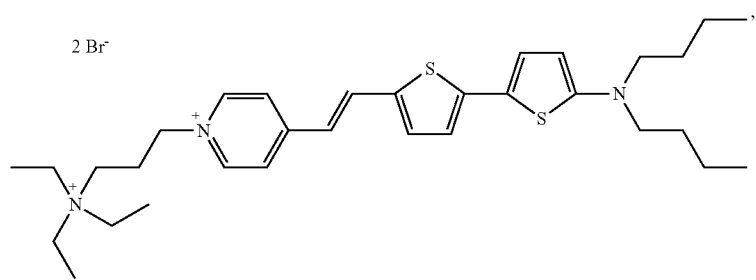
[PY-1266]
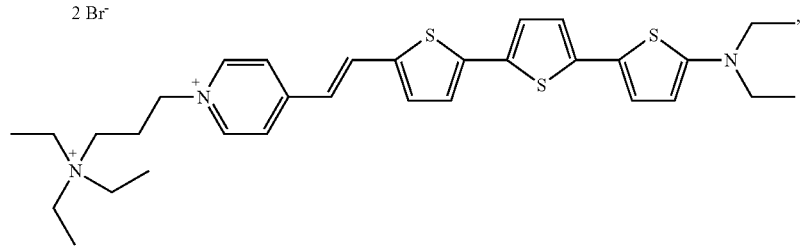
[PY-1268]

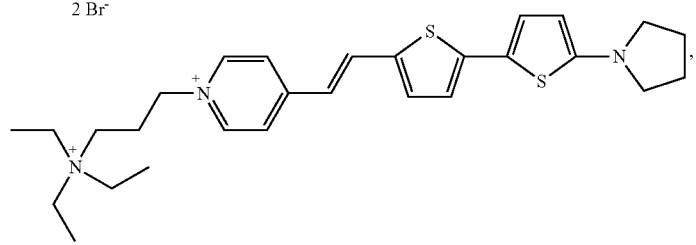
[PY-1274]
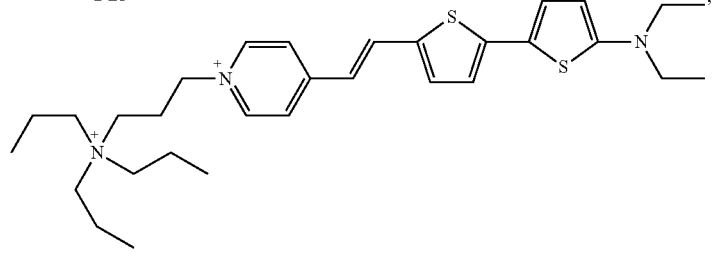
[PY-1278]
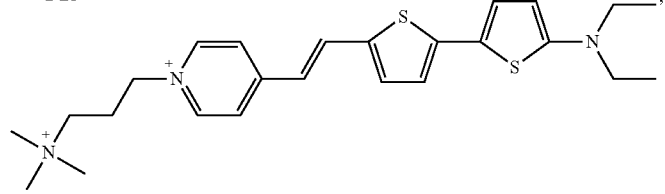
[PY-1280]
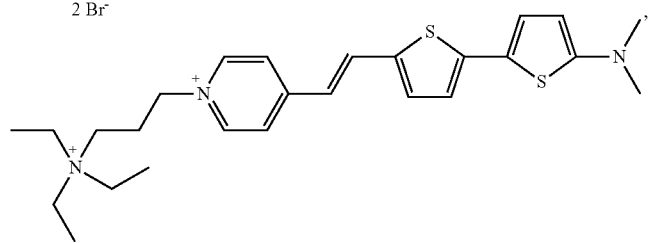
[PY-1282]
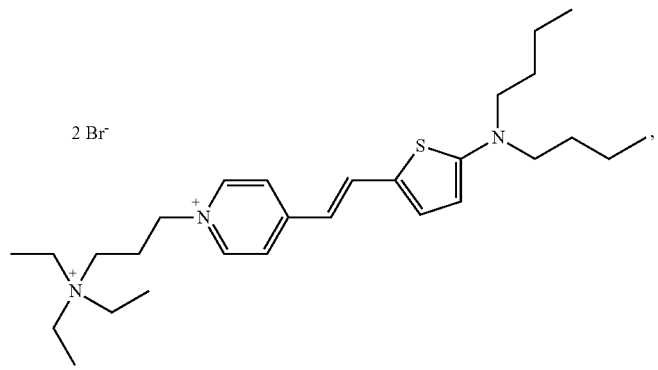
[PY-1284]

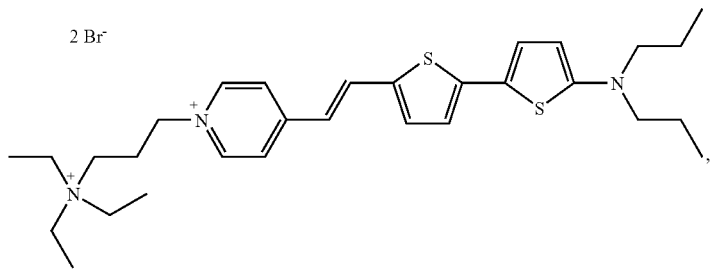
[PY-1286]

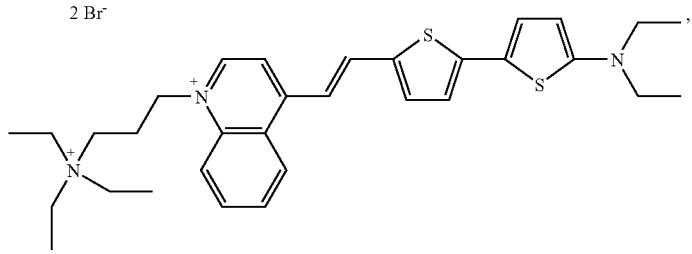
[PY-2120]

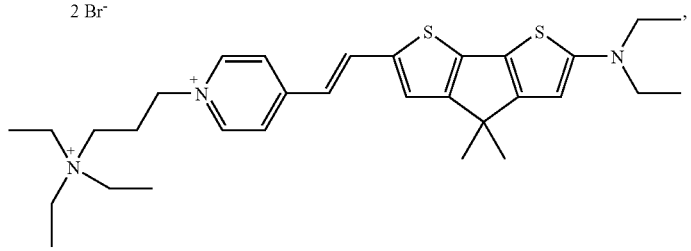
[PY-2174]

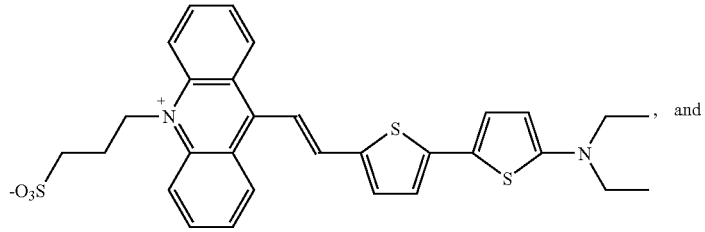
[PY-2240]

and

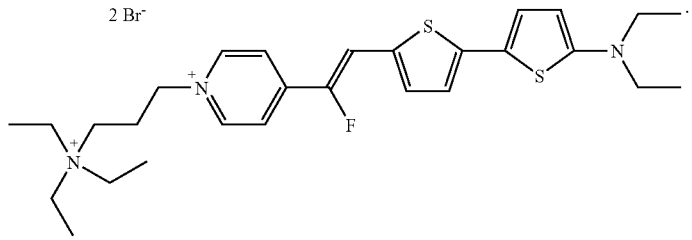
[PY-3008]

The invention includes methods of making amino(oligo) thiophene dyes. Thus, one embodiment is a method of preparing an amino(oligo)thiophene dye, comprising: reacting an amine with a bromine-substituted (oligo)thiophene to form an amino-substituted (oligo)thiophene; and reacting the amino-substituted (oligo)thiophene with a 4-methyl-N-alkyl-pyridinium salt, a 4-methyl-N-alkyl-quinolinium salt, or a 10-methyl-N-alkyl-acridinium salt to form the amino(oligo) thiophene dye; wherein the amine has the structure $HN(R^1)(R^2)$, wherein $R^1$ and $R^2$ are each independently hydrogen or optionally substituted $C_1$-$C_{10}$ alkyl, $C_3$-$C_7$ cycloalkyl, or phenyl; wherein the bromine-substituted (oligo)thiophene has the structure

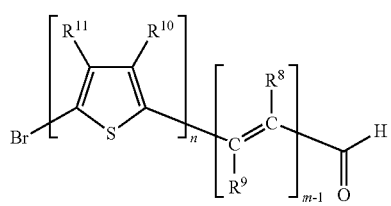

wherein m is 1, 2, 3, or 4; n is 1, 2, 3, 4, 5, or 6; each occurrence of $R^8$, $R^9$, $R^{10}$, and $R^{11}$ is independently hydrogen or halogen, or $R^{10}$ and $R^{11}$ collectively form ethylenedioxy (—OCH$_2$CH$_2$O—), provided that when n is 2, 3, 4, 5, or 6, at least two adjacent thiophene groups can, optionally, be linked via a fused ring to form a dithiophene unit having the structure

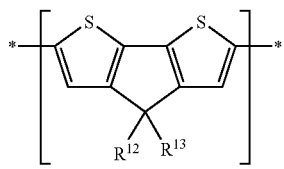

wherein R$^{12}$ and R$^{13}$ are each independently hydrogen or optionally substituted C$_1$-C$_6$ alkyl; wherein the amino-substituted (oligo)thiophene has the structure

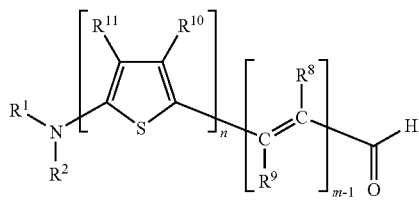

wherein R$^1$, R$^2$, R$^8$, R$^9$, R$^{10}$, R$^{11}$, m, and n are as defined above; and wherein the 4-methyl-N-alkyl-pyridinium salt has the structure

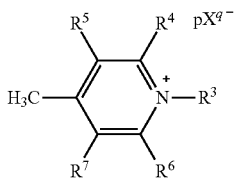

wherein R$^3$ is optionally substituted C$_1$-C$_{10}$ alkyl; R$^4$, R$^5$, R$^6$, and R$^7$ are each independently hydrogen or fluorine; or R$^4$ and R$^5$ collectively form a fused aromatic ring, and/or R$^6$ and R$^7$ collectively form a fused aromatic ring (as indicated above, when R$^4$ and R$^5$ collectively form a fused benzene ring or R$^6$ and R$^7$ collectively form a fused benzene ring, the "4-methyl-N-alkyl-pyridinium salt" is actually a 4-methyl-N-alkyl-quinolinium salt; and when R$^4$ and R$^5$ collectively form a fused benzene ring and R$^6$ and R$^7$ collectively form a fused benzene ring, the "4-methyl-N-alkyl-pyridinium salt" is actually a 10-methyl-N-alkyl-acridinium salt); X$^{q-}$ is an anionic counterion wherein q is 1 or 2 or 3; and p is 0, 1, 2, 3, or 4; and wherein the amino(oligo)thiophene dye has the structure

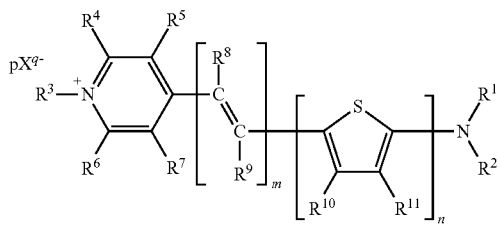

wherein R$^1$-R$^{11}$, X, m, n, p, and q are as defined above.

It will be understood that the synthetic method is capable of producing amino(oligo)thiophene dyes having more than one ethenylene group between the pyridinium moiety and the (oligo)thiophene moiety. For example, an ethenylene-containing amino-substituted (oligo)thiophene can be substituted for the amino-substituted (oligo)thiophene shown above. Methods of transforming an aldehyde group (—C(═O)H) into a —CH═CH—C(═O)H group are known in the art and described, for example, in M. Mladenova, L. Ventelon, M. Blanchard-Desce, Tetrahedron Lett 1999, 40, 6923-6926. One such method is illustrated in the reaction scheme below.

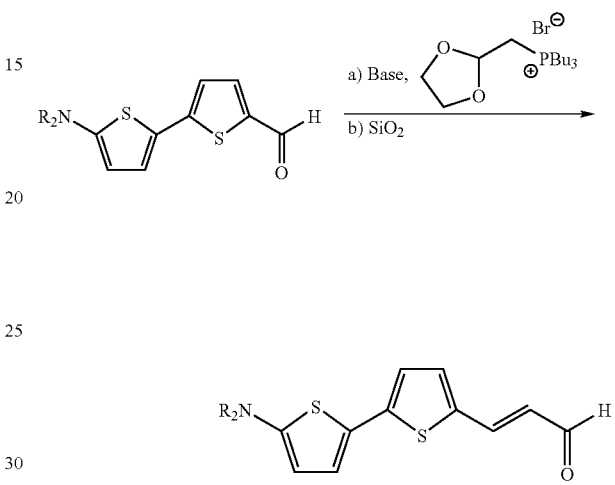

The procedure can be carried out multiple times to introduce additional ethenylene groups.

As demonstrated in the working examples below, the amino(oligo)thiophene dyes are useful in a variety of methods that utilize the environmental sensitivity of the dyes' spectroscopic properties, particularly the dyes' fluorescence properties. For example, the amino(oligo)thiophene dyes are useful for the optical assessment, monitoring, and/or evaluation of the electrophysiology of organelles, cells, or tissues of a human or non-human mammalian subject of interest. In these embodiments, the method can monitor a change in wavelength and/or intensity of a fluorescence emission from the amino(oligo)thiophene dye. In a particular embodiment, the method can monitor a change in intensity of second harmonic generation by the amino(oligo)thiophene dye. In another particular embodiment, the method can monitor a change in the wavelength and/or intensity of a fluorescence emission from two-photon excitation of the dye. The amino(oligo)thiophene dyes are also useful for monitoring the dynamics of action potentials in axons and/or dendrites.

Another example of a method that utilizes the environmental sensitivity of the amino(oligo)thiophene dyes' spectroscopic properties is a method utilizing one or more of the amino(oligo)thiophene dyes for optical assessment, monitoring, and/or evaluation of the composition and/or structure of a lipid membrane. Specifically, the amino(oligo)thiophene dyes can be used to monitor the cholesterol content of a lipid membrane. For example, the new amino(oligo)thiophene dyes can be utilized in the methods described in L. Jin, A. C. Millard, J. P. Wuskell, X. Dong, W. Dianqing, H. A. Clark, and L. M. Loew, "Characterization and Application of a New Optical Probe for Membrane Lipid Domains", Biophysical Journal 2006, 90 2563-2575.

Another example of a method that utilizes the environmental sensitivity of the amino(oligo)thiophene dyes' spectroscopic properties is a method utilizing one or more of the amino(oligo)thiophene dyes for optical assessment, monitoring, and/or evaluation of exocytosis. For example, the new amino(oligo)thiophene dyes can be utilized in the methods described in A. C. Millard, M. Terasaki, L. M. Loew, "Second Harmonic Imaging of Exocytosis at Fertilization", *Biophysical Journal: Biophysical Letters* 2005, 88, L46-L48.

Another example of a method that utilizes the environmental sensitivity of the amino(oligo)thiophene dyes' spectroscopic properties is a method utilizing one or more of the amino(oligo)thiophene dyes for optical assessment, monitoring, and/or evaluation of protein conformation. In this method, a dye-protein conjugate is formed by reaction of an amino(oligo)thiophene dye having a cysteine-reactive functional group with the cysteine residue of a protein genetically engineered to place the cysteine residue in a site that undergoes a local conformational change on ligand binding. The resulting fluorescent biosensor is used to study conformation changes of the protein. For the preparation and use of biosensors based on other dyes, see, for example, R. M. De Lorimier, J. J. Smith, M. A. Dwyer, L. L. Looger, K. M. Sali, C. D. Paavola, S. S. Rizk, S. Sadigov, D. W. Conrad, L. Loew, and H. W. Helling a, "Construction of a fluorescent biosensor family", *Protein Science* 2002, 11, 2655-2675.

The invention is further illustrated by the following non-limiting examples.

Dye Synthesis and Characterization

Synthesis of Reaction Intermediates

N,N-Disubstituted 5-aminothiophene-2-carboxaldehydes were synthesized by amination in water according to D. Prim, G. Kirsch, J.-F. Nicoud, *Synlett,* 1998, 383-384). N,N-Disubstituted 5'-amino-2,2'-bithiophene-5-carboxaldehydes and 5''-amino-2,2':5',2''-terthiophene-5-carboxaldehydes were synthesized by copper-catalyzed amination according to Z.-K. Lu, R. J. Twieg, *Tetrahedron,* 2005, 61, 903-918; or H. Zhang, Q. Cai, D.-W. Ma, *J. Org. Chem.* 2005, 70, 5164-5173.

EXAMPLE 1

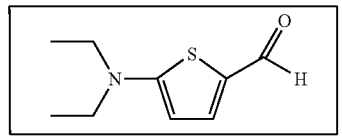

5-Diethylamino-thiophene-2-carboxaldehyde. 5-Bromothiophene-2-carboxaldehyde (380 mg, 2.0 mmol), diethylamine (440 mg, 6.0 mmol), and 10 mL $H_2O$ were stirred at 100° C. in a pressure vessel for 41 h. After cooling down, the organic compounds were separated by extraction with $CH_2Cl_2$, and purified by column chromatography ($SiO_2$, solvent gradient: $CH_2Cl_2$ to 1:1 $CH_2Cl_2$/EtOAc) to furnish 192 mg product (52%). $R_f$ (silica gel, 1:1 $CH_2Cl_2$/EtOAc)=0.63; $^1$H NMR (400 MHz, $CDCl_3$): δ 1.26 (t, J=7.2 Hz, 6 H, 2 $CH_3$), 3.42 (q, J=7.2 Hz, 4 H, 2 $CH_2$), 5.92 (d, J=4.4 Hz, 1 H, ArH), 7.46 (d, J=4.4 Hz, 1 H, ArH), 9.48 (s, 1 H, CHO).

EXAMPLE 2

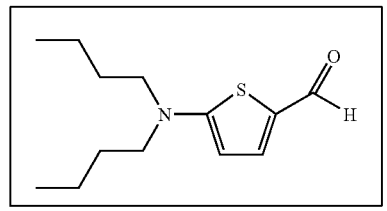

5-Dibutylaminothiophene-2-carboxaldehyde. 5-Bromothiophene-2-carboxaldehyde (380 mg, 2.0 mmol), dibutylamine (770 mg, 6.0 mmol), and 3 mL $H_2O$ were stirred at 100° C. in a pressure vessel for 15 h. After cooling down, the organic compounds were separated by extraction with $CH_2Cl_2$, and purified by column chromatography ($SiO_2$, solvent gradient: $CH_2Cl_2$ to 9:1 $CH_2Cl_2$/EtOAc) to furnish 47 mg product (9.8%). $R_f$ (silica gel, 1:1 Hexane/EtOAc)=0.62; $^1$H NMR (400 MHz, $CDCl_3$): δ 0.96 (t, J=7.2 Hz, 6 H, 2 $CH_3$), 1.36 (m, 4 H, 2 $CH_2$), 1.65 (m, 4 H, 2$CH_2$), 3.33 (t, J=7.8 Hz, 4 H, 2 $NCH_2$), 5.90 (d, J=4.6 Hz, 1 H, ArH), 7.44 (d, J=4.6 Hz, 1 H, ArH), 9.47 (s, 1 H, CHO); MS (EI): m/z=239 $[M]^+$.

EXAMPLE 3

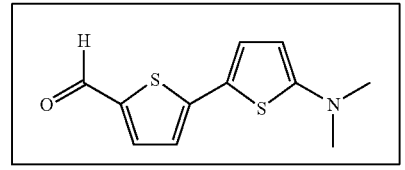

5'-Dimethylamino-2,2'-bithiophene-5-carboxaldehyde. 5'-Bromo-2,2'-bithiophene-5-carboxaldehyde (100 mg, 0.37 mmol), dimethylamine (40% solution in $H_2O$, 1 g, 8.9 mmol), CuI (13.9 mg, 0.073 mmol), Cu (4.7 mg, 0.074 mmol), $K_3PO_4 \cdot H_2O$ (155.4 mg, 0.73 mmol) and 1 mL N,N-dimethylethanolamine were stirred at 80° C. in a pressure vessel for 87 h. Solution turned red during the reaction. After cooling down, the reaction mixture was filtered through a short column of silica gel and eluted with more EtOAc. The eluent was concentrated under vacuum and was purified by column chromatography ($SiO_2$, $CH_2Cl_2$) to furnish 74.8 mg red solid (86%). The product shows strong green fluorescence when dissolved in $CH_2Cl_2$. $R_f$ (silica gel, $CH_2Cl_2$)=0.36; $^1$H NMR (400 MHz, $CDCl_3$): δ 3.00 (s, 6 H, 2 $CH_3$), 5.81 (d, J=4.0 Hz, 1 H, ArH), 6.95 (d, J=4.0 Hz, 1 H, ArH), 7.13 (d, J=4.0 Hz, 1 H, ArH), 7.57 (d, J=4.0 Hz, 1 H, ArH), 9.75 (s, 1 H, CHO); MS (EI): m/z=265 [M]+.

EXAMPLE 4

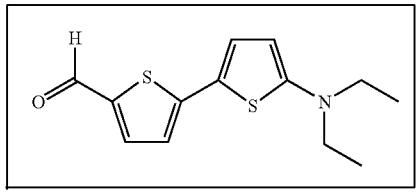

5'-Diethylamino-2,2'-bithiophene-5-carboxaldehyde.
5'-Bromo-2,2'-bithiophene-5-carboxaldehyde (546 mg, 2.0 mmol), diethylamine (293 mg, 4.0 mmol), CuI (76 mg, 0.40 mmol), $K_2CO_3$ (829 mg, 6.0 mmol), (L)-Proline (92 mg, 0.80 mmol) and 5 mL DMSO were stirred at 120° C. in a pressure vessel for 15 h. Solution turned black during the reaction. After cooling down, 10 mL $H_2O$ and 20 mL EtOAc were added to the reaction mixture. The organic compounds were extracted with EtOAc, concentrated under vacuum, and then purified by column chromatography ($SiO_2$, $CH_2Cl_2$) to give 64.5 mg red solid (12%). The product shows strong green fluorescence when dissolved in $CH_2Cl_2$. $R_f$ (silica gel, $CH_2Cl_2$)=0.20;

$^1$H NMR (400 MHz, $CDCl_3$): δ 1.23 (t, J=7.2 Hz, 6 H, 2 $CH_3$), 3.35 (q, J=7.2 Hz, 4 H, 2 $CH_2$), 5.78 (d, J=4.0 Hz, 1 H, ArH), 6.92 (d, J=4.0 Hz, 1 H, ArH), 7.12 (d, J=4.0 Hz, 1 H, ArH), 7.56 (d, J=4.0 Hz, 1 H, ArH), 9.74 (s, 1 H, CHO).

EXAMPLE 5

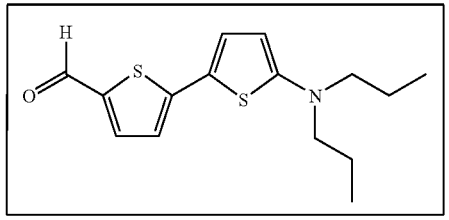

5'-Dipropylamino-2,2'-bithiophene-5-carboxaldehyde.
5'-Bromo-2,2'-bithiophene-5-carboxaldehyde (546 mg, 2.0 mmol), dipropylamine (405 mg, 4.0 mmol), CuI (76 mg, 0.40 mmol), $K_2CO_3$ (829 mg, 6.0 mmol), (L)-Proline (92 mg, 0.80 mmol) and 5 mL DMSO were stirred at 100° C. in a pressure vessel for 18 h. Solution turned brown during the reaction. After cooling down, 10 mL $H_2O$ and 20 mL EtOAc were added to the reaction mixture. The organic compounds were extracted with EtOAc, concentrated under vacuum, and then purified by column chromatography ($SiO_2$, 1:1 Hexane/$CH_2Cl_2$ to $CH_2Cl_2$) to give 56.7 mg red solid (9.7%). The product shows strong green fluorescence when dissolved in $CH_2Cl_2$. $R_f$ (silica gel, $CH_2Cl_2$)=0.21; $^1$H NMR (400 MHz, $CDCl_3$): δ 0.95 (t, J=7.2 Hz, 6 H, 2 $CH_3$), 1.68 (m, 4 H, 2 $CH_2$), 3.24 (t, J=7.6 Hz, 4 H, 2 $CH_2$), 5.75 (d, J=4.0 Hz, 1 H, ArH), 6.91 (d, J=4.0 Hz, 1 H, ArH), 7.11 (d, J=4.0 Hz, 1 H, ArH), 7.56 (d, J=4.0 Hz, 1 H, ArH), 9.74 (s, 1 H, CHO); MS (EI): m/z=293 [M]+.

EXAMPLE 6

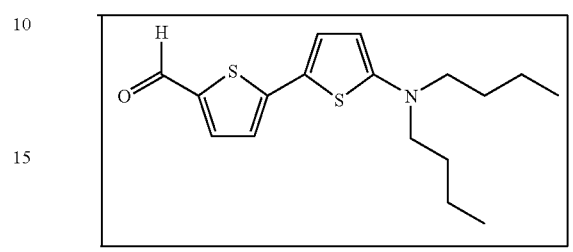

5'-Dibutylamino-2,2'-bithiophene-5-carboxaldehyde.
5'-Bromo-2,2'-bithiophene-5-carboxaldehyde (104 mg, 0.38 mmol), dibutylamine (1.0 g, 7.7 mmol), CuI (13.9 mg, 0.073 mmol), Cu (4.7 mg, 0.074 mmol), $K_3PO_4.H_2O$ (155.4 mg, 0.73 mmol) and 1 mL N,N-dimethylethanolamine were stirred at 80° C. in a pressure vessel for 87 h. After cooling down, the reaction mixture was filtered through a short column of silica gel and eluted with more EtOAc. The eluent was concentrated under vacuum and was purified by column chromatography ($SiO_2$, 1:2 $CH_2Cl_2$/Hex to $CH_2Cl_2$) to furnish 8.0 mg red solid (6.5%). The product shows strong green fluorescence when dissolved in $CH_2Cl_2$. $R_f$ (silica gel, $CH_2Cl_2$)= 0.31; $^1$H NMR (400 MHz, $CDCl_3$): δ 0.96 (t, J=7.2 Hz, 6 H, 2 $CH_3$), 1.36 (m, 4 H, 2 $CH_2$), 1.63 (m, 4 H, 2 $CH_2$), 3.26 (t, J=7.6 Hz, 4 H, 2 $CH_2$), 5.75 (d, J=4.4 Hz, 1 H, ArH), 6.91 (d, J=4.4 Hz, 1 H, ArH), 7.11 (d, J=4.0 Hz, 1 H, ArH), 7.56 (d, J=4.0 Hz, 1 H, ArH), 9.73 (s, 1 H, CHO); MS (EI): m/z=321 [M]+.

EXAMPLE 7

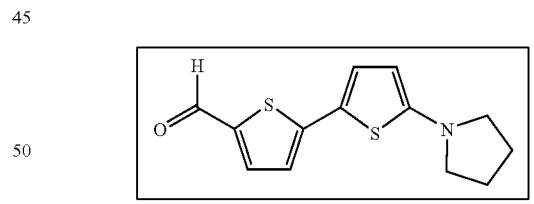

5'-Pyrrolidino-2,2'-bithiophene-5-carboxaldehyde.
5'-Bromo-2,2'-bithiophene-5-carboxaldehyde (100 mg, 0.37 mmol), pyrrolidine (1.0 g, 14 mmol), CuI (26 mg, 0.136 mmol), Cu (7 mg, 0.111 mmol), $K_3PO_4.H_2O$ (155.4 mg, 0.73 mmol) and 1 mL N,N-dimethylethanolamine were stirred at 80° C. in a pressure vessel for 208 h. After cooling down, the reaction mixture was filtered through a short column of silica gel and eluted with more EtOAc. The eluent was concentrated under vacuum and was purified by column chromatography ($SiO_2$, 1:1 $CH_2Cl_2$/Hex) to furnish 4.4 mg red solid (4.6%). The product shows strong green fluorescence when dissolved in $CH_2Cl_2$. $R_f$ (silica gel, $CH_2Cl_2$)=0.16; $^1$H NMR (400 MHz, $CDCl_3$): δ2.07 (m, 4 H, 2 $CH_2$), 3.33 (t, J=6.6 Hz, 4 H, 2

NCH$_2$), 5.70 (d, J=4.4 Hz, 1 H, ArH), 6.92 (d, J=4.0 Hz, 1 H, ArH), 7.15 (d, J=4.0 Hz, 1 H, ArH), 7.57 (d, J=4.0 Hz, 1 H, ArH), 9.74 (s, 1 H, CHO).

EXAMPLE 8

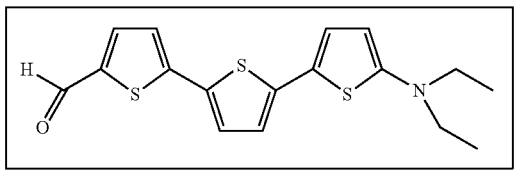

5''-Diethylamino-2,2':5',2''-terthiophene-5-carboxaldehyde. 5''-Bromo-2,2':5',2''-terthiophene-5-carboxaldehyde (100 mg, 0.28 mmol), diethylamine (1.0 g, 14 mmol), CuI (14 mg, 0.074 mmol), Cu (4.7 mg, 0.074 mmol), K$_3$PO$_4$·H$_2$O (155.4 mg, 0.73 mmol) and 1 mL N,N-dimethylethanolamine were stirred at 80° C. in a pressure vessel for 159 h. Solution turned red during the reaction. After cooling down, the reaction mixture was filtered through a short column of silica gel and eluted with more EtOAc. The eluent was concentrated under vacuum and was purified by column chromatography (SiO$_2$, CH$_2$Cl$_2$) to furnish 20.3 mg red solid (20%). The product shows red fluorescence in CH$_2$Cl$_2$. R$_f$ (silica gel, CH$_2$Cl$_2$)=0.39; $^1$H NMR (400 MHz, CDCl$_3$): δ 1.22 (t, J=7.2 Hz, 6 H, 2 CH$_3$), 3.33 (q, J=7.2 Hz, 4 H, 2 CH$_2$), 5.77 (d, J=4.0 Hz, 1 H, ArH), 6.83 (d, J=3.6 Hz, 1 H, ArH), 6.94 (d, J=4.0 Hz, 1 H, ArH), 7.15 (d, J=4.0 Hz, 1 H, ArH), 7.21 (d, J=3.6 Hz, 1 H, ArH), 7.64 (d, J=4.0 Hz, 1 H, ArH), 9.82 (s, 1 H, CHO); MS (EI): m/z=347 [M]$^+$.

EXAMPLE 9

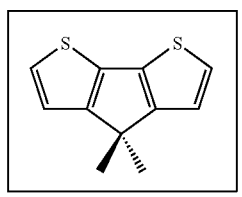

4,4-Dimethyl-4H-cyclopenta[2,1-b:3,4-b']dithiophene. 4H-cyclopenta[2,1-b:3,4-b']dithiophene (500 mg, 2.8 mmol) and KOH (785 mg, 14 mmol) were stirred in 10 mL DMSO for 1 h, and then MeI (500 µL) was added. The reaction was allowed to continue for 20 h at room temperature. 20 mL H$_2$O was added to the reaction mixture and the organic product was extracted with CH$_2$Cl$_2$, concentrated, and purified by column chromatography (SiO$_2$, Hexane) to furnish white solid product (381.2 mg, 66%). R$_f$ (silica gel, 1:1 Hex/CH$_2$Cl$_2$)=0.83; $^1$H NMR (400 MHz, CDCl$_3$): δ 1.45 (s, 6 H, 2 CH$_3$), 6.99 (d, J=4.8 Hz, 2 H, ArH), 7.15 (d, J=4.8 Hz, 1 H, ArH); MS (EI): m/z=206 [M]$^+$.

EXAMPLE 10

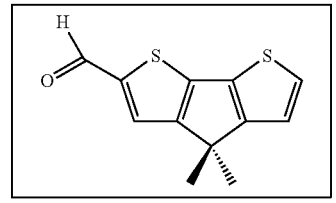

4,4-Dimethyl-4H-cyclopenta[2,1-b:3,4-b']dithiophene-2-carboxaldehyde. 1 mL POCl$_3$ was added to a vigorously stirred solution of 4,4-dimethyl-4H-cyclopenta[2,1-b:3,4-b']dithiophene (381.2 mg, 1.85 mmol) in 6 mL 5:1 CH$_2$Cl$_2$/DMF solvent mixture. The mixture was sealed in a pressure vessel and stirred at 100° C. for 10 min. The solution turned yellow then red upon cooling down. The reaction mixture was then basified with K$_2$CO$_3$ solution, stirred for 30 min more at room temperature to allow complete hydrolysis. The organic product was then extracted with CH$_2$Cl$_2$, concentrated, and purified by column chromatography (SiO$_2$, CH$_2$Cl$_2$) to furnish a yellow oil that solidifies on standing (204 mg, 47%). R$_f$ (silica gel, CH$_2$Cl$_2$)=0.41; $^1$H NMR (400 MHz, CDCl$_3$): δ 1.50 (s, 6 H, 2 CH$_3$), 7.05 (d, J=4.8 Hz, 1 H, ArH), 7.40 (d, J=4.8 Hz, 1 H, ArH), 7.63 (s, 1 H, ArH), 9.83 (s, 1 H, CHO); MS (EI): m/z=234 [M]$^+$.

EXAMPLE 11

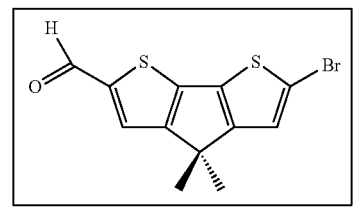

6-Bromo-4,4-dimethyl-4H-cyclopenta[2,1-b:3,4-b']dithiophene-2-carboxaldehyde. NBS (62.8 mg, 0.35 mmol) was added to a vigorously stirred solution of 4,4-Dimethyl-4H-cyclopenta[2,1-b:3,4-b']dithiophene-2-carboxaldehyde (82.7 mg, 0.35 mmol) in 10 mL THF under argon at −78° C. The mixture was allowed to warm up to room temperature slowly (>2 h). The solvent was evaporated under vacuum and the residue was purified by column chromatography (SiO$_2$, CH$_2$Cl$_2$) to furnish the product as yellow crystals (99.3 mg, 90%). R$_f$ (silica gel, CH$_2$Cl$_2$)=0.44;

$^1$H NMR (400 MHz, CDCl$_3$): δ 1.48 (s, 6 H, 2 CH$_3$), 7.07 (s, 1 H, ArH), 7.61 (s, 1 H, ArH), 9.83 (s, 1 H, CHO); MS (EI): m/z=312, 314 [M]$^+$.

EXAMPLE 12

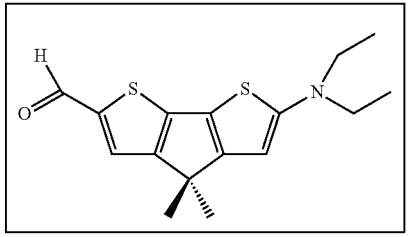

6-Diethylamino-4,4-dimethyl-4H-cyclopenta[2,1-b:3,4-b']dithiophene-2-carboxaldehyde. 6-Bromo-4,4-dimethyl-4H-cyclopenta[2,1-b:3,4-b']dithiophene-2-carboxaldehyde (98.0 mg, 0.31 mmol), diethylamine (0.9 mL, 8.7 mmol), CuI (11.8 mg, 0.06 mmol), K$_2$CO$_3$ (130 mg, 0.94 mmol), (L)-Proline (13.8 mg, 0.12 mmol) and 6 mL DMSO were stirred at 100° C. in a pressure vessel for 17 h. After cooling down, 10 mL H$_2$O and 20 mL EtOAc were added to the reaction mixture. The organic compounds were extracted with EtOAc, concentrated under vacuum, and then purified by column chromatography (SiO$_2$, CH$_2$Cl$_2$ to 1:9 EtOAc/CH$_2$Cl$_2$) to give 7.3 mg product (7.6%). The product in CH$_2$Cl$_2$ shows bright green fluorescence. R$_f$ (silica gel, CH$_2$Cl$_2$)=0.16; $^1$H NMR (400 MHz, CDCl$_3$): δ 1.26 (t, J=7.2 Hz, 6 H, 2 CH$_3$), 1.43 (s, 6 H, 2 CH$_3$), 3.38 (q, J=7.2 Hz, 4 H, 2 CH$_2$), 5.81 (s, 1 H, ArH), 7.46 (s, 1 H, ArH), 9.66 (s, 1 H, CHO); MS (EI): m/z =305 [M]$^+$.

EXAMPLE 13

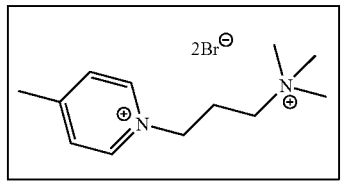

1-(3-Trimethylammoniopropyl)-4-methylpyridinium dibromide (7a). 4-Methylpyridine (367 mg, 3.94 mmol), (3-bromopropyl)trimethylammonium bromide (1.0 g, 3.83 mmol), and 4 mL DMF were stirred at 100° C. in a pressure vessel for 2 h. White precipitates formed during the reaction. After cooling down, the precipitates were filtered out and washed with CH$_2$Cl$_2$ to give 7a as a hygroscopic white solid (1.11 g, 82%), which was used in the next aldol condensation without further purification. $^1$H NMR (400 MHz, CD$_3$OD): δ 2.58 (m, 2 H), 2.71 (s, 3 H), 3.21 (s, 9 H), 3.57 (t, J=8.4 Hz, 2 H), 4.69 (t, J=7.8 Hz, 2 H), 8.00 (d, J=6.6 Hz, 2 H), 8.91 (d, J=6.6 Hz, 2 H); HRMS (FAB+): m/z=273.0963 [M-Br]$^+$ (calcd for C$_{12}$H$_{22}$BrN$_2$: 273.0961).

EXAMPLE 14

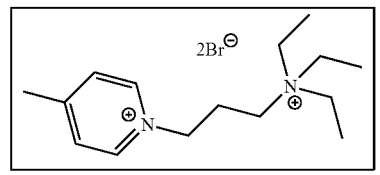

1-(3-Triethylammoniopropyl)-4-methylpyridinium dibromide. 4-Methylpyridine (307 mg, 3.3 mmol), (3-bromopropyl)triethylammonium bromide (1.0 g, 3.3 mmol), and 4 mL DMF were stirred at 100° C. in a pressure vessel for 41 h. Precipitates formed during the reaction. After cooling down, the precipitates were filtered out and washed with CH$_2$Cl$_2$ to give 1-(3-triethylammoniopropyl)-4-methylpyridinium dibromide as a light pink solid (750 mg, 57%), which was used in the next aldol condensation without further purification. $^1$H NMR (400 MHz, CD$_3$OD): δ 1.34 (t, J=7.0 Hz, 9 H), 2.50 (m, 2 H), 2.70 (s, 3 H), 3.35-3.47 (m, 8 H), 4.73 (t, J=7.8 Hz, 2 H), 7.99 (d, J=6.4 Hz, 2 H), 8.98 (d, J=6.4 Hz, 2 H); $^{13}$C NMR (100 MHz, CD$_3$OD): δ 8.0, 22.1, 25.2, 54.4, 54.5, 58.3, 130.1, 145.2, 161.9; HRMS (FAB+): m/z=315.1428 [M-Br]$^+$ (calcd for C$_{15}$H$_{28}$BrN$_2$: 315.1430).

EXAMPLE 15

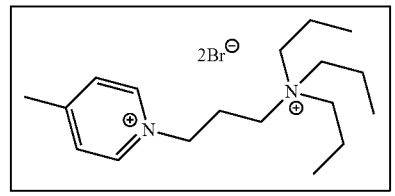

1-(3-Tripropylammoniopropyl)-4-methylpyridinium dibromide. 4-Methylpyridine (307 mg, 3.3 mmol), (3-bromopropyl)tripropylammonium bromide (1.0 g, 2.9 mmol), and 4 mL DMF were stirred at 100° C. in a pressure vessel for 14 h. After cooling down, the reaction mixture was added dropwise to a vigorously stirred diethyl ether (100 mL). The oily precipitates formed was collected and further purified by column chromatography (SiO$_2$, gradient from 1:4 to 1:1 MeOH/CH$_2$Cl$_2$) to furnish 1-(3-tripropylammoniopropyl)-4-methylpyridinium dibromide as a colorless solid (484 mg, 38%). $^1$H NMR (400 MHz, CD$_3$OD): δ 1.03 (t, J=7.0 Hz, 9 H), 1.77 (m, 6 H), 2.51 (m, 2 H), 2.70 (s, 3 H), 3.28 (m, 6 H), 3.49 (m, 2 H), 4.72 (t, J=7.8 Hz, 2 H), 7.99 (d, J=6.4 Hz, 2 H), 8.99 (d, J=6.4 Hz, 2 H); HRMS (FAB+): m/z=357.1906 [M-Br]$^+$ (calcd for $C_{18}H_{34}BrN_2$: 357.1900).

EXAMPLE 16

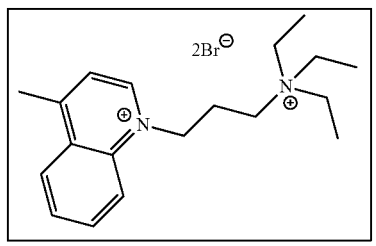

1-(3-Triethylammoniopropyl)-4-methylquinolinium dibromide. 4-Methylquinoline (470 mg, 3.3 mmol), (3-bromopropyl)triethylammonium bromide (1.0 g, 3.3 mmol), and 10 mL acetonitrile were stirred at 90° C. in a pressure vessel for 64 h. After cooling down, the solvent was removed under vacuum and the residue was purified by column chromatography (SiO$_2$, gradient from CH$_2$Cl$_2$ to MeOH) to furnish 1-(3-triethylammoniopropyl)-4-methylquinolinium dibromide as a white solid (1.29 g, 88%). $^1$H NMR (400 MHz, CD$_3$OD): δ 1.35 (t, J=7.4 Hz, 9 H), 2.54 (m, 2 H), 3.10 (s, 3 H), 3.39 (q, J=7.2 Hz, 6 H), 3.60 (t, J=8.0 Hz, 2 H), 5.18 (t, J=8.0 Hz, 2 H), 8.04 (d, J=6.0 Hz, 1 H), 8.09 (t, 1 H), 8.33 (t, 1 H), 8.61 (d, 1 H), 8.65 (d, 1 H), 9.43 (d, J=6.0 Hz, 1 H); HRMS (FAB+): m/z=365.1581 [M-Br]$^+$ (calcd for $C_{19}H_{30}BrN_2$: 365.1587).

EXAMPLE 17

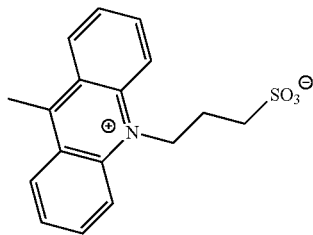

9-Methyl-10-(3-sulfopropyl)acridinium hydroxide inner salt. This compound was prepared using a method reported in Adamczyk, M.; Chen, Y. Y.; Mattingly, P. G.; Pan, Y.; Rege, S. J. Org. Chem. 1998, 63, 5636. A mixture of 9-methylacridine (270 mg, 1.4 mmol) and 1,3-propane sultone (1.8 g, 14.8 mmol) was stirred in a pressure vessel for 4 h at 125° C. After cooling down, the mixture was purified by column chromatography (SiO$_2$, solvent gradient from 5:95 MeOH/CH$_2$Cl$_2$ to 15:85 MeOH/CH$_2$Cl$_2$) to obtain a mixture of yellow strongly fluorescent fractions. This mixture was concentrated and heated with 37 mL 1N HCl to reflux for 4.5 h. Upon cooling down overnight, the water was evaporated off and the oily residue was purified by column chromatography (SiO$_2$, gradient from CH$_2$Cl$_2$ to 1:9 CH$_2$Cl$_2$/MeOH) to furnish 9-methyl-10-(3-sulfopropyl)acridinium hydroxide inner salt as a yellow solid (202 mg, 46%). $^1$H NMR (400 MHz, CD$_3$OD): δ 2.60 (m, 2 H), 3.23 (t, J=6.2 Hz, 2 H), 3.56 (s, 3 H), 5.63 (t, J=8.8 Hz, 2 H), 8.01 (m, 2 H), 8.44 (m, 2 step function. This is in vast contrast to di-4-ANEQPTMA and di-4-ANHTQPTMA, where the exponential time constant exceeds 30 ms, making them unusable for electrophysiological applications.

The effect of the hydrophobicity of the quaternary ammonium head group on voltage sensitivity and kinetics has not been systematically studied previously. The results of experiments with a series of dyes with different head groups are shown in Table 1 and compared in FIG. 6. Since this portion of the dye is outside the chromophore, changes do not significantly affect the shift of electrons in the excited state. This removes the possibility of the head group affecting the electronic mechanism of dye activity. It has been previously documented that it is the hydrophobic tail group that interacts with membrane[19] and it is possible that the interaction of the head group with water could affect the dyes' sensitivities, as the least hydrophobic of these should have the strongest anchoring interactions at the aqueous interface. The results in FIG. 6 indicate that this cannot be an important consideration. SHG signal sensitivity is identical for all three dyes, within an experimental margin of error. Any variations in 2PF signal sensitivity most likely arise from the emission spectra shifting through the detected wavelength bands. However, the SHG kinetics is significantly slower for the trimethylammonium head group compared to the 'instantaneous' changes observed for the other two dyes and this could reflect some rigidification of the dye in the membrane due to strong anchoring.

Figure 7:
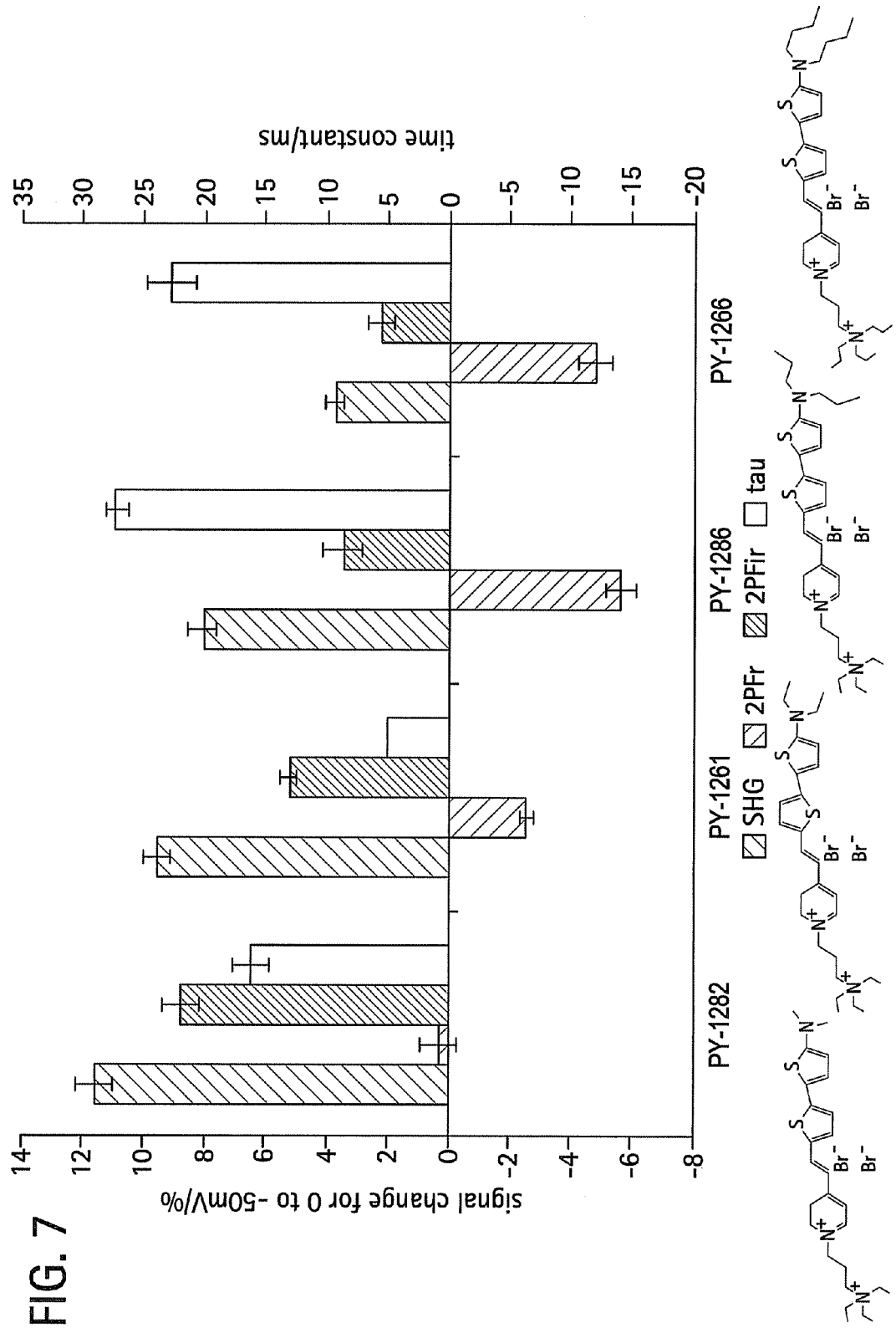
FIG. 7 is a comparison chart showing both signal sensitivities for SHG and 2PF and SHG kinetic response for tail group variation. The left vertical axis shows percentage for signal sensitivity and the right vertical axis shows kinetics in milliseconds, represented by the last bar of each series.

A systematically significant decrease in SHG signal sensitivity is observed in a series of four dyes with varied tail groups. This data is shown in FIG. 7. PY-1282, with two methyl groups at the amino tail, shows a three-fold increase in signal sensitivity when compared with its four-carbon counterpart, PY-1266. Moreover, we observe a statistically significant decrease in SHG sensitivity with each additional carbon added to the tail hydrocarbon chains. The result here suggests that the molecular interaction of the tail group with the membrane dominates the mechanism by which SHG signal changes in response to TMP. SHG signal change could occur by way of a molecular rearrangement occurring in response to a change in TMP. This rearrangement may change the chromophore alignment in the electric field, and thus vary the output signal. Such mechanisms have been described for the H), 8.84 (d, J=9.2 Hz, 2 H), 8.91 (d, J=8.8 Hz, 2 H); HRMS (FAB+): m/z=316.0994 [M+H]$^+$ (calcd for $C_{17}H_{18}NO_3S$: 316.1002).

Synthesis of Dyes

EXAMPLE 18

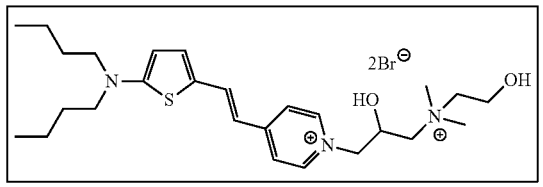

PY-1237. 5-Dibutylamino-thiophene-2-carboxaldehyde (5 mg, 0.02 mmol), 1-[2-hydroxy-3-[N,N-dimethyl-N-(2-hydroxyethyl)ammonio]-propyl]-4-methylpyridinium dibromide (8 mg, 0.02 mmol), 0.1 mL pyrrolidine, and 10 mL ethanol were stirred at 100° C. in a pressure vessel for 2 h. The solution turned red during the reaction. After cooling down, the solvent was evaporated under vacuum and the residue was purified by column chromatography (SiO$_2$-amino, 1:4 MeOH/CH$_2$Cl$_2$) to give PY-1237 as a purple solid (1.2 mg, 10%). R$_f$ (silica gel, 24:4:16:6:6 CHCl$_3$/i-PrOH/MeOH/H$_2$O/AcOH)=0.4; UV/Vis: $\lambda_{EtOH}^{max}$=569 nm, $\lambda_{H_2O}^{max}$=566 nm, $\lambda_{Lipid\ Vesicle}^{max}$=532 nm; Fluorescence: $\lambda_{EtOH}^{max}$=606 nm, $\lambda_{H_2O}^{max}$=614 nm, $\lambda_{Lipid\ Vesicle}^{max}$=584 nm; $^1$H NMR (400 MHz, CDCl$_3$) (aromatic region only): δ 5.91 (d, J =4.6 Hz, 1 H, ArH), 6.15 (d, J=14.8 Hz, 1 H, olefinic H), 7.24 (d, J=4.6 Hz, 1 H, ArH), 7.44 (d, J=6.4 Hz, 2 H, pyridinium H), 7.70 (d, J=14.8 Hz, 1 H, olefinic H), 8.74 (d, J=6.4 Hz, 2 H, pyridinium H).

EXAMPLE 19

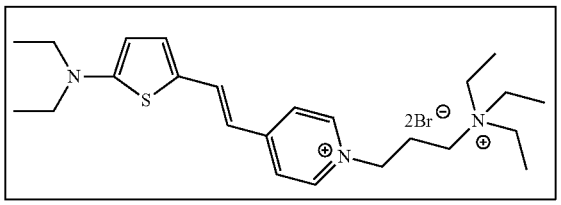

PY-1248. 5-Diethylamino-thiophene-2-carboxaldehyde (18 mg, 0.10 mmol), 1-(3-triethylammoniopropyl)-4-methylpyridinium dibromide (40 mg, 0.1 mmol), 0.1 mL pyrrolidine, and 5 mL ethanol were stirred at 100° C. in a pressure vessel for 16 h. The solution turned red during the reaction. After cooling down, the solvent was evaporated under vacuum and the residue was purified by column chromatography (SiO$_2$-amino, 2:98 MeOH/CH$_2$Cl$_2$ to elute impurities; 1:4 MeOH/CH$_2$Cl$_2$ to elute a purple product) to give PY-1248 as a purple solid (47.0 mg, 84%). R$_f$ (silica gel, 24:4:16:6:6 CHCl$_3$/i-PrOH/MeOH/H$_2$O/AcOH)=0.30; UV/Vis: $\lambda_{EtOH}^{max}$=569 nm, $\lambda_{H_2O}^{max}$=559 nm, $\lambda_{Lipid\ Vesicle}^{max}$=551 nm; Fluorescence: $\lambda_{EtOH}^{max}$=606 nm, $\lambda_{H_2O}^{max}$=612 nm, $\lambda_{Lipid\ Vesicle}^{max}$=586 nm; $^1$H NMR (400 MHz, CD$_3$OD): δ 1.28 (t, J=7.2 Hz, 6 H, 2 CH$_3$), 1.33 (t, J=7.2 Hz, 9 H, 3 CH$_3$), 2.40 (m, 2 H, CH$_2$), 3.34-3.43 (m, 8H, 4 CH$_2$), 3.52 (q, J=7.2 Hz, 4 H, 2CH$_2$), 4.44 (t, 2 H, CH$_2$), 6.11 (d, J=4.4 Hz, 1H, ArH), 6.36 (d, J=15.0 Hz, 1 H, olefinic H), 7.33 (d, J=4.4 Hz, 1 H, ArH), 7.70 (d, J=7.2 Hz, 2 H, pyridinium H), 7.98 (d, J=15.0 Hz, 1 H, olefinic H), 8.43 (br, 2 H, pyridinium H).

EXAMPLE 20

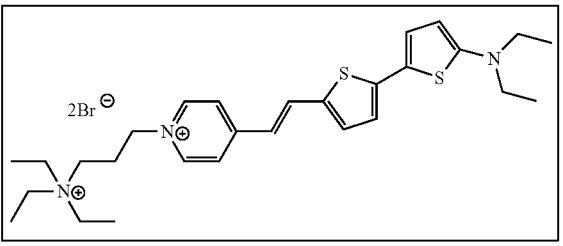

PY-1261. 5'-Diethylamino-2,2'-bithiophene-5-carboxaldehyde (7.3 mg, 0.026 mmol), 1-(3-triethylammoniopropyl)-4-methylpyridinium dibromide (10.0 mg, 0.025 mmol), 0.1 mL pyrrolidine, and 5 mL ethanol were stirred at 70° C. in a pressure vessel for 10 min. The solution turned blue during the reaction. After cooling down, the solvent was evaporated under vacuum and the residue was purified by column chromatography (SiO$_2$-amino, solvent gradient from 2:98 MeOH/CH$_2$Cl$_2$ to 10:90 MeOH/CH$_2$Cl$_2$) to give PY-1261 as a blue solid (13.3 mg, 83%). R$_f$ (silica gel, 24:4:16:6:6 CHCl$_3$/i-PrOH/MeOH/H$_2$O/AcOH)=0.38; UV/Vis: $\lambda_{EtOH}^{max}$=614 nm, $\lambda_{H_2O}^{max}$=539 nm, $\lambda_{Lipid\ Vesicle}^{max}$=547 nm; Fluorescence: $\lambda_{Lipid\ Vesicle}^{max}$=686 nm; $^1$H NMR (400 MHz, CD$_3$OD): δ 1.24 (t, J=7.2 Hz, 6 H, 2 CH$_3$), 1.33 (t, J=7.2 Hz, 9 H, 3 CH$_3$), 2.43 (m, 2 H, CH$_2$), 3.34-3.43 (m, 12 H, 6 CH$_2$N), 4.54 (t, 2 H, CH$_2$), 5.90 (d, J =4.0 Hz, 1 H, ArH), 6.88 (d, J=15.4 Hz, 1 H, olefinic H), 6.97 (d, J=4.0 Hz, 1 H, ArH), 7.12 (d, J=4.0 Hz, 1 H, ArH), 7.36 (d, J=4.0 Hz, 1 H, ArH), 8.03 (d, J=7.2 Hz, 2 H, pyridinium H), 8.08 (d, J=15.4 Hz, 1 H, olefinic H), 8.67 (br, 2 H, pyridinium H); $^{13}$C NMR (100 MHz, CD$_3$OD): δ 7.8, 12.6, 24.9, 48.2, 54.4, 57.5, 103.4, 119.51, 119.52, 122.0, 124.0, 128.4, 136.5, 136.7, 137.0, 144.6, 146.8, 155.9, 160.1; HRMS (FAB+): m/z=562.1921 [M-Br]$^+$ (calcd for C$_{28}$H$_{41}$BrN$_3$S$_2$: 562.1925).

EXAMPLE 21

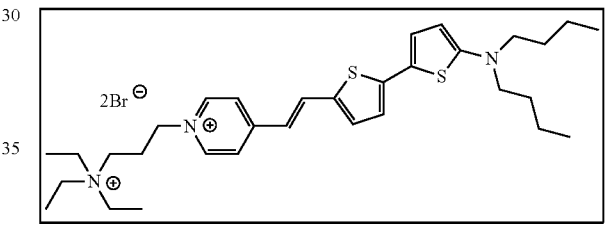

PY-1266. 5'-Dibutylamino-2,2'-bithiophene-5-carboxaldehyde (2.5 mg, 7.4 μmol), 1-(3-triethylammoniopropyl)-4-methylpyridinium dibromide (2.9 mg, 7.4 μmol), 0.1 mL pyrrolidine, and 5 mL ethanol were stirred at 80° C. in a pressure vessel for 5 min. The solution turned blue during the reaction. After cooling down, the solvent was evaporated under vacuum and the residue was purified by column chromatography (SiO$_2$-amino, solvent gradient from 2:98 MeOH/CH$_2$Cl$_2$ to 16:84 MeOH/CH$_2$Cl$_2$) to give PY-1266 as a blue solid (4.7 mg, 90%). R$_f$ (silica gel, 24:4:16:6:6 CHCl$_3$/i-PrOH/MeOH/H$_2$O/AcOH)=0.22; UV/Vis: $\lambda_{EtOH}^{max}$=624 nm, $\lambda_{H_2O}^{max}$=555 nm, $\lambda_{Lipid\ Vesicle}^{max}$=552 nm; Fluorescence: $\lambda_{Lipid\ Vesicle}^{max}$=694 nm; $^1$H NMR (400 MHz, CD$_3$OD): δ 0.99 (t, J=7.2 Hz, 6 H, 2 CH$_3$), 1.23-1.45 (m, 13 H, 3 CH$_3$ and 2 CH$_2$), 1.60-1.70 (m, 4 H, 2 CH$_2$), 2.45 (m, 2 H, CH$_2$), 3.33-3.45 (m, 12 H, 6 CH$_2$N), 4.58 (t, 2 H, CH$_2$), 5.85 (d, J=4.4 Hz, 1 H, ArH), 6.86 (d, J=15.6 Hz, 1 H, olefinic H), 6.95 (d, J=4.0 Hz, 1 H, ArH), 7.11 (d, J=4.4 Hz, 1 H, ArH), 7.35 (d, J=4.0 Hz, 1 H, ArH), 8.01 (d, J=6.6 Hz, 2 H, pyridinium H), 8.07 (d, J=15.6 Hz, 1 H, olefinic H), 8.73 (d, J=6.6 Hz, 2 H, pyridinium H); HRMS (FAB+): m/z=618.2559 [M-Br]$^+$ (calcd for C$_{32}$H$_{49}$BrN$_3$S$_2$: 618.2551).

EXAMPLE 22

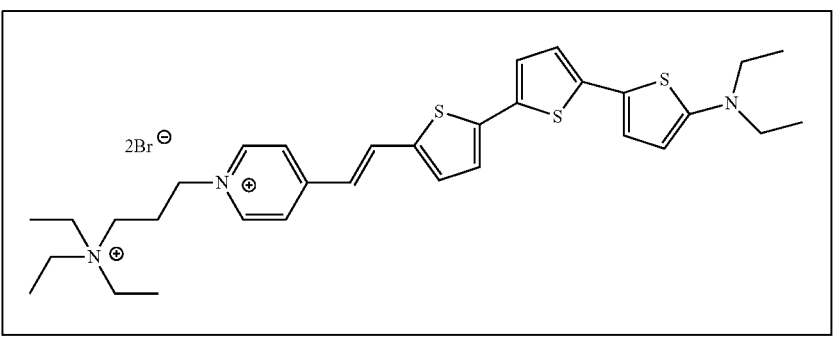

PY-1268. 5"-Diethylamino-2,2':5',2"-terthiophene-5-carboxaldehyde (7.0 mg, 19 μmol), 1-(3-triethylammoniopropyl)-4-methylpyridinium dibromide (7.6 mg, 19 μmol), 0.1 mL pyrrolidine, and 5 mL ethanol were stirred at 80° C. in a pressure vessel for 5 min. The solution turned dark during the reaction. After cooling down, the solvent was evaporated under vacuum and the residue was purified by column chromatography (SiO$_2$-amino, solvent gradient from CH$_2$Cl$_2$ to 5:95 MeOH/CH$_2$Cl$_2$) to give PY-1268 as a blue solid (12.6 mg, 90%). R$_f$ (silica gel, 24:4:16:6:6 CHCl$_3$/i-PrOH/MeOH/H$_2$O/AcOH)=0.19; UV/Vis: $\lambda_{EtOH}^{max}$=588 nm, $\lambda_{H_2O}^{max}$=508 nm, $\lambda_{Lipid\ Vesicle}^{max}$=535 nm; Fluorescence: $\lambda_{EtOH}^{max}$=606 nm, $\lambda_{H_2O}^{max}$=596 nm, $\lambda_{Lipid\ Vesicle}^{max}$=714 nm; $^1$H NMR (400 MHz, CD$_3$OD): δ 1.22 (t, J=7.2 Hz, 6 H, 2 CH$_3$), 1.34 (t, J=7.2 Hz, 9 H, 3 CH$_3$), 2.46 (m, 2 H, CH$_2$), 3.30-3.45 (m, 12 H, 6 CH$_2$N), 4.60 (t, J=7.6 Hz, 2 H, CH$_2$), 5.84 (d, J=4.4 Hz, 1 H, ArH), 6.89 (d, J=4.0 Hz, 1 H, ArH), 6.96 (d, J=4.0 Hz, 1 H, ArH), 7.06 (d, J=15.2 Hz, 1 H, olefinic H), 7.23 (d, J =4.0 Hz, 1 H, ArH), 7.25 (d, J=4.0 Hz, 1 H, ArH), 7.43 (d, J=4.0 Hz, 1 H, ArH), 8.12 (d, J=6.4 Hz, 2 H, pyridinium H), 8.12 (d, J=15.6 Hz, 1 H, olefinic H), 8.81 (br, 2 H, pyridinium H); HRMS (FAB+): m/z=644.1783 [M-Br]$^+$ (calcd for C$_{32}$H$_{43}$BrN$_3$S$_3$: 644.1802).

EXAMPLE 23

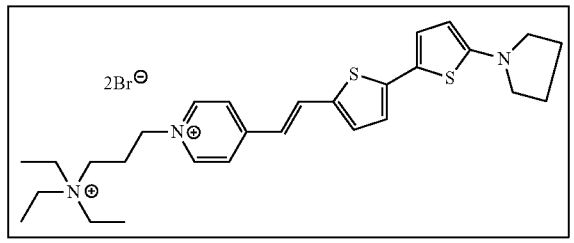

PY-1274. 5'-Pyrrolidino-2,2'-bithiophene-5-carboxaldehyde (2.0 mg, 7.6 μmol), 1-(3-triethylammoniopropyl)-4-methylpyridinium dibromide (3.0 mg, 7.6 μmol), 0.1 mL pyrrolidine, and 5 mL ethanol were stirred at 80° C. in a pressure vessel for 5 min. The solution turned greenish dark during the reaction. After cooling down, the solvent was evaporated under vacuum and the residue was purified by column chromatography (SiO$_2$-amino, solvent gradient from 2:98 MeOH/CH$_2$Cl$_2$ to 1:4 MeOH/CH$_2$Cl$_2$) to give PY-1274 as a blue solid (1.6 mg, 33%). R$_f$ (silica gel, 24:4:16:6:6 CHCl$_3$/i-PrOH/MeOH/H$_2$O/AcOH)=0.06; UV/Vis: $\lambda_{EtOH}^{max}$=618 nm, $\lambda_{H_2O}^{max}$=558 nm, $\lambda_{Lipid\ Vesicle}^{max}$=551 nm; Fluorescence: $\lambda_{Lipid\ Vesicle}^{max}$=691 nm; $^1$H NMR (400 MHz, CD$_3$OD) (aromatic region only): δ 5.79 (d, J=4.4 Hz, 1 H, ArH), 6.87 (d, J=15.6 Hz, 1 H, olefinic H), 6.97 (d, J=4.0 Hz, 1 H, ArH), 7.15 (d, J=4.4 Hz, 1 H, ArH), 7.35 (d, J=4.0 Hz, 1 H, ArH), 8.02 (d, J=6.6 Hz, 2 H, pyridinium H), 8.08 (d, J=15.6 Hz, 1 H, olefinic H), 8.67 (d, J=6.6 Hz, 2 H, pyridinium H).

EXAMPLE 24

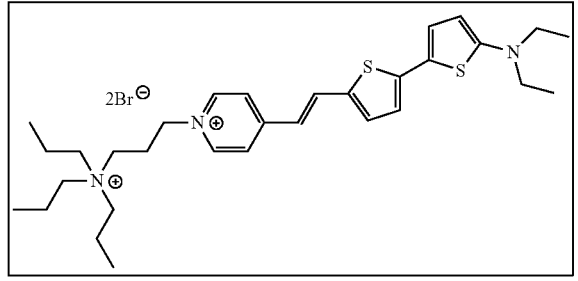

PY-1278. 5'-Diethylamino-2,2'-bithiophene-5-carboxaldehyde (5.0 mg, 0.018 mmol), 1-(3-tripropylammoniopropyl)-4-methylpyridinium dibromide (7.8 mg, 0.018 mmol), 0.1 mL pyrrolidine, and 5 mL ethanol were stirred at 100° C. in a pressure vessel for 10 min. The solution turned blue during the reaction. After cooling down, the solvent was evaporated under vacuum and the residue was purified by column chromatography (SiO$_2$-amino, solvent gradient from 2:98 MeOH/CH$_2$Cl$_2$ to 1:4 MeOH/CH$_2$Cl$_2$) to give PY-1278 as a blue solid (6.3 mg, 51%). R$_f$ (silica gel, 24:4:16:6:6 CHCl$_3$/i-PrOH/MeOH/H$_2$O/AcOH)=0.44; UV/Vis: $\lambda_{EtOH}^{max}$=612 nm, $\lambda_{H_2O}^{max}$=544 nm, $\lambda_{Lipid\ Vesicle}^{max}$=555 nm; Fluorescence: $\lambda_{Lipid\ Vesicle}^{max}$=688 nm; $^1$H NMR (400 MHz, CD$_3$OD): δ 1.03 (t, J=7.2 Hz, 9 H, 3 CH$_3$), 1.23 (t, J=7.2 Hz, 6 H, 2 CH$_3$), 1.67-1.84 (m, 6 H, 3CH$_2$), 2.44 (m, 2 H, CH$_2$), 3.26 (m, 6 H, 3 NCH$_2$), 3.36-3.46 (m, 6 H, 3 CH$_2$N), 4.52 (t, J=7.2 Hz, 2 H, CH$_2$), 5.89 (d, J=4.4 Hz, 1 H, ArH), 6.88 (d, J=15.6 Hz, 1 H, olefinic H), 6.97 (d, J=4.0 Hz, 1 H, ArH), 7.13 (d, J=4.0 Hz, 1 H, ArH), 7.36 (d, J=4.0 Hz, 1 H, ArH), 8.03 (d, J=7.2 Hz, 2 H, pyridinium H), 8.08 (d, J=15.6

Hz, 1 H, olefinic H), 8.68 (br, 2 H, pyridinium H); HRMS (FAB+): m/z=604.2414 [M-Br]⁺ (calcd for $C_{31}H_{47}BrN_3S_2$: 604.2395).

EXAMPLE 25

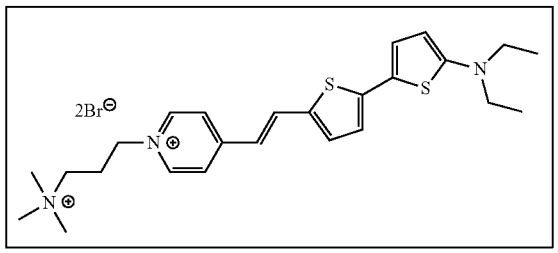

PY-1280. 5'-Diethylamino-2,2'-bithiophene-5-carboxaldehyde (5.0 mg, 0.018 mmol), 1-(3-trimethylammoniopropyl)-4-methylpyridinium dibromide (6.3 mg, 0.018 mmol), 0.1 mL pyrrolidine, and 5 mL ethanol were stirred at 100° C. in a pressure vessel for 5 min. The solution turned blue during the reaction. After cooling down, the solvent was evaporated under vacuum and the residue was purified by column chromatography ($SiO_2$-amino, solvent gradient from 2:98 MeOH/ $CH_2Cl_2$ to 1:4 MeOH/$CH_2Cl_2$) to give PY-1280 as a blue solid (10.0 mg, 94%). $R_f$ (silica gel, 24:4:16:6:6 $CHCl_3$/i-PrOH/MeOH/$H_2O$/AcOH)=0.21; UV/Vis: $\lambda_{EtOH}^{max}$=617 nm, $\lambda_{H_2O}^{max}$=544 nm, $\lambda_{Lipid\ Vesicle}^{max}$=547 nm; Fluorescence: $\lambda_{Lipid\ Vesicle}^{max}$=690 n; ¹H NMR (400 MHz, $CD_3OD$): δ 1.23 (t, J=7.0 Hz, 6 H, 2 $CH_3$), 2.54 (m, 2 H, $CH_2$), 3.20 (s, 9 H, 3 $NCH_3$), 3.40 (q, J=7.2 Hz, 4 H, 2 $CH_2N$), 3.54 (m, 2 H, $NCH_2$), 4.56 (t, J=7.6 Hz, 2 H, $CH_2$), 5.89 (d, J=4.4 Hz, 1 H, ArH), 6.88 (d, J=15.8 Hz, 1 H, olefinic H), 6.96 (d, J=4.0 Hz, 1 H, ArH), 7.12 (d, J=4.0 Hz, 1 H, ArH), 7.35 (d, J=4.4 Hz, 1 H, ArH), 8.02 (d, J=6.4 Hz, 2 H, pyridinium H), 8.08 (d, J=15.8 Hz, 1 H, olefinic H), 8.68 (br, 2 H, pyridinium H); HRMS (FAB+): m/z=520.1457 [M-Br]⁺ (calcd for $C_{25}H_{35}BrN_3S_2$: 520.1456).

EXAMPLE 26

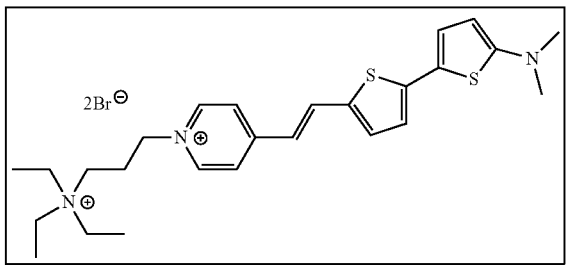

PY-1282. 5'-Dimethylamino-2,2'-bithiophene-5-carboxaldehyde (10.0 mg, 0.042 mmol), 1-(3-triethylammoniopropyl)-4-methylpyridinium dibromide (6.3 mg, 0.018 mmol), 0.1 mL pyrrolidine, and 5 mL ethanol were stirred at 100° C. in a pressure vessel for 5 min. The solution turned blue during the reaction. After cooling down, the solvent was evaporated under vacuum and the residue was purified by column chromatography ($SiO_2$-amino, solvent gradient from 2:98 MeOH/ $CH_2Cl_2$ to 1:4 MeOH/$CH_2Cl_2$) to give PY-1282 as a blue solid (18.5 mg, 71%). $R_f$ (silica gel, 24:4:16:6:6 $CHCl_3$/i-PrOH/MeOH/$H_2O$/AcOH)=0.27; UV/Vis: $\lambda_{EtOH}^{max}$=594 nm, $\lambda_{H_2O}^{max}$=529 nm, $\lambda_{Lipid\ Vesicle}^{max}$=530 nm; Fluorescence: $\lambda_{Lipid\ Vesicle}^{max}$=676 nm; ¹H NMR (400 MHz, $CD_3OD$): δ 1.34 (t, J=7.2 Hz, 9 H, 3 $CH_3$), 2.45 (m, 2 H, $CH_2$), 3.00 (s, 6 H, 2 $NCH_3$), 3.39 (m, 8 H, 4 $CH_2N$), 4.57 (t, 2 H, $CH_2$), 5.92 (d, J=4.0 Hz, 1 H, ArH), 6.91 (d, J=15.6 Hz, 1 H, olefinic H), 7.00 (d, J=4.0 Hz, 1 H, ArH), 7.14 (d, J =4.0 Hz, 1 H, ArH), 7.37 (d, J=4.0 Hz, 1 H, ArH), 8.05 (d, J=6.8 Hz, 2 H, pyridinium H), 8.09 (d, J=15.6 Hz, 1 H, olefinic H), 8.72 (br, 2 H, pyridinium H);

¹³C NMR (100 MHz, $CD_3OD$): δ 7.9, 25.0, 42.6, 54.4, 57.5, 104.1, 119.9, 121.0, 122.3, 124.1, 128.1, 136.3, 136.6, 137.4, 144.7, 146.4, 155.9, 162.2; HRMS (FAB+): m/z=534.1631 [M-Br]⁺ (calcd for $C_{26}H_{37}BrN_3S_2$: 534.1612).

EXAMPLE 27

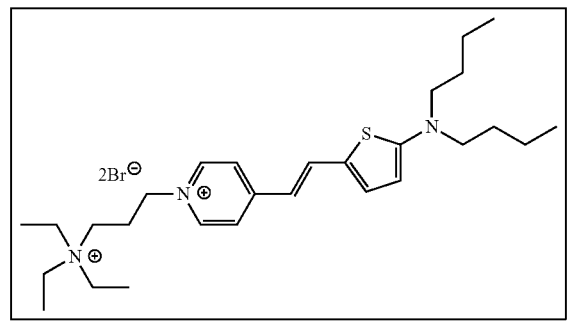

PY-1284. 5-Dibutylamino-thiophene-2-carboxaldehyde (10.0 mg, 0.04 mmol), 1-(3-triethylammoniopropyl)-4-methylpyridinium dibromide (16.6 mg, 0.04 mmol), 0.1 mL pyrrolidine, and 5 mL ethanol were stirred at 100° C. in a pressure vessel for 2 h. The solution turned purple and then red during the reaction. After cooling down, the solvent was evaporated under vacuum and the residue was purified by column chromatography ($SiO_2$-amino, 2:98 MeOH/$CH_2Cl_2$ to elute impurities; 5:95 MeOH/$CH_2Cl_2$ to elute a purple product) to give PY-1284 as a purple solid (12.4 mg, 50%). $R_f$ (silica gel, 24:4:16:6:6 $CHCl_3$/i-PrOH/MeOH/$H_2O$/AcOH)= 0.27;

UV/Vis: $\lambda_{EtOH}^{max}$=571 nm, $\lambda_{H_2O}^{max}$=564 nm, $\lambda_{Lipid\ Vesicle}^{max}$=536 nm; Fluorescence: $\lambda_{EtOH}^{max}$=610 nm, $\lambda_{H_2O}^{max}$=614 nm, $\lambda_{Lipid\ Vesicle}^{max}$=588 mm; ¹H NMR (400 MHz, $CD_3OD$): δ 1.00 (t, J=7.2 Hz, 6 H, 2 $CH_3$), 1.26-1.47 (m, 13 H, 2$CH_2$ and 3 $CH_3$), 1.70 (m, 4 H, 2 $CH_2$), 2.37 (m, 2 H, $CH_2$), 3.33-3.41 (m, 8 H, 4 $CH_2$), 3.45 (q, J=7.6 Hz, 4 H, 2$CH_2$), 4.39 (t, J=7.6 Hz, 2 H, $CH_2$), 6.09 (d, J=4.4 Hz, 1 H, ArH), 6.35 (d, J=14.8 Hz, 1 H, olefinic H), 7.32 (d, J=4.4 Hz, 1 H, ArH), 7.70 (d, J=7.2 Hz, 2 H, pyridinium H), 7.97 (d, J=14.8 Hz, 1 H, olefinic H), 8.36 (d, J=6.8 Hz, 2 H, pyridinium H); HRMS (FAB+): m/z=536.2675 [M-Br]+ (calcd for $C_{28}H_{47}BrN_3S$: 536.2674).

EXAMPLE 28

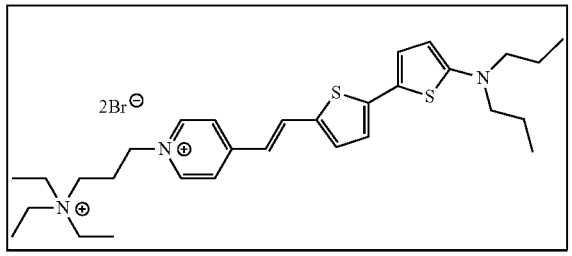

PY-1286. 5'-Dipropylamino-2,2'-bithiophene-5-carboxaldehyde (10.0 mg, 0.034 mmol), 1-(3-triethylammoniopropyl)-4-methylpyridinium dibromide (13.5 mg, 0.034 mmol), 0.1 mL pyrrolidine, and 10 mL ethanol were stirred at 100° C. in a pressure vessel for 10 min. The solution turned blue during the reaction. After cooling down, the solvent was evaporated under vacuum and the residue was purified by column chromatography ($SiO_2$-amino, solvent gradient from 2:98 MeOH/$CH_2Cl_2$ to 5:95 MeOH/$CH_2Cl_2$) to give PY-1286 as a blue solid (8.7 mg, 38%). $R_f$ (silica gel, 24:4:16:6:6 $CHCl_3$/i-PrOH/MeOH/$H_2O$/AcOH)=0.16; UV/Vis: $\lambda_{EtOH}^{max}$=616 nm, $\lambda_{H_2O}^{max}$=567 nm, $\lambda_{Lipid\ Vesicle}^{max}$=547 nm; Fluorescence: $\lambda_{Lipid\ Vesicle}^{max}$=692 nm; $^1$H NMR (400 MHz, $CD_3OD$): δ 0.97 (t, J=7.2 Hz, 6 H, 2 $CH_3$), 1.33 (t, J=7.2 Hz, 9 H, 3 $CH_3$), 1.64-1.76 (m, 4 H, 2 $CH_2$), 2.43 (m, 2 H, $CH_2$), 3.34-3.43 (m, 12 H, 6 $CH_2N$), 4.54 (t, J=7.8 Hz, 2 H, $CH_2$), 5.86 (d, J=4.0 Hz, 1 H, ArH), 6.87 (d, J=15.2 Hz, 1 H, olefinic H), 6.96 (d, J=4.0 Hz, 1 H, ArH), 7.12 (d, J=4.0 Hz, 1 H, ArH), 7.35 (d, J=4.0 Hz, 1 H, ArH), 8.02 (d, J=7.0 Hz, 2 H, pyridinium H), 8.08 (d, J=15.2 Hz, 1 H, olefinic H), 8.68 (d, J=7.0 Hz, 2 H, pyridinium H); HRMS (FAB+): m/z=590.2266 [M-Br]+ (calcd for $C_{30}H_{45}BrN_3S_2$: 590.2238).

EXAMPLE 29

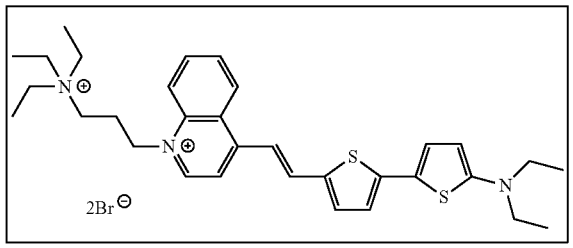

PY-2120. 5'-Diethylamino-2,2'-bithiophene-5-carboxaldehyde (6.3 mg, 0.022 mmol), 1-(3-triethylammoniopropyl)-4-methylquinolinium dibromide (10.0 mg, 0.022 mmol), 0.1 mL pyrrolidine, and 5 mL ethanol were stirred at 100° C. in a pressure vessel for 6 min. The solution turned green during the reaction. After cooling down, the solvent was evaporated under vacuum and the residue was purified by column chromatography ($SiO_2$-amino, solvent gradient from 2:98 MeOH/$CH_2Cl_2$ to 10:90 MeOH/$CH_2Cl_2$) to give PY-2120 as a green solid (2.4 mg, 16%). $R_f$ (silica gel, 24:4:16:6:6 $CHCl_3$/i-PrOH/MeOH/$H_2O$/AcOH)=0.20; UV/Vis: $\lambda_{EtOH}^{max}$=734 nm, $\lambda_{H_2O}^{max}$=640 nm, $\lambda_{Lipid\ Vesicle}^{max}$=620 nm; Fluorescence: $\lambda_{Lipid\ Vesicle}^{max}$=758 nm; $^1$H NMR (400 MHz, $CD_3OD$): δ 1.25 (t, J=7.2 Hz, 6 H, 2 $CH_3$), 1.33 (t, J=7.2 Hz, 9 H, 3$CH_3$), 2.47 (m, 2 H, $CH_2$), 3.34-3.47 (m, 10 H, 5 $CH_2N$), 3.51-3.58 (m, 2 H, $CH_2N$), 4.98 (t, J=7.6 Hz, 2 H, $CH_2$), 5.95 (d, J=4.0 Hz, 1 H, ArH), 7.04 (d, J=4.0 Hz, 1 H, ArH), 7.24 (d, J=4.0 Hz, 1 H, ArH), 7.52 (d, J=4.0 Hz, 1 H, ArH), 7.65 (d, J=15.0 Hz, 1 H, olefinic H), 7.99 (t, J=7.6 Hz, 1 H, ArH), 8.19-8.26 (m, 2 H, ArH), 8.32 (d, J=15.0 Hz, 1 H, olefinic H), 8.43 (d, J=8.4 Hz, 1 H, ArH), 8.79 (d, J=8.0 Hz, 1 H, ArH), 9.02 (d, J=6.8 Hz, 1 H, ArH); HRMS (FAB+): m/z=612.2070 [M-Br]+ (calcd for $C_{32}H_{43}BrN_3S_2$: 612.2082).

EXAMPLE 30

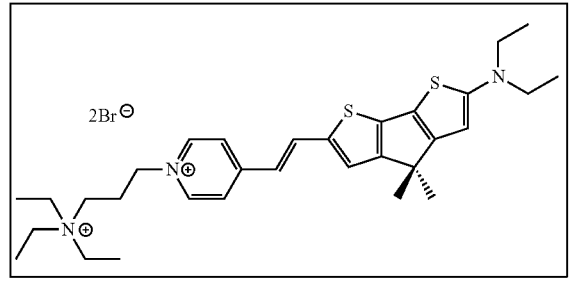

PY-2174. 6-Diethylamino-4,4-dimethyl-4H-cyclopenta[2,1-b:3,4-b']dithiophene-2-carboxaldehyde (2.0 mg, 6.5 μmol), 1-(3-triethylammoniopropyl)-4-methylpyridinium dibromide (2.6 mg, 6.5 μmol), 0.1 mL pyrrolidine, and 5 mL ethanol were stirred at 100° C. in a pressure vessel for 10 min. The solution turned green during the reaction. After cooling down, the solvent was evaporated under vacuum and the residue was purified by column chromatography ($SiO_2$-amino, solvent gradient from $CH_2Cl_2$ to 1:9 MeOH/$CH_2Cl_2$) to give PY-2174 as a blue solid (4.0 mg, 89%). $R_f$ (silica gel, 24:4:16:6:6 $CHCl_3$/i-PrOH/MeOH/$H_2O$/AcOH)=0.41; UV/Vis: $\lambda_{EtOH}^{max}$=707 nm, $\lambda_{H_2O}^{max}$=552 nm, $\lambda_{Lipid\ Vesicle}^{max}$=612 nm; Fluorescence: $\lambda_{Lipid\ Vesicle}^{max}$=704 nm; $^1$H NMR (400 MHz, $CD_3OD$): δ 1.26 (t, J=7.2 Hz, 6 H, 2 $CH_3$), 1.33 (t, J=7.2 Hz, 9 H, 3 $CH_3$), 1.45 (s, 6 H, 2 $CH_3$), 2.38 (m, 2 H, $CH_2$), 3.34-3.43 (m, 12 H, 6 $CH_2N$), 4.42 (t, J=7.6 Hz, 2 H, $CH_2$), 6.05 (s, 1 H, ArH), 6.70 (d, J=15.0 Hz, 1 H, olefinic H), 7.37 (s, 1 H, ArH), 7.78 (d, J=7.0 Hz, 2 H, pyridinium H), 8.08 (d, J=15.0 Hz, 1 H, olefinic H), 8.41 (d, J=7.0 Hz, 2 H, pyridinium H); HRMS (FAB+): m/z=602.2220 [M-Br]⁺ (calcd for $C_{31}H_{45}BrN_3S_2$: 602.2238).

EXAMPLE 31

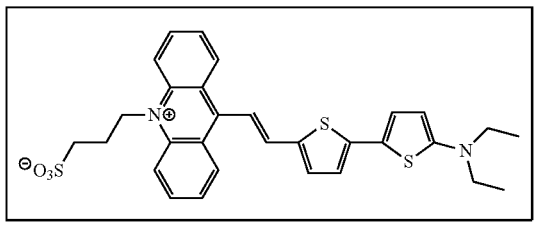

PY-2240. 5'-Diethylamino-2,2'-bithiophene-5-carboxaldehyde (2.8 mg, 0.01 mmol), 9-methyl-10-(3-sulfopropyl) acridinium hydroxide inner salt (3.1 mg, 0.01 mmol), and 1 mL acetic anhydride were stirred at 120° C. in a pressure vessel for 1 h. The solution turned green during the reaction. After cooling down, the solvent was evaporated under vacuum and the residue was purified by column chromatography (SiO₂, 1:9 MeOH/CH₂Cl₂) to give 3 as a green solid (2.4 mg, 37%). $R_f$(silica gel, 1:4 MeOH/CH₂Cl₂)=0.58; ¹H NMR (400 MHz, CD₃OD): δ 1.26 (t, J=7.2 Hz, 6 H), 2.55 (m, 2 H), 3.20 (t, J=6.4 Hz, 2 H), 3.43 (q, J=7.2 Hz, 4 H), 5.35 (t, J=8.8 Hz, 2 H), 5.95 (d, J=4.4 Hz, 1 H), 6.97 (d, J=4.4 Hz, 1 H), 7.19 (d, J=4.4 Hz, 1 H), 7.43 (d, J=4.4 Hz, 1 H), 7.68 (d, J=15.2 Hz, 1 H), 7.83 (m, 2 H), 7.88 (d, J=15.2 Hz, 1 H), 8.27 (m, 2 H), 8.58 (d, J=9.2 Hz, 2 H), 8.70 (dd, J=8.4 Hz, 1.2 Hz, 2 H); HRMS (FAB+): m/z=563.1480 [M+H]⁺ (calcd for $C_{30}H_{31}N_2O_3S_3$: 563.1497).

EXAMPLE 32

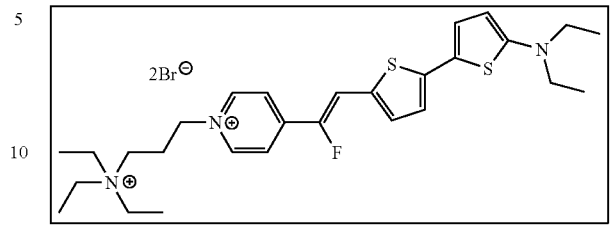

PY-3008. 5-Diethylamino-thiophene-2-carboxaldehyde (5.6 mg, 0.02 mmol), 1-(3-triethylammoniopropyl)-4-fluoromethylpyridinium dibromide (8.3 mg, 0.02 mmol), 0.1 mL pyrrolidine, and 2 mL ethanol were stirred at RT for 25 min. The solvent was evaporated under vacuum and the residue was purified by column chromatography (SiO₂-amino, 5:95 MeOH/CH₂Cl₂) to give PY-3008 as a blue solid (5.3 mg, 40%). $R_f$(silica gel, 24:4:16:6:6 CHCl₃/i-PrOH/MeOH/H₂O/AcOH) 0.26;

UV/Vis: $\lambda_{EtOH}^{max}$=637 nm, $\lambda_{H_2O}^{max}$=565 nm, $\lambda_{Lipid\ Vesicle}^{max}$=565 nm; Fluorescence: $\lambda_{Lipid\ Vesicle}^{max}$=706 nm; ¹H NMR (400 MHz, CD₃OD): δ 1.24 (t, J=7.2 Hz, 6 H, 2 CH₃), 1.34 (t, J=7.2 Hz, 9 H, 3 CH₃), 2.47 (m, 2 H, CH₂), 3.34-3.43 (m, 12 H, 6 CH₂N), 4.63 (t, 2 H, CH₂), 5.90 (d, J=2.4 Hz, 1 H, ArH), 7.02 (dd, J=2.4, 4 Hz, 1 H), 7.14 (d, J=4.4 Hz, 1 H), 7.45 (d, J=4.0 Hz, 1 H, ArH), 7.83 (d, J=38.4 Hz, 1 H), 8.14 (d, J=7.8 Hz, 2 H, pyridinium H), 8.86 (d, J=7.84 Hz, 1 H, pyridinium H).

SHG and 2PF Experiments

Dyes

The series of dyes used in this work are shown in Table 1. Synthesis of the amino(oligo)thiophene dyes is discussed above. The "QPQ" based dyes were synthesized by Joseph P. Wuskell and show variation in the number of double bonds in the chromophore.

The comparison of the results for the fluorinated dye PY-3008 to those for the corresponding unfluorinated dye PY-1261 show that fluorination shifts the spectra to the red, increases the absorbance extinction coefficient of dye-stained lipid vesicle suspensions and the intensity of fluorescence of stained cells measured using a confocal microscope, and increases the half time for bleaching of dye-stained cells.

TABLE 1

| Dye Designation | 1PF Abs. Max (nm) | 1PF Em. Max (nm) | 1PF Change (ΔF/F-100 mv); Ex/Em (nm) | SHG Change (%/50 mV) | 2PF Change (%, 615-665 nm/50 mV) | 2PF Change (%, 750-850 nm/50 m) | SHG Kinetics (ms) | Structure |
|---|---|---|---|---|---|---|---|---|
| di-4-ANEQPQ | 528 | 670 | 1.2E−001; 610/>665 | 3.84 ± 0.38 | 0.79 ± 0.37 | 5.03 ± 0.26 | 76 ± 13 | 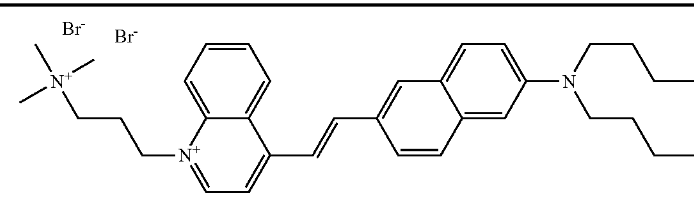 |
| di-4-ANBDQPQ | 539 | 708 | 2.0E−001; 618/>715 | 3.55 ± 0.55 | −6.61 ± 0.88 | 4.32 ± 0.57 | <5 | 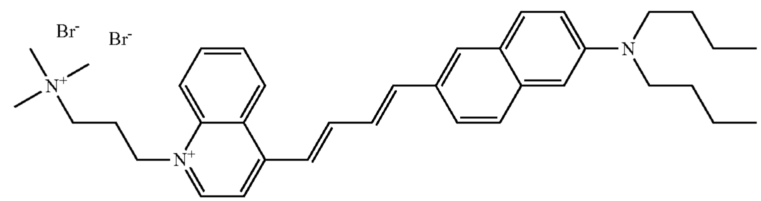 |
| di-4-ANHTQPQ | 504 | 655 | 5.4E−002; 630/>715 | 4.15 ± 0.28 | −7.51 ± 0.73 | 2.83 ± 0.45 | 34 ± 3 | 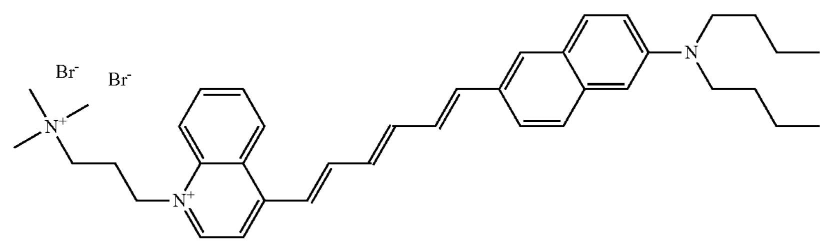 |
| PY-1261 | 547 | 686 | 5.0E−002; 625/>715 | 9.56 ± 0.42 | −2.57 ± 0.24 | 5.22 ± 0.28 | <5 | 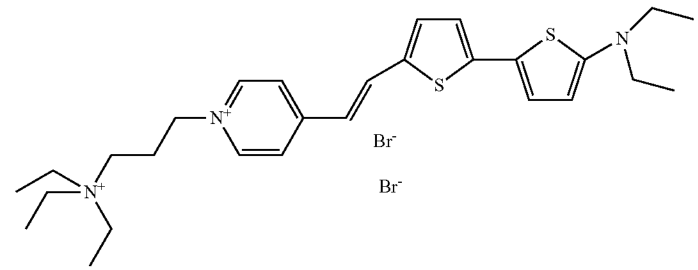 |

TABLE 1-continued
| Dye Designation | 1PF Abs. Max (nm) | 1PF Em. Max (nm) | 1PF Change (ΔF/F- 100 mV); Ex/Em (nm) | SHG Change (%/50 mV) | 2PF Change (%, 615- 665 nm/50 mV) | 2PF Change (%, 750- 850 nm/50 m) | SHG Kinetics (ms) | Structure |
|---|---|---|---|---|---|---|---|---|
| PY-1266 | 552 | 694 | 1.0E−001; 635/>715 | 3.75 ± 0.33 | −4.80 ± 0.53 | 2.25 ± 0.47 | 23 ± 2 | 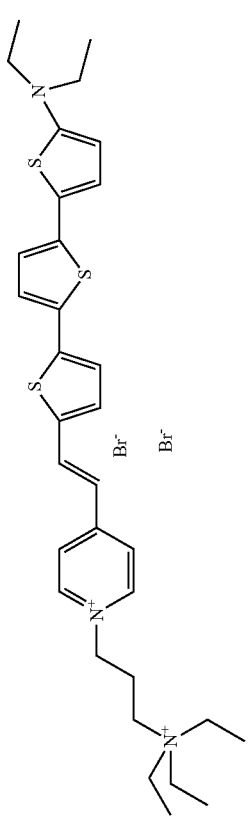 |
| PY-1268 | 535 | 714 | 4.2E−002; 640/>715 | 1.82 ± 0.18 | −16.64 ± 0.85 | −4.28 ± 0.54 | <5 | 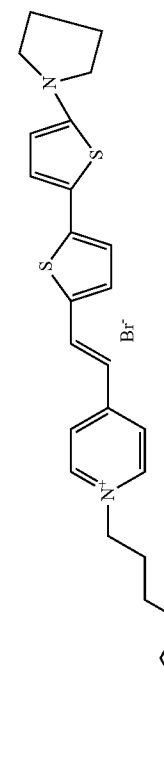 |
| PY-1274 | 551 | 691 | 5.0E−002; 620/>715 | 5.65 ± 0.45 | −4.20 ± 0.13 | 3.12 ± 0.18 | — | 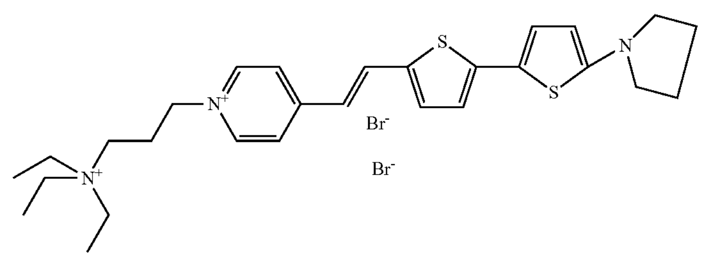 |

TABLE 1-continued

| Dye Designation | 1PF Abs. Max (nm) | 1PF Em. Max (nm) | 1PF Change (ΔF/F-100 mv); Ex/Em (nm) | SHG Change (%/50 mV) | 2PF Change (%, 615-665 nm/50 mV) | 2PF Change (%, 750-850 nm/50 m) | SHG Kinetics (ms) | Structure |
|---|---|---|---|---|---|---|---|---|
| PY-1278 | 555 | 688 | 7.9E-002; 640/>715 | 10.70 ± 0.59 | -3.86 ± 0.53 | 6.52 ± 0.76 | <5 | 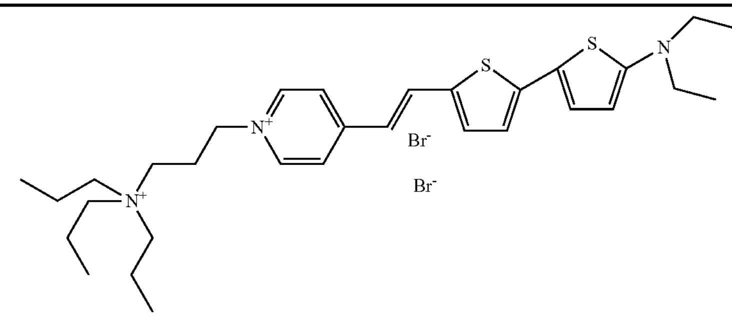 |
| PY-1280 | 547 | 690 | 1.1E-001; 640/>715 | 10.13 ± 0.88 | -6.12 ± 0.87 | 5.77 ± 1.22 | 109 ± 30 | 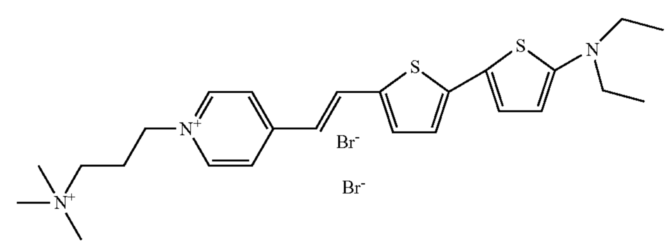 |
| PY-1282 | 530 | 676 | 8.0E-002; 640/>715 | 11.64 ± 0.60 | 0.29 ± 0.39 | 8.78 ± 1.08 | 16 ± 1 | 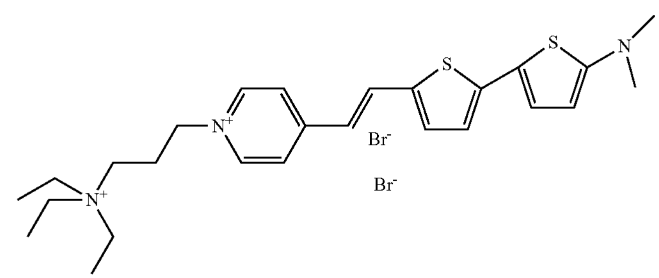 |

TABLE 1-continued

| Dye Designation | 1PF Abs. Max (nm) | 1PF Em. Max (nm) | 1PF Change (ΔF/F-100 mv); Ex/Em (nm) | SHG Change (%/50 mV) | 2PF Change (%, 615-665 nm/50 mV) | 2PF Change (%, 750-850 nm/50 m) | SHG Kinetics (ms) | Structure |
|---|---|---|---|---|---|---|---|---|
| PY-1284 | 536 | 588 | 1.5E-002; 555/>610 | 6.18 ± 0.68 | 6.72 ± 0.58 | — | — | 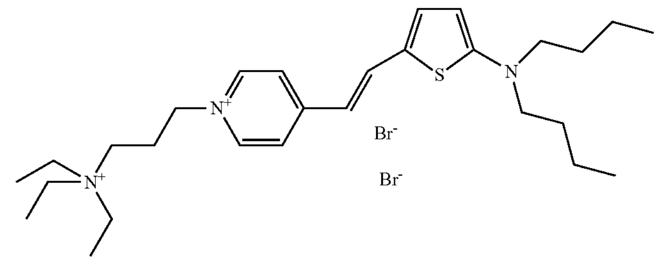 |
| PY-1286 | 547 | 692 | 1.8E-001; 640/>715 | 8.09 ± 0.42 | -5.65 ± 0.50 | 3.51 ± 0.66 | 27 ± 1 | 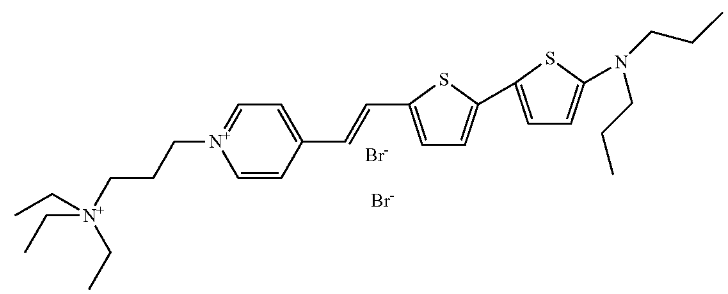 |
| PY-2240 | 704 | (FQY <0.001) | — | — | — | — | — | 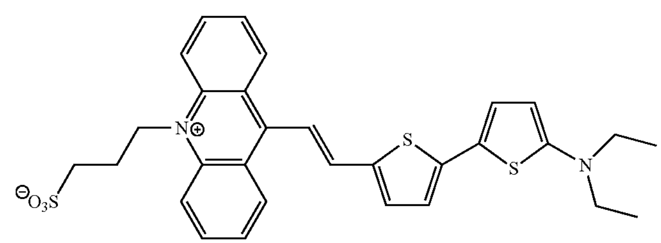 |

TABLE 1-continued
| Dye Designation | 1PF Abs. Max (nm) | 1PF Em. Max (nm) | 1PF Change (ΔF/F-100 mv); Ex/Em (nm) | SHG Change (%/50 mV) | 2PF Change (%, 615-665 nm/50 mV) | 2PF Change (%, 750-850 nm/50 m) | SHG Kinetics (ms) | Structure |
|---|---|---|---|---|---|---|---|---|
| PY-3008 | 565 | 706 | 1.0E-001; 650/>715 | — | — | — | — | 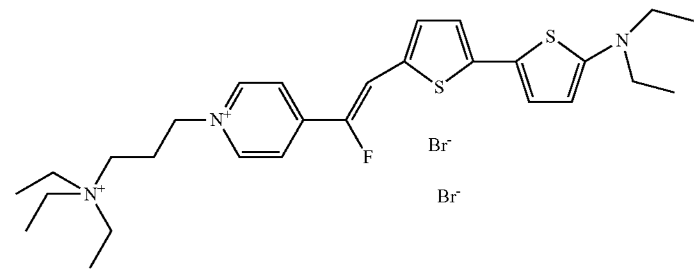 |

Imaging

For full details of our non-linear imaging microscope, we refer the reader to previously published descriptions. A. C. Millard, P. J. Campagnola, W. Mohler, A. Lewis, and L. M. Loew, "Second Harmonic Imaging Microscopy," *Meth. Enzymol.* 361, 47-69 (2003); Millard, A. C., L. Jin, and L. M. Loew, "Second Harmonic Generation Imaging Microscopy with a High Power Ultrafast Fiber Laser,"*Commercial and Biomedical Applications of Ultrafast Lasers.* 5714-5716, 92-98 (2005); A. C. Millard, L. Jin, M.-D. Wei, J. P. Wuskell, A. Lewis, and L. M. Loew, "Sensitivity of Second Harmonic Generation from Styryl Dyes to Transmembrane Potential," *Biophys. J.* 86, 1169-1176 (2004). Our current microscope combines a Fluoview (Olympus) scan-head and an Axiovert (Zeiss) inverted microscope constructed for multiple imaging methodologies including wide-field, one-photon excitation fluorescence imaging, as well as SHG and 2PF imaging. Our laser sources include a Mira (Coherent) Ti:sapphire laser and a Femtopower (Fianium) fiber laser operating at 1064 nm. Millard, A. C., L. Jin, and L. M. Loew, "Second Harmonic Generation Imaging Microscopy with a High Power Ultrafast Fiber Laser,"*Commercial and Biomedical Applications of Ultrafast Lasers.* 5714-5716, 92-98 (2005). For excitation, we routinely use an IR-Achroplan (Zeiss) 40×, 0.8 NA water-immersion objective though for shorter wavelengths we also use an A-Plan (Zeiss) 40×, 0.65 NA air objective. Fluorescence is imaged (for linear imaging) or collected (for non-linear imaging) back through the excitation objective, while SHG is collected in the forward, transmitted light direction by a condenser, either 0.8 NA or 0.55 NA (Zeiss). For optimal collection, the numerical aperture of the condenser should be at least $1/\sqrt{2}$ of the numerical aperture of the excitation objective (L. Moreaux, O. Sandre, S. Charpak, M. Blanchard-Desce, and J. Mertz, "Coherent Scattering in Multi-Harmonic Light Microscopy," *Biophys. J.* 80, 1568-1574 (2001); L. Moreaux, O. Sandre, and J. Mertz. "Membrane Imaging by Second Harmonic Generation Microscopy," *J. Opt. Soc. Am. B.* 17, 1685-1694 (2000)), though in practice a condenser of slightly lower numerical aperture will often suffice. Since the wavelength of second harmonic light is precisely half that of the excitation light, the choice of filter for SHG imaging is greatly simplified and the primary concern is the blocking of the excitation light that is also transmitted through the sample as well as fluorescence that is emitted forwards.

Cells

NIE-115 mouse neuroblastoma were cultured in DMEM with 10% fetal bovine serum and 1% antibiotic-antimycotic (Invitrogen, Carlsbad, Calif.) in a 60 mm plastic dish (353002, Becton Dickinson, Franklin Lakes, N.J.). The culture was maintained at 37° C. with 5% $CO_2$ for a period of 48 hours prior to experimentation.

For experimentation the growth medium was replaced with 3 mL of Earle's Balanced Salt Solution (EBSS, Sigma, St. Louis, Mo.) with 20 mM HEPES (Merck Biosciences AG, Laufelfingen, Switzerland). The internal buffer, injected into the patch pipette, was a potassium aspartate (140 mM, Sigma, St. Louis, Mo.), sodium chloride (5 mM, Sigma, St. Louis, Mo.) and HEPES (10 mM) solution at a pH of 7.35. The pH was adjusted with potassium hydroxide and hydrochloric acid.

Electrophysiology

For characterizing the voltage-sensitivity of SHG and 2PF, we used a slow (~0.1 Hz) switching protocol as previously described (A. C. Millard, P. J. Campagnola, W. Mohler, A. Lewis, and L. M. Loew, "Second Harmonic Imaging Microscopy," *Meth. Enzymol.* 361, 47-69 (2003); Millard, A. C., L. Jin, and L. M. Loew, "Second Harmonic Generation Imaging Microscopy with a High Power Ultrafast Fiber Laser," *Commercial and Biomedical Applications of Ultrafast Lasers.* 5714-5716, 92-98 (2005); A. C. Millard, L. Jin, M.-D. Wei, J. P. Wuskell, A. Lewis, and L. M. Loew, "Sensitivity of Second Harmonic Generation from Styryl Dyes to Transmembrane Potential," *Biophys. J.* 86, 1169-1176 (2004)) with a 50 mV step. For investigating the time-dependence of the voltage-sensitivity, we instead triggered a step waveform for the voltage-clamp approximately half-way through the page-scan; the protocol for determining signal time-dependence was previously described in detail. A. C. Millard, L. Jin, J. P. Wuskell, D. M. Boudreau, A. Lewis, and L. M. Loew, "Wavelength- and Time-Dependence of Potentiometric Non-linear Optical Signals from Styryl Dyes," *J. Membr. Biol.* 208, 103-111 (2005).

FIGS. 2A and 2B show SHG and 2PF images of the same neuroblastoma cell before differentiation. Filopodia, filamentous structures emanating from the round cell, can be seen clearly in the 2PF image, but are absent in the SHG image. This is because SHG requires a non-centrosymmetric distribution of harmonophores on the scale of the optical coherence length, and thus is unable to image highly symmetric or tiny structures like filopodia. The images of differentiated neuroblastoma cells, FIGS. 2C and 2D, illustrate another interesting phenomenon: internal membranes such as the endoplasmic reticulum are not imaged in SHG (2C) even when the dye has apparently been internalized to an extent that the 2PF contrast pattern is dominated by interior fluorescence (2D). This is particularly apparent in the color overlay image of FIG. 2E, where many of the neurites display red interiors from the 2PF channel and green peripheries from the SHG channel. This is because the highly convoluted fine structure of the endoplasmic reticulum has the effect of randomly orienting the dye molecules on the spatial scale of the optical coherence length. On the other hand, the monothiophene dyes generally show signals that are more than an order of magnitude lower. Examples of weak 2PF and SHG images of neuroblastoma cells stained with the monothiophene dye PY-1284 are provided in FIGS. 2E and 2F, respectively. The inferior nonlinear optical properties of the monothiophene series may be attributed to their different donor-acceptor distances.

Table 1 shows the data from one-photon, two-photon, and SHG experiments for all dyes studied in these series of experiments. The molecular structures are shown in the right-most column to illustrate the progressive alteration of certain chemical moieties, showing the effects on kinetics, signal sensitivity and absorption wavelength of different dye segments.

The left-most data columns of Table 1 are the absorption and emission maxima for one photon fluorescence in soybean multi-lamellar lipid vesicles used to mimic the membrane environment. The column indicating relative signal change for one-photon fluorescence also lists the excitation light source used and the lower bounds of the long-pass emission detected.

The remaining columns of Table 1 list the non-linear optical responses of the dyes to a 50 mV voltage change on a patch-clamped neuroblastoma cell. Excitation for both SHG and 2PF is at 1064 nm. The transmitted SHG signal was collected at 532 nm and the 2-photon excited emission was measured with 2 different wavelength bands as indicated in the Table 1 heading. We show that maximal SHG sensitivity is observed in PY-1282, at 11.7%/50 mV. The maximum 2PF sensitivities was observed in the tri-thiophene PY-1268 with a change of 16.6%/50 mV. This was the largest sensitivity observed for all dyes and imaging modalities.

Figure 3A:
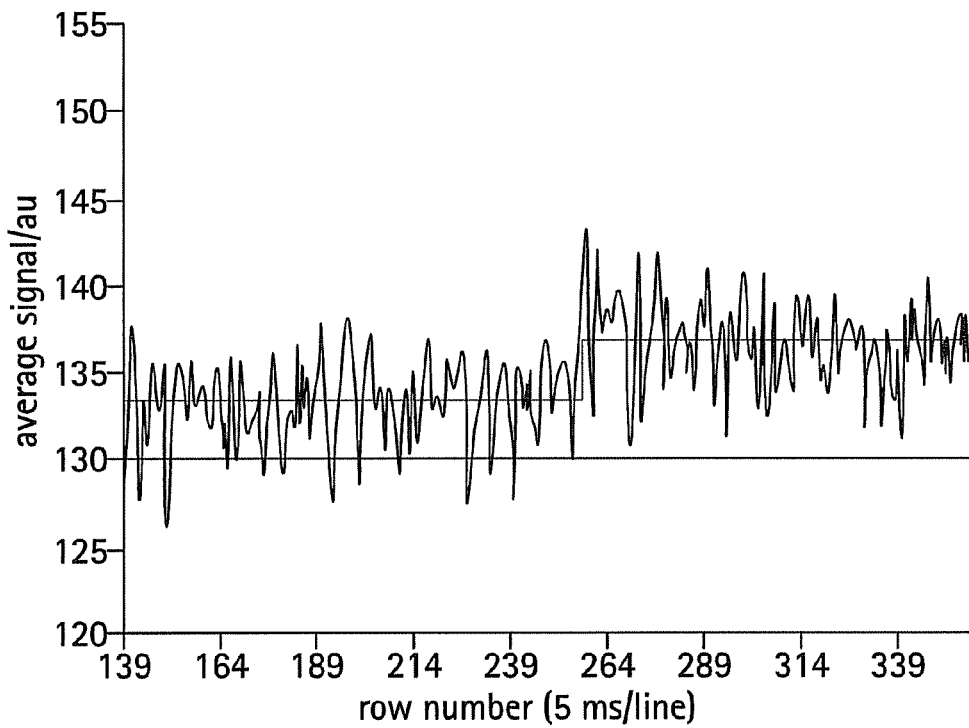
FIG. 3 presents kinetic data for PY-1268 showing the change in signal intensity at a location halfway through the page scan for a voltage switch of −50 mV: (a) SHG relative signal change; (b) 2PF relative signal change detected at 615-665 nanometers; (c) 2PF signal change detected at 750-850 nanometers.
Figure 3B:
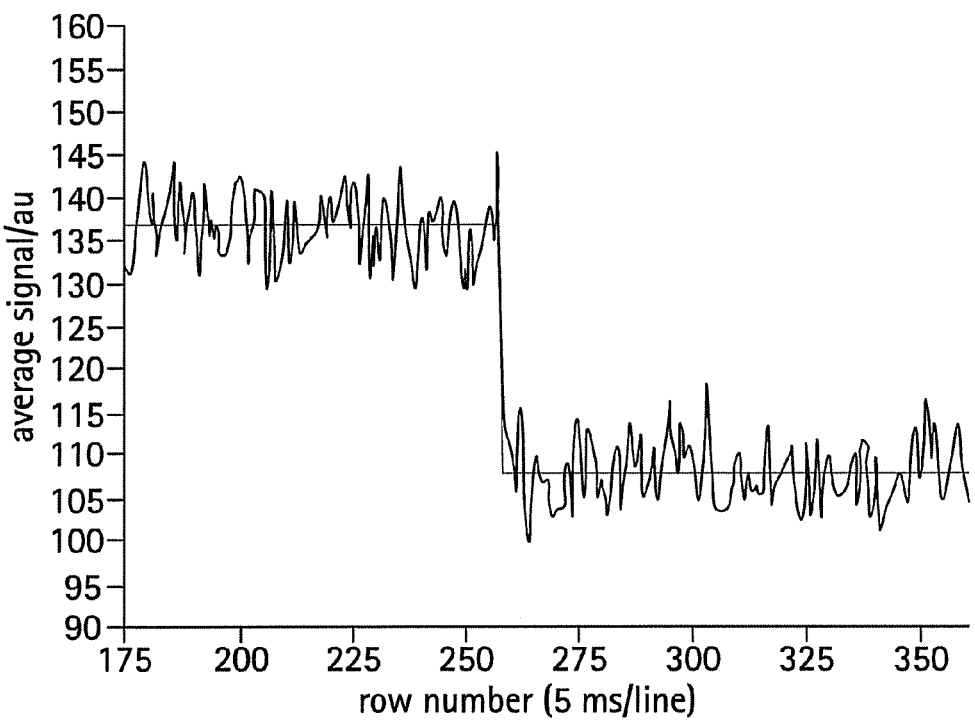
Figure 3C:
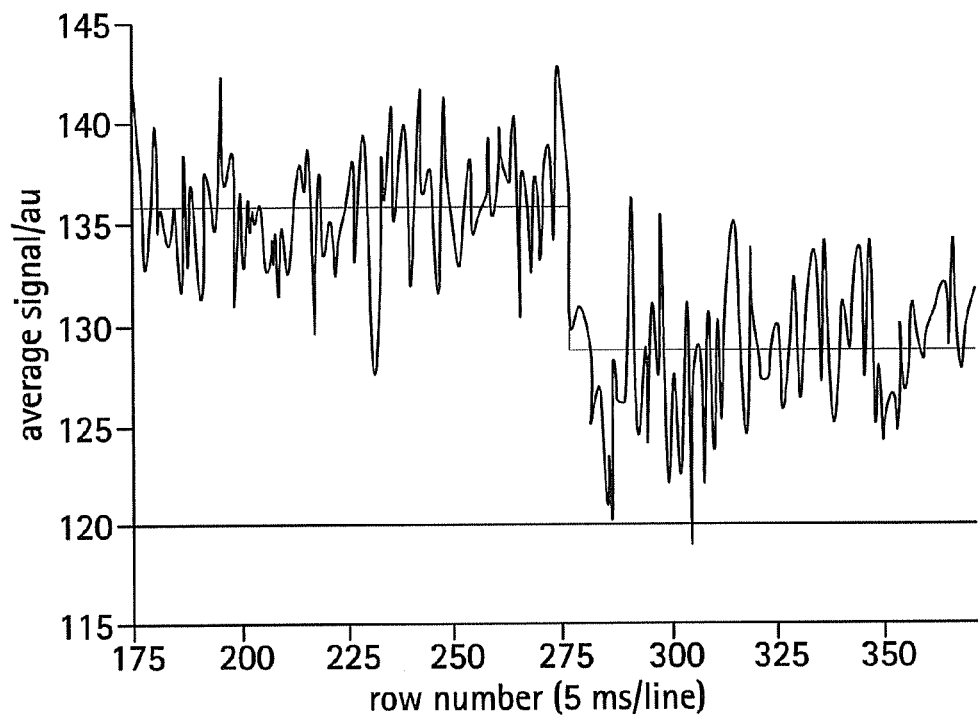

Importantly, 2PF changes were instantaneous, i.e., within the 5 ms time resolution of our measurements, for PY-1268 and all other dyes, while the SHG responses varied in their kinetics (right most column of Table 1). The kinetics data for SHG, 2PF detected between 615-665 nm, and 2PF detected between 750-850 nm for PY-1268 are shown in FIG. 3. Here, the SHG sensitivity per 50 mV is less than 2%, so the response to the voltage change, occurring at line number 254, is hard to distinguish from noise. However, the exponential fit to this data suggests that SHG occurs instantaneously. FIG. 3b shows signal change kinetics for 2PF detected over a range of emission wavelengths between 615 nm and 665 nm. This signal sensitivity is consistent with the data indicated in Table 1 (which were measured using a slow voltage clamp protocol) and indicates an instantaneous signal change. Curve fitting for this data set resulted in two zero-slope baselines before and after the signal change and a signal change that lasted less than one row (i.e., 5 ms) during the scan. The final graph here, FIG. 3c, shows a similar kinetics pattern for a smaller signal sensitivity of 4.28%/50 mV detected between 750-850 nm.

Figure 4A:
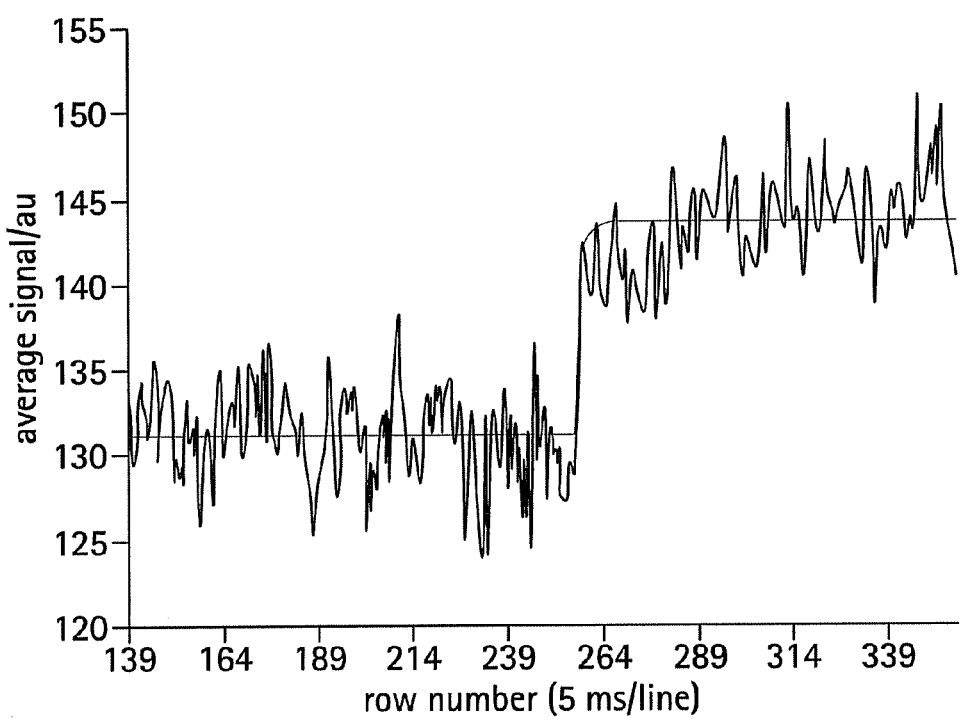
FIG. 4 presents kinetic data for PY-1261 showing the change in signal intensity at a location halfway through the page scan for a voltage switch of −50 mV: (a) SHG relative signal change; (b) 2PF relative signal change detected at 615-665 nanometers; (c) 2PF signal change detected at 750-850 nanometers.
Figure 4B:
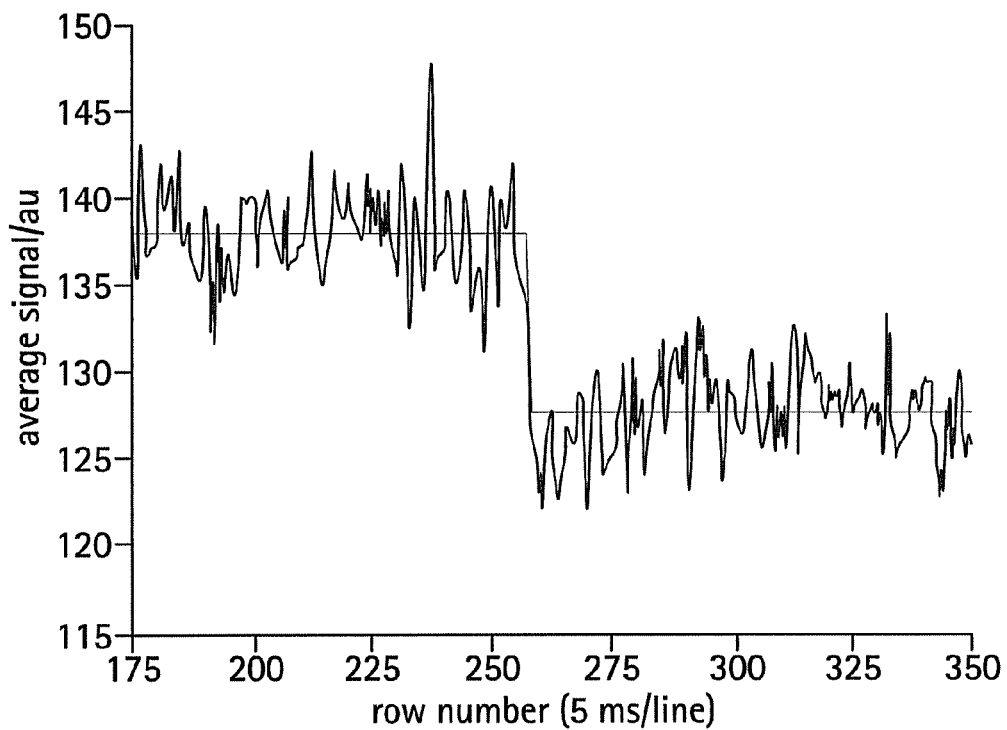
Figure 4C:
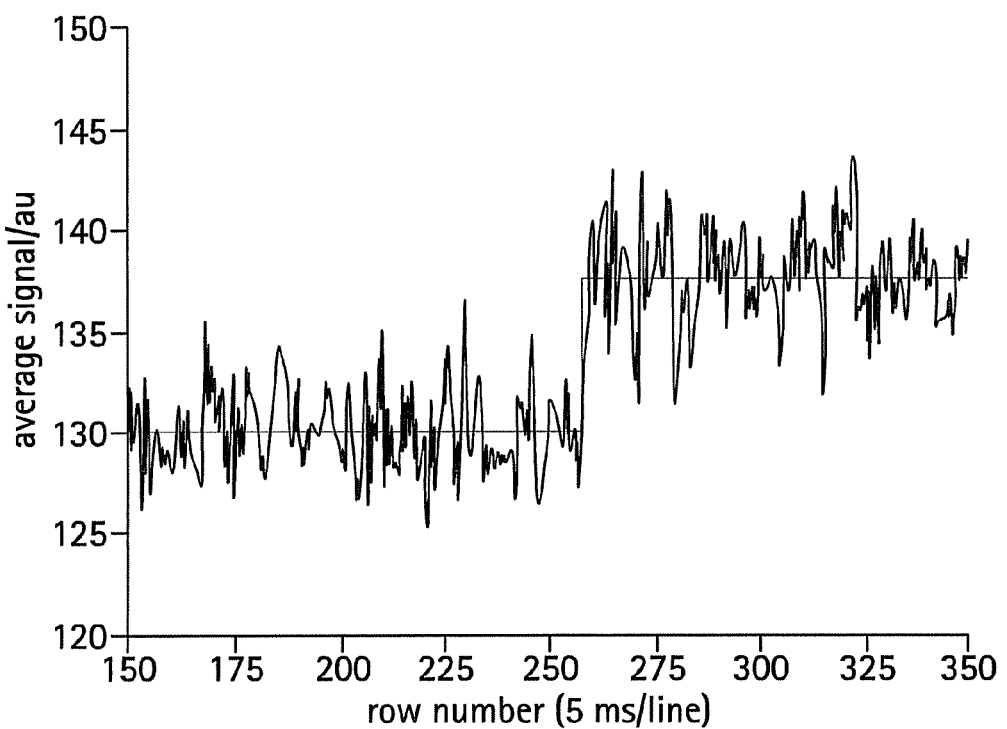

In contrast, the data for PY-1261 in FIG. 4 displays instantaneous kinetics for all imaging modalities, but with the largest signal sensitivity occurring in the SHG signal. This dye has a shorter chromophore than PY-1268, which is consistent with the relationship between their 2PF signal sensitivities. Interestingly, PY-1261 shows nearly a 10%/50 mV SHG signal change, which is more than five times larger than its tri-thiophene counterpart, but a maximum 2PF sensitivity that is close to three times smaller. Moreover, the larger 2PF change occurs in the wavelength range between 750-850 nm since PY-1261 exhibits a spectral shift toward the red. Dyes such as PY-1261 and PY-1278 are of particular interest since they have both instantaneous SHG kinetics and a large, close to 10%/50 mV signal sensitivity.

Figure 5:
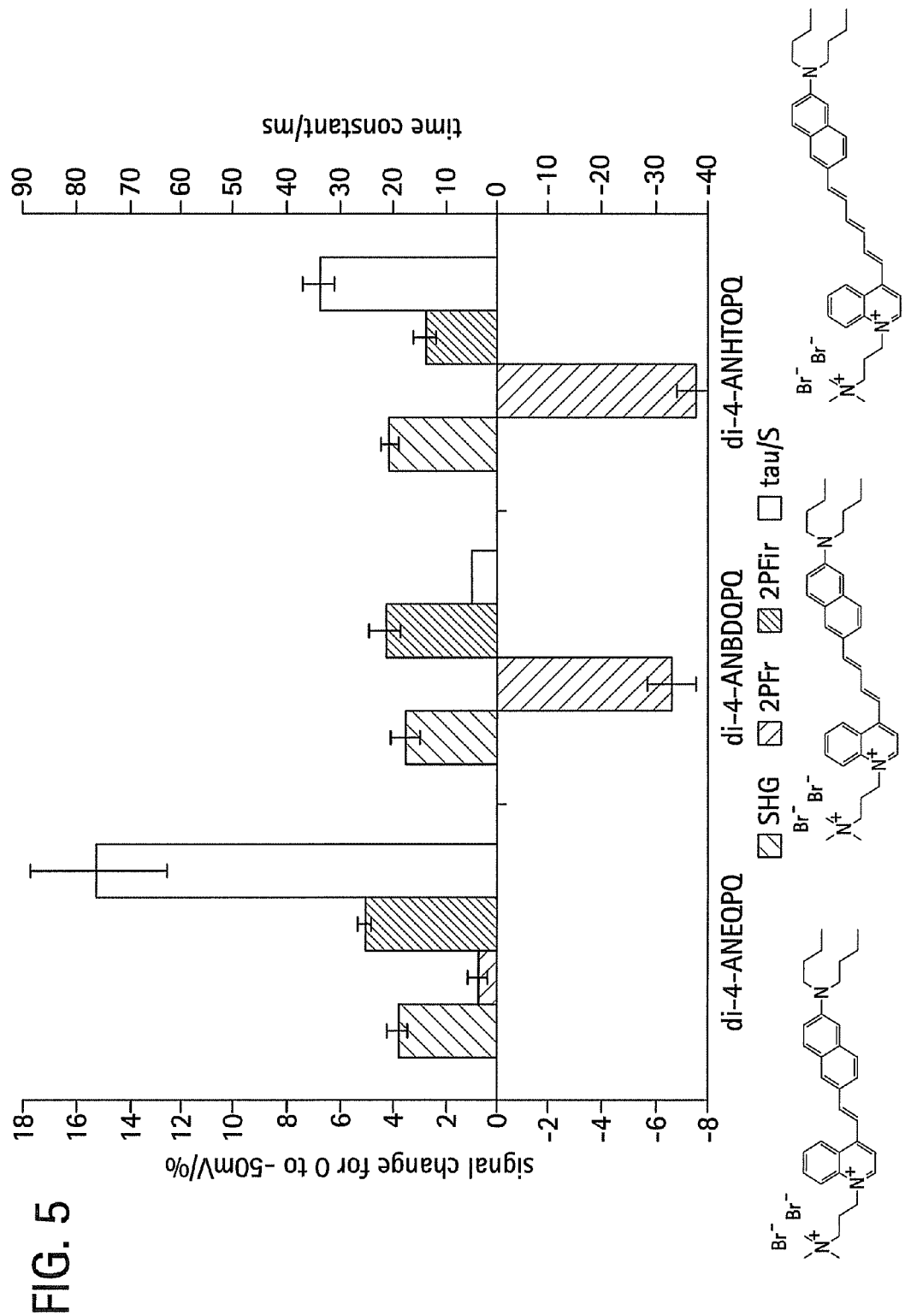
FIG. 5 is a comparison chart showing both signal sensitivities for SHG and 2PF and SHG kinetic response for a QPQ dye series. The left vertical axis shows percentage for signal sensitivity and the right vertical axis shows kinetics in milliseconds, represented by the last bar of each series.

The dyes in Table 1 were designed to allow comparison of the voltage-dependent non-linear responses as a function of specific molecular features. FIG. 5 shows the results obtained from altering the number of double bonds in the chromophore in the quinolinium propyl trimethylammonium series. The two vertical axes show both the non-linear signal sensitivity to a 50 mV switch, as well as the SHG signal kinetics to a 75 mV switch. The latter is indicated by the time constant, $\tau$, as the gray bar on the graph. It should be emphasized that the signal speed for the 2PF responses of all the dyes are all as fast as our measurement allows, <5 ms. These data show that while the SHG sensitivity is the same for all dyes within a margin of error, the signal speed is different for the different chromophores. Specifically, optimal dye kinetics occurs with the two double-bond dye, di-4-ANBDQPQ. The amount of time for the dye to react to a given voltage switch is prolonged in the case of the three double-bond di-4-ANHTQPQ, illustrated in the last data set. Interestingly, the time for the smallest molecule, di-4-ANEQPQ, to react to voltage is the longest. Lastly, there is a distinguishable spectral shift exhibited by the longer chromophore dyes when compared to di-4-ANEQPQ. This is most noticeable in the range of wavelengths between 615-665 nm, labeled 2PFr in the graph. While di-4-ANEQPQ exhibits a positive signal change in both the 615-665 nm and the 750-850 nm ranges of wavelengths, the two longer dyes exhibit a spectral shift as evidenced by the larger negative signal sensitivity in the 615-665 nm range of wavelengths. The larger signal sensitivity is consistent with the idea that a longer chromophore should show a more significant electrochromic effect. This is because the positive charge redistribution upon transition to the excited state from the quinolinium to the naphthyl amine moieties has a greater distance to traverse and therefore is more sensitive to the intra-membrane electric field. However, we did not attempt to systematically scan the excitation and emission wavelengths to try to determine the maximal electrochromic effect for these dyes.

Figure 6:
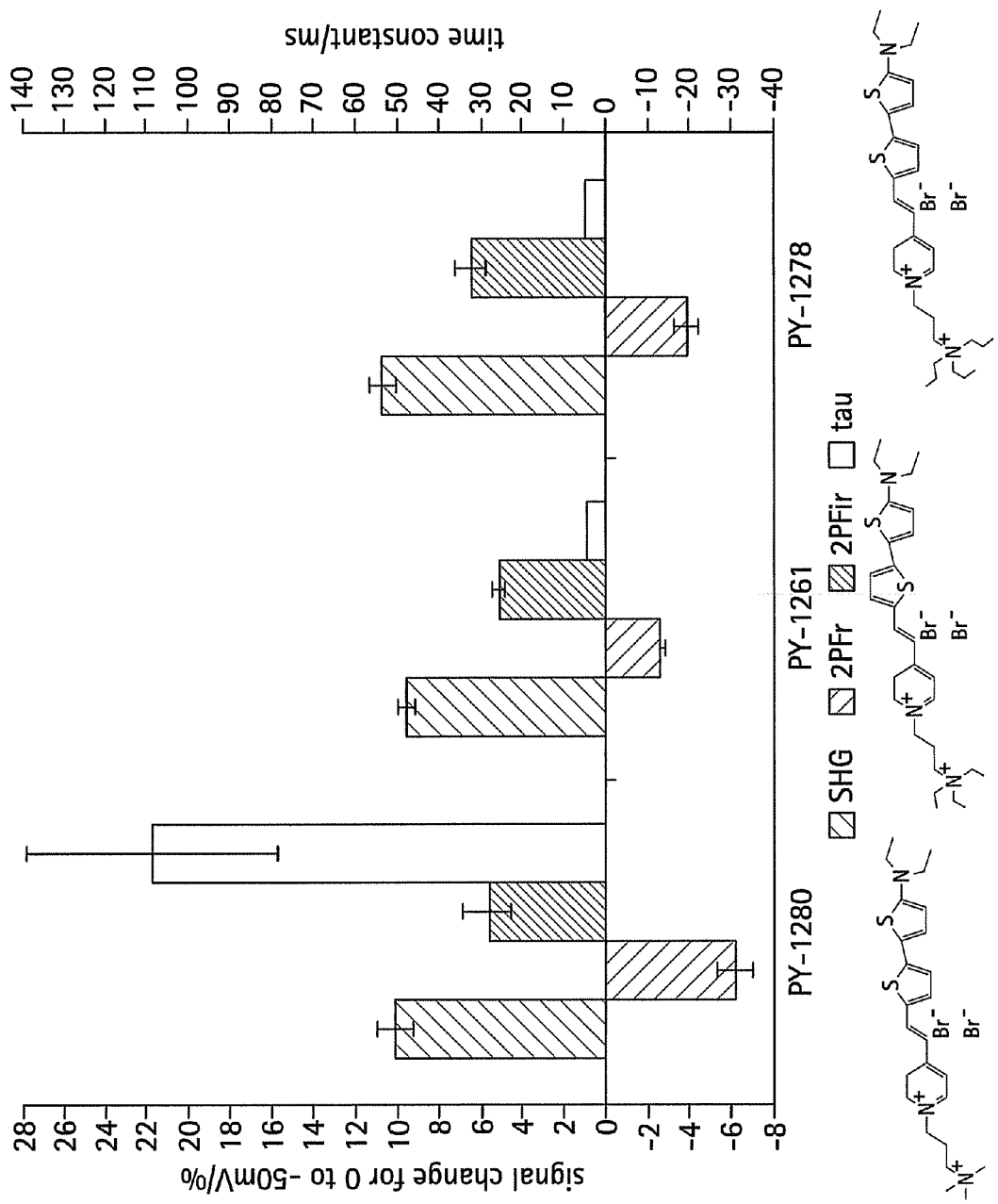
FIG. 6 is a comparison chart showing both signal sensitivities for SHG and 2PF and SHG kinetic response for head group variation. The left vertical axis shows percentage for signal sensitivity and the right vertical axis shows kinetics in milliseconds, represented by the last bar of each series.

FIG. 6 compares results for a set of three dyes in which the head group changes. The most significant of the results here is that of the dye on the leftmost portion of the graph, PY-1280, showing a significantly slower signal response to a change in voltage. It is important to note that both PY-1261 and PY-1278 have a "fast" kinetic response, which in FIG. 6 is illustrated as being less than or equal to 5 ms, the temporal resolution of these experiments.

The remaining variable in the dye synthesis permutations is the length of the two hydrocarbon chains in the hydrophobic tail of the dye molecules; this is shown in FIG. 7. These data show a significant decrease in both SHG and 2PFir signal sensitivity with increasing tail length. In both cases, the largest signal sensitivity is observed with the one-carbon head group, PY-1282. The signal decreases with each added pair of carbons. In this set of dyes, PY-1261 and PY-1278 have an "instantaneous" SHG voltage switch, depicted by the smallest experimental time unit of 5 ms. Increasing the head group length beyond four carbons per tail slows the kinetics to the point that the data can be fit with an exponential; the time constant, $\tau$, of this exponential is shown on the graph.

Discussion

The data presented here show the results of a systematic screening of new non-linear optical dyes designed to respond to membrane potential. Both dye kinetics and average signal change to TMP are presented. We searched for an optimal combination of "speed and sensitivity" to identify the ideal dye for monitoring cellular membrane electrical activity. Several such dyes tested satisfy this description. Moreover, a methodical alteration of chemical moieties, such as that described in this work, can further elucidate the molecular mechanism by which these potentiometric dyes respond to voltage.

A total of fourteen dyes were tested for 2PF/SHG sensitivity and kinetics, as well as one-photon absorption and emission peaks and sensitivity. The dyes were grouped according to common chemical characteristics; the results between common dye variations were compared. All data acquired in these series of experiments are shown in Table 1. Though kinetics for both 2PF and SHG were tested, the former is consistently instantaneous across all dyes within a temporal resolution of <5 ms. However, the SHG response to TMP is not always instantaneous. FIGS. 3 and 4 highlight two dyes with strong intensities indicating heavy staining levels, showing large signal changes as well as fast kinetics. PY-1261 in FIG. 4a shows one of the first thiophene-based potentiometric dyes synthesized in our laboratory with nearly a 10%/50 mV SHG change and instantaneous kinetics. PY-1268 shows a similarly instantaneous SHG change, albeit with a much lower amplitude, but a more remarkable result is its 2PF sensitivity. It has generally been presumed that SHG signal sensitivity would be larger given the same change in voltage than 2PF, but our data show a nearly 17%/50 mV change in PY-1268 2PF. Considering that this change occurs quickly and given the abundance of 2PF detection systems, PY-1268 is a prime candidate for physiological applications requiring the ability to detect action potentials. For comparison, previously published data on the SHG kinetics of di-4-ANEPPS show a slow response to the same voltage change, which occurred with an exponential time constant of 70.6 ms. A. C. Millard, L. Jin, J. P. Wuskell, D. M. Boudreau, A. Lewis, and L. M. Loew, "Wavelength- and Time-Dependence of Potentiometric Non-linear Optical Signals from Styryl Dyes," *J.*

*Membr. Biol.* 208, 103-111 (2005). FM4-64 shows a SHG change that is fast but the response is <10%/100 mV (D. A. Dombeck, L. Sacconi, M. Blanchard-Desce, and W. W. Webb. "Optical recording of fast neuronal membrane potential transients in acute mammalian brain slices by second-harmonic generation microscopy." *J Neurophysiol.* 94, 3628-3636 (2005); M. Nuriya, J. Jiang, B. Nemet, K. B. Eisenthal, and R. Yuste, "Imaging membrane potential in dendritic spines," *PNAS* 103, 786-790 (2006). We have not yet tested the linearity of the voltage-dependent responses of our dyes, but the SHG of PY-1261 and the 2PF of PY-1268 already show greater rapid responses to a 50 mV potential step than is observed for the FM4-64 SHG response to 100 mV.

The chromophore variations are shown in the QPQ dye series (FIG. 5). Here, the length of chromophore does not profoundly alter the maximum signal sensitivity. The average absolute SHG signal sensitivity for this dye series is 3.76%/50 mV and the average maximal absolute 2PF signal sensitivity is 6.69%/50 mV. Deviations all range within 2% of the mean. The most significant result seen here is the SHG kinetics of di-4-ANBDQPTMA. While the maximal signal sensitivity of this dye is essentially identical to the other two, its kinetic curve statistically resembles a fluorescence responses of voltage-sensitive dyes. L. M. Loew, "How to choose a potentiometric membrane probe", in "Spectroscopic Membrane Probes," L. M. Loew, Ed., pp. 139-152, CRC Press, Boca Raton (1988). A probe with a longer hydrophobic tail will bind to the membrane more strongly and rigidly than probes with shorter tails. If the signal change results from an on-off or reorientation mechanism then the hydrophobic dyes will be less likely to exhibit a large change. This theory is supported by the kinetics data shown in FIG. 7, where the more hydrophobic head groups of PY-1266 and PY-1286 display a slower kinetic response. Importantly, the fluorescence kinetics of all of these dyes were fast (<5 ms), suggesting that the mechanisms for the fluorescence responses to membrane potential changes are different from the mechanisms of the SHG responses.

The rapid responses to voltage clamp steps of all the dyes in both SHG and 2PF modalities argue against these responses being due to a change in membrane composition or a change in their intracellular location. These dyes are very sensitive to their environment and are likely to be excellent reporters of lipid composition. However, changes in lipid composition occur from processes such as endocytosis, exocytosis or lipid trafficking, which are on the on timescales of many seconds to minutes. Thus the millisecond response times of the dyes are most likely a reflection of the rapid change in transmembrane potential.

Absorption and emission spectra were obtained for a series of dyes with different acceptors: pyridinium (PY-1261), quinolinium (PY-212), and acridinium (PY-2240). For each additional fused benzo ring, there is ~75 nm red-shift in both absorption and emission spectra, but there is also a successive drop in fluorescence quantum yield, with acridinium salt PY-2240 being not detectably fluorescent.

Our data suggest that the mechanism behind SHG signal sensitivity may not be purely electrochromic, that is, dependent only on the electronic interaction of the dye chromophore with the electric field, but may additionally involve some very local voltage-dependent change in how the dye orients in or associates with the membrane. Moreover, this work also shows that we are able to synthesize a series of dyes excitable at 1064 nm, exploiting the utility of turnkey relatively inexpensive fiber-based femtosecond lasers. Several of these dyes respond quickly to voltage change, with large signal sensitivity to TMP without any apparent effects on cellular activity. PY-1261 and PY-1278 exhibit both a large SHG signal change and instantaneous kinetics. PY-1268 shows a large and instantaneous 2PF signal change in a visible emission band. These dyes thus significantly enhance and expand the range of optical approaches available to experimentalist interested in mapping electrical activity in complex excitable cells and tissue. Importantly, the availability of a choice of dyes will allow investigators to choose probes not only based on sensitivity to voltage but also on such additional factors as solubility, excitation and emission wavelengths, tissue penetration, staining persistence and resistance to cell internalization.

Action Potential Dynamics Experiments

Dyes

Structures of dyes used in these experiments are shown in Table 2. Synthesis of the amino(oligo)thiophene dyes is described above. Other voltage-sensitive dyes were synthesized according to the aldol condensation and palladium-catalyzed coupling strategies described in A. Hassner, D. Birnbaum, L. M. Loew "Charge Shift Probes of Membrane Potential. Synthesis", J. Org. Chem. 49, 2546-2551 (1984); S. Antic, L. M. Loew, J. P. Wuskell, D. Zecevic, "Voltage-sensitive Dyes for Intracellular Application", Biol. Bull. 183, 350-351 (1992); and J. P. Wuskell, D. Boudreau, M. D. Wei, L. Jin, R. Engl, R. Chebolu, A. Bullen, K. D. Hoffacker, J. Kerimo, L. B. Cohen, M. R. Zochowski, L. M. Loew "Synthesis, spectra, delivery and potentiometric responses of new styryl dyes with extended spectral ranges" J. Neurosci. Methods, 151, 200-215 (2006).

TABLE 2

Chemical and physical characteristics of red and blue voltage-sensitive dyes used in present study

| Dye | Red JPW-3028 | Blue JPW-3080 |
|---|---|---|
| Chemical structure | | |
| Molecular formula | $C_{24}H_{31}Br_2N_3$ | $C_{31}H_{37}Br_2N_3O$ |
| Descriptive name | Di-1-ANEPEQ | Di-1-APEFEQPQ |
| Molecular weight | 521.34 | 627.47 |
| Absorbance MLV (nm) | 457 | 569 |
| Emission MLV (nm) | 670 | 730 |
| Absorbance water (nm) | 440 | 554 |
| Emission water (nm) | NDA | NDA |
| Absorbance ethanol (nm) | 511 | 630 |
| Emission ethanol (nm) | 718 | 896 |
| Dye | Blue JPW-6003 | Blue JPW-4090 |
| Chemical structure | | |
| Molecular formula | $C_{37}H_{49}Br_2N_3$ | $C_{33}H_{41}Br_2N_3$ |
| Descriptive name | Di-4-ANBDQPQ | Di-2-ANBDQPQ |
| Molecular weight | 695.63 | 639.52 |
| Absorbance MLV (nm) | 539 | 526 |
| Emission MLV (nm) | 708 | 702 |
| Absorbance water (nm) | 552 | 490 |
| Emission water (nm) | NDA | NDA |

TABLE 2-continued

Chemical and physical characteristics of red and blue voltage-sensitive dyes used in present study

| | | |
|---|---|---|
| Absorbance ethanol (nm) | 603 | 584 |
| Emission ethanol (nm) | 818 | 812 |
| Dye | Blue PY-1261 | Blue PY1268 |
| Chemical structure | | |
| Molecular formula | C$_{28}$H$_{41}$Br$_2$N$_3$S$_2$ | C$_{32}$H$_{43}$Br$_2$N$_3$S$_3$ |
| Descriptive name | Di-2-BTEPPTEA | Di-2-TTEPPTEA |
| Molecular weight | 643.60 | 725.72 |
| Absorbance MLV (nm) | 547 | 535 |
| Emission MLV (nm) | 686 | 714 |
| Absorbance water (nm) | 539 | 508 |
| Emission water (nm) | NDA | NDA |
| Absorbance ethanol (nm) | 614 | 588 |
| Emission ethanol (nm) | NDA | NDA |
| Dye | Blue PY-1286 | Blue PY-1266[a] |
| Chemical structure | | |
| Molecular formula | C$_{30}$H$_{45}$Br$_2$N$_3$S$_2$ | C$_{32}$H$_{49}$Br$_2$N$_3$S$_2$ |
| Descriptive name | Di-3-BTEPPTEA | Di-4-BTEPPTEA |

TABLE 2-continued

Chemical and physical characteristics of red and blue voltage-sensitive dyes used in present study

| | | |
|---|---|---|
| Molecular weight | 671.65 | 699.70 |
| Absorbance MLV (nm) | 547 | 552 |
| Emission MLV (nm) | 692 | 694 |
| Absorbance water (nm) | 567 | 555 |
| Emission water (nm) | NDA | NDA |
| Absorbance ethanol (nm) | 616 | 624 |
| Emission ethanol (nm) | NDA | NDA |

[a]PY-1266 was in the form of a gamma-cyclodextrin complex (J. P. Wuskell, D. Boudreau, M. D. Wei, L. Jin, R. Engl, R. Chebolu, A. Bullen, K. D. Hoffacker, J. Kerimo, L. B. Cohen, M. R. Zochowski, L. M. Loew, "Synthesis, spectra, delivery and potentiometric responses of new styryl dyes with extended spectral ranges", J. Neurosci. Methods 151, 200–215 (2006)).
NDA: no data available.

Brain Slice and Electrophysiology

Sprague Dawley rats (P21-42) were anesthetized with isoflurane, decapitated, and the brains were removed with the head immersed in ice-cold, artificial cerebrospinal fluid (ACSF), according to an animal protocol approved by the Center for Laboratory Animal Care, University of Connecticut. Brain slices (300 μm) were cut from frontal lobes in the coronal plane. ACSF contained (in mM) 125 NaCl, 26 $NaHCO_3$, 10 glucose, 2.3 KCl, 1.26 $KH_2PO_4$, 2 $CaCl_2$ and 1 $MgSO_4$, pH 7.4. Whole-cell recordings were made from visually identified layer V pyramidal neurons on the medial part of the slice. Intracellular solution contained (in mM) 135 K-gluconate, 2 $MgCl_2$, 3 $Na_2$-ATP, 10 $Na_2$-phosphocreatine, 0.3 $Na_2$-GTP and 10 Hepes (pH 7.3, adjusted with KOH). Electrical signals were amplified with Multiclamp 700A and digitized with two input boards: (1) Digidata Series 1322A (Axon Instruments) at 5 kHz, and (2) Neuroplex (RedShirtImaging) at 2.7 kHz sampling rate. Only cells with a membrane potential more hyperpolarized than −50 mV, and action potential amplitudes exceeding 80 mV (measured from the base line) were included in this study. All experiments were performed on layer 5 cortical pyramidal cells at 34° C.

Dye Injections

The dye injection protocol was based on our previous work with red dyes (JPW-1114 and JPW-3028; S. D. Antic, "Action potentials in basal and oblique dendrites of rat neocortical pyramidal neurons", *Journal of Physiology,* 550, 35-50 (2003)). Neurons were filled through whole-cell recording pipettes with voltage-sensitive dyes listed in Table 2. Blue dyes were stored in ethanol stock solution at −20° C. On the day of the recording blue dyes were dissolved in standard K-gluconate based intracellular solution. A loading pipette was filled with two varieties of the same intracellular solution; one with and one without dye. Dye-free solution was occupying the very tip of the pipette, while the back of the pipette lumen was microloaded with dye-rich solution. The purpose of dye-free solution in the tip of the patch pipette was to prevent dye-leak during the maneuver through brain slice tissue. VSD styryl dyes are lipophilic and bind indiscriminately and irreversibly to all membranes around the neuron of interest. Even a small amount of dye that leaks out of the pipette during the formation of the gigaohm seal, can generate strong fluorescent background. Fluorescent light emanating from surrounding tissue has a devastating effect on dendritic optical signals. Elimination of the background fluorescence is critical for dendritic voltage imaging. How much dye-free solution one should put in the tip depends on time period between the submersion of the patch pipette into the recording chamber and formation of the gigaohm seal. The faster one can perform this maneuver the less dye-free solution she needs to achieve optimal staining.

Blue VSD were injected at room temperature for 25-60 minutes. The filling pipette was carefully pulled out (outside-out patch) and brain slices were left to incubate for 20-120 minutes at room temperature. Just before optical recordings the cells were re-patched with dye-free pipette at the physiological temperature (34° C.).

Optical Measurements

Voltage-sensitive dye imaging was performed on a Zeiss Axioskope 2FS microscope equipped with NeuroCCD camera (RedShirtImaging). We used Zeiss 40× objective IR-Achroplan 0.80 W. The size of the square visual field captured by NeuroCCD camera was 384×384 um. In the place of the arc lamp (normally used for epi-illumination), we inserted a 200 μm fiber optic guide with a collimator. Laser beam was focused on the other side of the fiber optic guide using a microscope objective-like lens. This arrangement produced a motionless spot of laser light (~25 μm in diameter) at the object plane. An illuminated section of the brain slice, projected onto the NeuroCCD camera, covered approximately 25 pixels when used with 40× objective lens. At this magnification, one pixel sampled a 4.8×4.8 square in the object plane. A region of interest (ROI) was brought into the laser spot using X-Y microscope platform. The laser beam was interrupted by an electro-programmable shutter (Uniblitz®). Attention was made to limit the exposure time during the recording and positioning of the neuron. Focusing and positioning was done at lower light level intensities—regulated by neutral density filters. In the course of this experimental study we used three different laser light sources, Cobolt Samba (100 mW), HeNe (20 mW), and laser diode (80 mW), with peak excitations centered at 532, 633, and 658 nm, respectively. Laser beams were directed onto the preparation with the help of Zeiss epi-illumination filter cubes. For 532 nm laser epi-illumination we used a filter cube with a following set of optical filters: exciter 520±45 nm; dichroic 570 nm; emission >610 nm. For 633 nm laser epi-illumination we used exciter 640/30 nm, dichroic 660 nm and emission 665 nm long-pass. For 658 nm laser epi-illumination we used 700 nm dichroic, and 720 nm emission filter (no exciter).

Optical signals were recorded with 80×80 pixels at a 2.7 kHz frame rate, stored, and then temporally filtered (off-line) with digital Gaussian low-pass filter (1050 Hz cut-off), and Butterworth high-pass (4.5 Hz), unless otherwise specified. To correct for photobleaching artifact the trace without stimulus was recorded at the end of experiment and subtracted from physiological recordings. The term ROI (region of interest) we use to mark selected neuronal compartments, where membrane potential transients were measured either optically (voltage-sensitive dyes) or electrically (whole-cell). To improve signal-to-noise ratio multiple pixels (3-6 pixels) were selected inside the region of interest and spatially averaged, unless otherwise specified.

After the experiment, brain slices were mounted on a microscope slide and photographs were taken with Zeiss AxioVision system. All recovered neurons (n=73) had typical pyramidal morphology with thick apical dendrites projecting vertically towards the pia. The apical trunk bifurcation occurred high in layers III and II, giving rise to 2-3 apical tuft branches that run almost parallel to pia.

Data Analysis

Optical and electrical measurements were analyzed using the software Neuroplex 8.3.2 (RedShirtImaging) and Clampfit 9.1 (Axon Instruments). Graph plotting was done in Excel. Amplitudes of action potentials in axons and dendrites (optical signals) were measured from the base line and expressed as a fractional change in light intensity ($\Delta F/F$). Intracellular voltage-sensitive dyes cannot be used to determine the absolute amplitude (in mV) of the electrical transients in distal dendritic segments. S. Antic, G. Major, D. Zecevic, "Fast optical recordings of membrane potential changes from dendrites of pyramidal neurons", Journal of Neurophysiology 82, 1615-1621 (1999).

Results—Experiments on Spherical Lipid Bilayers

Previous work with internally applied VSD has identified naphthylstyryl moiety as the moiety of choice for experiments on individual CNS neurons in brain slices. S. Antic, G. Major, D. Zecevic, "Fast optical recordings of membrane potential changes from dendrites of pyramidal neurons", Journal of Neurophysiology 82, 1615□ 1621 (1999). A primary goal of the present work was to extend the wavelength range of the styryl chromophores, while preserving the electrochromic sensitivity of the dyes to rapid changes in membrane potential. In addition, the lipophilicity of new molecules must not increase and compromise their intracellular application and the rate of diffusion in the dendritic tree. Accordingly, we sought to preserve the general structural organization of the styryl chromophores. The strategy was to shift their spectra to longer wavelengths by extending the conjugation with longer linkers, larger nitrogen heterocycle acceptors, and more highly constrained planar donors. J. P. Wuskell, D. Boudreau, M. D. Wei, L. Jin, R. Engl, R. Chebolu, A. Bullen, K. D. Hoffacker, J. Kerimo, L. B. Cohen, M. R. Zochowski, L. M. Loew "Synthesis, spectra, delivery and potentiometric responses of new styryl dyes with extended spectral ranges", *J. Neurosci. Methods,* 151, 200-215 (2006). Newly synthesized organic compounds have bluish appearance in organic solvents, and hence are dubbed "blue dyes". The optimal excitation wavelengths for optical recording of the blue dyes was red-shifted by approximately 150 nm; from ~520 nm (red dyes) to ~660 nm (blue dyes). In spherical bilayers the blue VSDs generated potentiometric responses, which were often larger in amplitude than those recorded with red VSD (~15% compare to ~10% ΔF/F). Although very promising, these results gave no guarantee that blue dyes would be useful for voltage imaging of real neurons in semi-intact preparation, such as brain slice. Intracellular staining of individual neurons in situ is considerably more difficult than extracellular staining of lipid spheres suspended in solution. In addition, it has been noticed previously that performance of the same VSD varies considerably in different biological preparations. For instance the same dye (oxonol) shows good signals in barnacles and leech but minimal signals in chick spinal cord neurons, or rat superior cervical ganglion neurons. W. N. Ross, L. F. Reichardt, "Species-Specific Effects on the Optical Signals of Voltage-Sensitive Dyes", *Journal of Membrane Biology,* 48, 343-356 (1979). The only way to evaluate the applicability of new voltage-sensitive dyes for a given projects is to carry out methodical tests in the preparation of choice. L. B. Cohen, S. Lesher, "Optical monitoring of membrane potential: methods of multisite optical measurement", *Society of General Physiologists*, Series 40, 71-99 (1986). Here we present results of testing performed with seven newly synthesized molecules carried out on pyramidal cells in acute cortical brain slice.

Figure 1D:
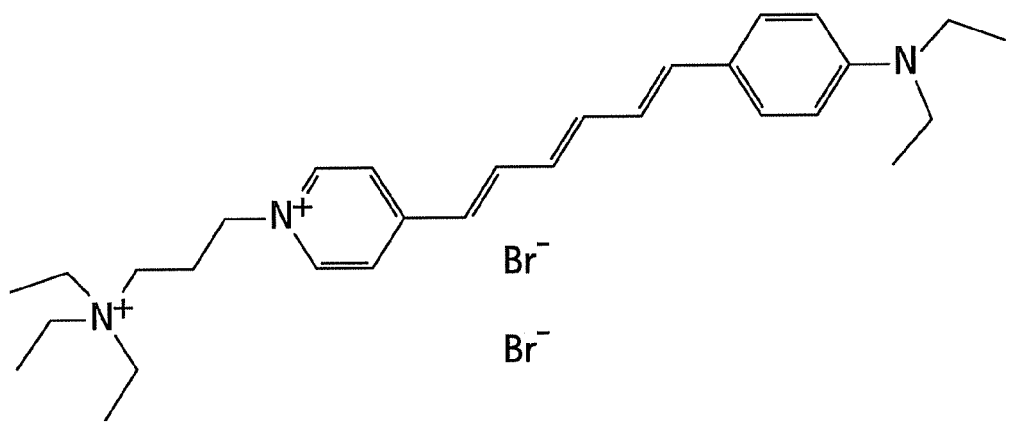
Figure 8D:
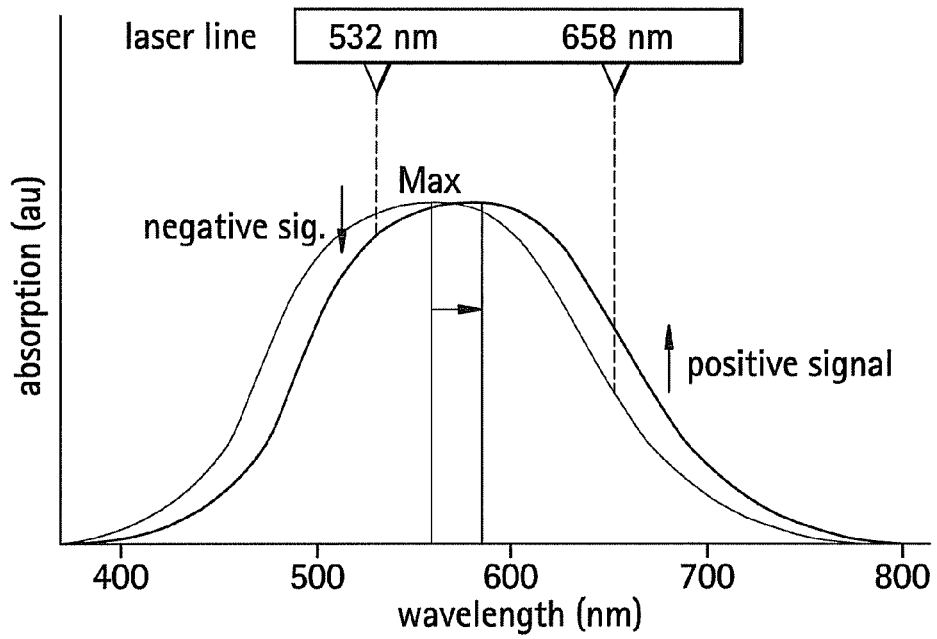
FIG. 8 relates to the electrochromism of the blue VSDs: (A) Simultaneous whole-cell and optical (JPW-3080) recordings of three action potentials (APs) evoked by somatic current injection. In this and following panels both optical traces (532 nm and 658 nm) were obtained in the same region of interest (ROI) selected on a basal dendrite 45-65 μm from the soma; (B) Same as in A except different VSD (PY-1266); (C) Same as in A except different VSD (JPW-4090); (D) Schematic representation of a spectral shift, which is thought to underlie voltage-sensitivity of fast dyes. Absorption spectrum for JPW-3080 at hyperpolarized (gray contour) and depolarized membrane potential (black contour). Upon depolarization the absorbance maximum (vertical gray line—max) shifts toward longer wavelengths. Gray arrow indicates the direction of the electrochromic shift. Excitation wavelengths shorter than the max (e.g., 532 nm) generate negative optical signals (downward pointing arrow). Excitation wavelengths longer than max (e.g., 658 nm) produce positive optical signals (upward pointing arrow); (E) Same as in D except the absorption maximum of JPW-4090 is below 532 nm; because both excitation lines (532 and 658 nm) are longer than max, both lines generate positive optical signals; spectra contours shown in D and E are not real data; they are shown here to illustrate the impact of voltage-induced spectral shift on the size and polarity of voltage-sensitive dye signals.

Results—Experiments in Acute Brain Slices:
Wavelength-Dependent Voltage Sensitivity Our first goal was to determine if newly synthesized molecules, when applied internally in mammalian neurons, produce any detectable voltage-dependent optical signals. Towards this goal, pyramidal cells were injected with blue dye JPW-3080. Following the incubation period, stained neurons were re-patched, and dye molecules were intermittently excited with two wavelengths. One laser excitation line (532 nm) was below the dye's absorption maximum (FIG. 8D, vertical gray line—max), and the other line (658 nm) was above the JPW-3080 absorption maximum. In all cells filled with JPW-3080 (n=4) laser excitation at 532 nm generated negative optical signals (FIG. 8A, middle trace), while excitation at 658 nm produced positive action potential-associated optical signals (bottom trace). The changes in signal size and signal polarity (FIG. 8A) can be understood as arising from a voltage-induced shift in the absorption spectra, represented schematically in FIG. 1DE. For example, at 532 nm excitation (FIG. 8D, vertical dashed line 532) depolarizing membrane potential transients produce a decrease in the intensity of the fluorescent light (negative signal). When the same neuron was illuminated by 658 nm laser line, membrane depolarization caused an increase in the intensity of the fluorescent light (8D, positive signal). Although showing an identical temporal dynamics, the two optical signals obtained from the same cell were otherwise very different, having opposite signs and very different signal amplitudes (FIG. 8A, optical traces 532 and 658 nm). The average amplitude of AP-associated optical signal obtained with 658 nm excitation was 4.13±0.96% ΔF/F (mean±s.d., n=4 cells, N=24 measurements). The average size of optical signal obtained from the same 4 cells but using a different laser wavelength (532 nm) was only 0.97±0.26% ΔF/F. Within the same cell and same region of interest, the average amplitude ratio of AP-associated signal at two wavelengths was 4.39±1.07 (n=4 cells, N=24 measurements). This discrepancy in signal size between two excitation wavelengths stems from the Gaussian contours of the dye's absorption (excitation) spectrum (V. Montana, D. L. Farkas, L. M. Loew, "Dual-wavelength ratiometric fluorescence measurements of membrane potential", Biochemistry, 28, 4536-4539 (1989)), and the exact position of the laser excitation line (FIG. 8D, dashed vertical line) in relation to absorption spectrum. For example, if excitation occurred in the linear segment of the Gaussian function (658 nm), voltage-evoked spectral shifts produced a relatively large change in absorption coefficient. If excitation occurred in the nonlinear (sigmoid) portion of the Gaussian function (532 nm), a spectral shift would produce small changes in absorption coefficient (small optical signals), because this segment of the function is partially saturated (very close to peak excitation). In general, for optimal ΔF/F it is best to excite the dyes at the wings of their excitation spectra in order to maximize ΔF and minimize F.

Figure 8E:
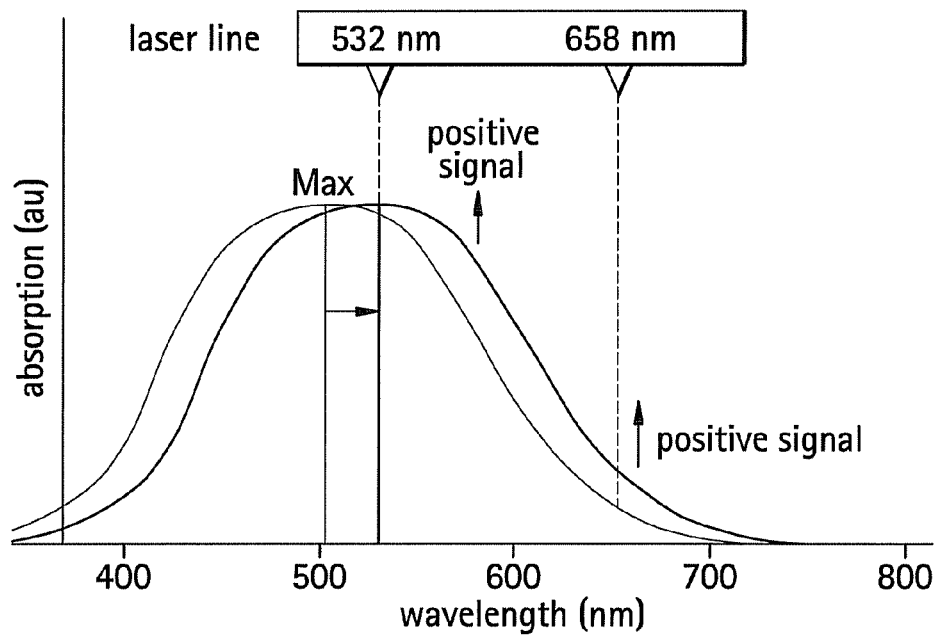

Out of seven new blue dyes, JPW-3080 was the only one that gave negative and positive signals at two excitation lines (532 nm and 658 nm). This is because the peak absorption of JPW-3080 lies in between these two available laser lines (FIG. 8D, vertical gray) while the others have excitation maxima in membranes that are either below or very near 532 nm. Blue dyes JPW-4090 and PY-1266, for example, gave positive signals at both 532 nm and 658 nm excitation (FIG. 8B, C). For JPW-4090, this is consistent with the fact that peak absorption wavelength is <532 nm (FIG. 8E, vertical gray line—max). Interestingly, spectral analysis of PY-1266 performed on multilamellar lipid vesicles (MLV) found peak excitation at 552 nm, respectively (Table 3), i.e., 20 nm higher than the 532 nm excitation wavelength used in our imaging experiments. For this reason, blue dye PY-1266 might have been expected to produce a negative signal at 532 nm, but this was not the case (FIG. 8B, middle trace). One possible explanation for this is that the spectrum of the dye on the dendrite membrane may be different than the spectrum in MLV, such that its true absorption maximum on the dendrite is below 532 nm. A second possibility is that the voltage-dependent shift of the excitation spectrum needs to be convoluted with a voltage dependent change in the emission spectrum; we did not characterize the voltage-dependent emission response, but certainly for other styryl dyes this can contribute as much or more than the change in excitation spectrum. E. Fluhler, V. G. Burnham, L. M. Loew, "Spectra, membrane binding, and potentiometric responses of new charge shift probes", *Biochemistry,* 24 5749-5755 (1985); A. Bullen, P. Saggau, "High-speed, random-access fluorescence microscopy: II. Fast quantitative measurements with voltage-sensitive dyes", *Biophysical Journal* 76, 2272-2287 (1999).

Taken together, these experiments established that blue naphtylstyryl dyes bound to the inner leaf of the neuronal plasmalemma exhibit voltage-sensitivity based on the spectral shift (FIG. 8D, E, gray arrow). The exact mechanism of the voltage-induced spectral shift was not systematically investigated. For Excitation in deep red (658 nm) produces several times larger optical signals than excitation with shorter wavelengths (532 nm).

that optical delay must be in the microsecond range. Based on the good temporal correlation between electrical and optical

TABLE 3

Evaluation of red and blue voltage-sensitive dyes intracellularly applied to cortical pyramidal neurons in brain slices

| Dye | Red | Blue | | | | | | |
|---|---|---|---|---|---|---|---|---|
| | JPW-3028 | JPW-3080 | JPW-6003 | JPW-4090 | PY-1261 | PY-1268 | PY-1286 | PY-1266 |
| n (cells) | 41 | 11 | 2 | 21 | 2 | 3 | 8 | 8 |
| N (dends.) | 155 | 26 | 3 | 54 | 7 | 6 | 19 | 23 |
| Diffusion rate, subjectively | Typical | Fast | Very slow | Typical | | Slow | Typical | Fast |
| Dye loading time (min) | 29.6 ± 3.7 | 26.8 ± 3.4 | NDA | 34.9 ± 11.1 | NDA | NDA | 52.3 ± 6.7 | 32.5 ± 7.8 |
| Incubation time (min) | 75.7 ± 19.5 | 54.0 ± 35.2 | NDA | 69.5 ± 37.8 | NDA | NDA | 83.3 ± 43.7 | 58.5 ± 13.4 |
| Simple filling time (min) | 33.3 ± 5.8 | 43.1 ± 4.5 | 46.5 ± 12.0[a] | 58.3 ± 12.2 | 32.5 ± 3.5 | 55.0 ± 8.2[a] | 50.0 ± 10.0 | 45.8 ± 8.2 |
| dF/F at 658 nm | NDA | 5.13 ± 1.20 | 1.23 ± 0.66 | 11.03 ± 2.24 | 7.91 ± 1.57 | 5.89 ± 3.41 | 7.64 ± 2.20 | 8.32 ± 2.13 |
| dF/F at 633 nm | {at 532 nm = 6.14 ± 1.67} | NDA | NDA | 12.70 ± 3.59 | NDA | NDA | 13.67 ± 2.89 | 10.41 ± 2.80 |
| S/N ratio at 658 nm | NDA | 6.20 ± 2.29 | 4.97 | 6.93 ± 1.88 | 5.38 ± 1.86 | 4.44 ± 0.75 | 5.13 ± 2.31 | 5.22 ± 1.32 |
| S/N ratio at 633 nm | {at 532 nm = 5.95 ± 2.16} | NDA | NDA | 5.48 ± 2.01 | NDA | NDA | 4.53 ± 0.95 | 4.77 ± 1.35 |

[a]Somatic ROI: "NDA" indicates no data available. PY-1266 was in the form of a gamma-cyclodextrin complex (Wuskell et al., 2006).

Results—Response Time

Figure 9A:
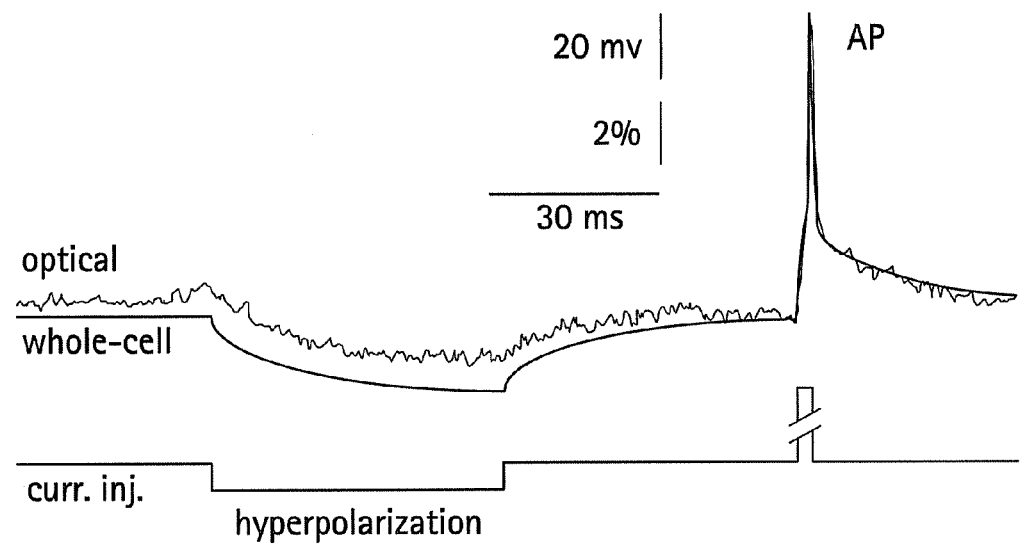
FIG. 9 relates to the fast response time of blue voltage-sensitive dyes: (A) Simultaneous whole-cell (black) and optical (gray) recordings of the evoked membrane potential changes using blue dye JPW-4090; optical signal was sampled from the basal dendrite 45 μm away from the cell body; average of 6 sweeps; (B) A segment of trace containing AP is blown up to show temporal correlation between whole-cell (black) and optical signal (gray); a distortion in electrical recording caused by poorly compensated series resistance (arrow) does not appear in the optical signal.

One of the most demanding tests for a calcium-sensitive, sodium-sensitive or voltage-sensitive dye is detection of a single action potential. See, for example, H. Marlram, P. J. Helm, B. Sakmann, "Dendritic calcium transients evoked by single back-propagating action potentials in rat neocortical pyramidal neurons", *Journal of Physiology*, 485, 1-20 (1995). This test is particularly strenuous in the case of voltage-sensitive dyes because here the optical signal is driven directly by the membrane potential change, which has very rapid rise and decay; typically in the range of 1 ms. The short duration of AP dramatically reduces the number of photons collected per time-point. In contrast, calcium-sensitive dye imaging of individual APs deals with much slower (and much larger) optical transients with durations typically in the range of 100 ms. H. Markram, P. J. Helm, B. Sakmann, "Dendritic calcium transients evoked by single back-propagating action potentials in rat neocortical pyramidal neurons", *Journal of Physiology*, 485, 1-20 (1995). Therefore, the response time of the voltage-sensitive dye is critical requirement for use in experimental measurements of individual action potentials. We tested how blue voltage-sensitive dyes change their fluorescent properties in response to membrane potential changes by recording simultaneously electrical (whole-cell) and optical (voltage imaging) signals from neuronal compartments very close to the cell body (less than 50 µm). In this portion of the dendritic tree we get the best signal-to-noise ratio (better than in the cell body), while the short distance from the cell body assures that the electrical signal is not distorted by dendritic cable properties" and/or voltage-gated ion channels. All of the newly synthesized blue dyes tested showed a very fast response to membrane potential change. The trajectories of optical signals (FIG. 9, gray) were excellent matches with whole-cell records (black). Both the slow components (FIG. 9, hyperpolarization) and fast transients (action potential, AP) of neuronal electrical activity were captured in the optical signal. We could not determine the exact time delay between optical and electrical signals, because our experimental setup is not designed to perform dual mode measurements with microsecond temporal resolution, but the fact that at 2.7 kHz sampling frequency we could not detect the discrepancy between AP electrical and optical signals, indicates transients (FIG. 2B) we conclude that newly synthesized blue dyes are properly suited for studying the dynamics of neuronal action potentials.

Figure 9B:
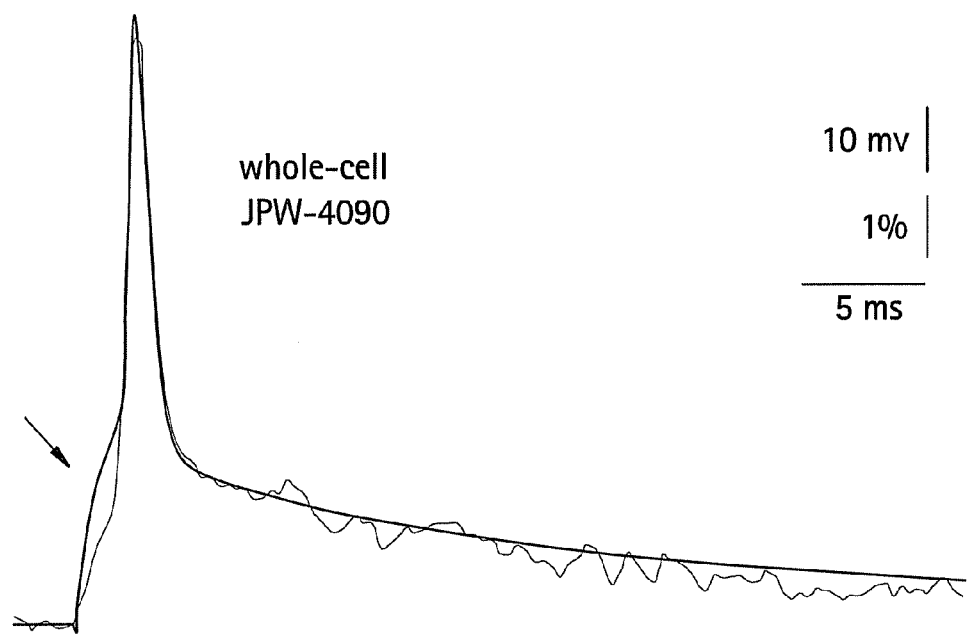

In addition, optical signals can be used to correct the distortions caused by poorly compensated glass electrode resistance. When series resistance is high, and difficult to compensate by bridge balance, the stimulus-induced voltage drop across the recording electrode contaminates biological signals (FIG. 9B, black trace, arrow). Optical signals, on the other hand, solely depend on electrical field across the biological membrane. Therefore, in the optical channel (FIG. 9B, gray trace) the membrane charging curve at the onset of a stimulus pulse is unaffected by electrode series resistance. L. B. Cohen, H. V. Davila, A. S. Waggoner, "Changes in axon fluorescence", *Biological Bulletin*, 141, 382-383 (1971); B. M. Salzberg, A. Grinvald, L. B. Cohen, H. V. Davila, W. N. Ross, "Optical recording of neuronal activity in an invertebrate central nervous system: simultaneous monitoring of several neurons", *Journal of Neurophysiology*, 40, 1281-1291 (1977). Note that electrical (black) and optical (red) traces have identical trajectories in all segments of the biological signal (AP) except at the stimulus onset (arrow). In this section, the electrical trace is contaminated by a recording artifact.

Results—Recording Action Potentials in Distal Dendritic Segments

The major expectation from internally applied voltage sensitive dyes is to detect action potentials in remote dendritic segments. S. D. Antic, "Action potentials in basal and oblique dendrites of rat neocortical pyramidal neurons", *Journal of Physiology*, 550, 35-50 (2003); M. Djurisic, S. Antic, W. R. Chen, D. Zecevic, "Voltage imaging from dendrites of mitral cells: EPSP attenuation and spike trigger zones", *J. Neurosci.* 24, 6703-6714 (2004). Three factors burden voltage-sensitive dye imaging in distal dendrites. First, the recording site is far away from the dye injection site (cell body). The concentration of the lipophilic dye falls off with distance from the injection site, thus remote dendrites are difficult to stain with voltage probes. Second, the recording site is a small cellular compartment, which produces few photons (low light level). The signal-to-noise ratio is proportional to the square root of the number of photons. M. Zochowski, M. Wachowiak, C. X.

Figure 10:
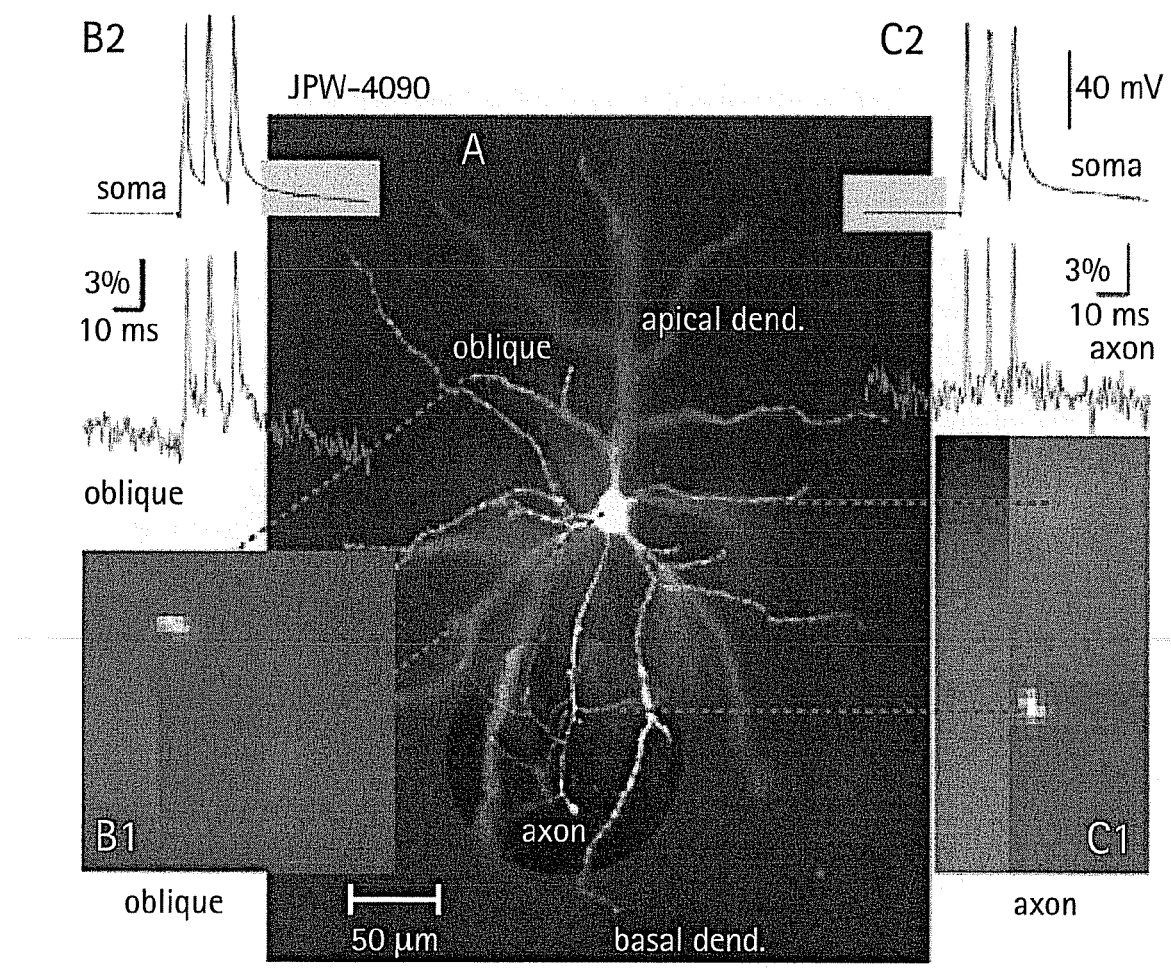
FIG. 10 relates to optical recordings of action potentials in dendrites and axons of pyramidal cells: (A) Microphotograph of a layer 5 pyramidal neuron filled with blue VSD JPW-4090; Region containing axon is shown with enhanced contrast; (B1) One movie frame captured by data acquisition camera at 2.7 kHz frame rate; Only the distal tip of the oblique branch is positioned inside the laser illumination spot; Dashed gray lines connect corresponding structure; (B2) Simultaneous whole-cell (black) and optical (gray) recording of an AP triplet; Optical signal was sampled from the oblique branch at distance of 128 μm from the soma; (C1) Same as in B1 except axon is being imaged; (C2) Optical signals (gray) were sampled from short axonal segment (~20 μm length) right at the first branch point (distance from soma=114 μm); Optical signal is product of 4 averaging.

Falk, L. B. Cohen, Y. W. Lam, S. Antic, D. Zecevic, "Imaging membrane potential with voltage-sensitive dyes", *Biological Bulletin*, 198, 1-21 (2000). Finally, it is difficult to record AP in distal dendritic tips, because the dendritic membrane is weakly excitable and does not support full action potential propagation. In the absence of full active regeneration, passive attenuation mechanisms tend to degrade the amplitude of the voltage transient in distal dendrites. Attenuation of action potential amplitude with distance from the soma is common in dendrites of pyramidal neurons. M. E. Larkum, J. J. Zhu, B. Sakmann, "Dendritic mechanisms underlying the coupling of the dendritic with the axonal action potential initiation zone of adult rat layer 5 pyramidal neurons", *Journal of Physiology*, 533, 447-466 (2001); B. M. Kampa, G. J. Stuart, "Calcium spikes in basal dendrites of layer 5 pyramidal neurons during action potential bursts", *J Neurosci.*, 26, 7424-7432 (2006). To detect backpropagating action potentials in distal dendritic segments, one needs to achieve thorough staining of the dendritic membrane. M. Zochowski, M. Wachowialc, C. X. Falk, L. B. Cohen, Y. W. Lam, S. Antic, D. Zecevic, "Imaging membrane potential with voltage-sensitive dyes", *Biological Bulletin*, 198, 1-21 (2000). Therefore, besides voltage-sensitivity, the speed with which voltage-sensitive dye diffuses through the intracellular space is perhaps the major feature to determine its usefulness in experiments. Upon intracellular injection, some blue dyes (4 out of 7) showed excellent spread into dendrites and axons (FIG. 10A). The staining of the plasma membrane was sufficient to allow optical recordings of individual action potentials from thin dendrites (FIG. 10B) and axons (FIG. 10C). We evaluated the intracellular spread of all newly synthesized blue dyes in respect to the most successful red dye JPW-3028. S. Antic, J. P. Wuskell, L. Loew, and D. Zecevic, "Functional profile of the giant metacerebral neuron of *Helix aspersa*: temporal and spatial dynamics of electrical activity in situ", *Journal of Physiology* 2000, 527, 55-69. Red dye JPW-3028 is water soluble molecule specially designed to travel fast through neuronal intracellular milieu. Blue dyes that appeared to travel with the same speed as the red dye we consider "typical"in present study (Table 3). Dyes that appeared to travel slower than the red dye (JPW-6003 and PY-1286) were characterized as "slow" in Table 3. Three out of 7 blue dyes appeared to fill neurons faster than red dye (JPW-3080, PY-1266, and PY-1261). We are aware that attributes such as "typical", "slow" and "fast" are qualitative (descriptive) and subjective, but it must be stated that this evaluation is based on "side-by-side" experiments/comparisons. In a given week (five experimental days) we would typically use 2-3 different voltage-sensitive dyes. Our laboratory records, on the other hand, contain quantitative information on exactly how much time was spent in each experiment on dye loading and dye incubation thereafter. In Table 2 we include only the subset of cells where good optical signals from basal dendrites (~150 μm from the soma) were obtained with less than 9 averages. Although duration of time (in minutes) is a quantitative measure, the problem with this approach is that both the dye loading and incubation sessions were stopped at experimenter's discretion. In order to provide a more objective measure of time required for dye spread in the dendritic tree, we designed the following experiment. Loading patch pipettes were filled with intracellular solution containing 400 μM dye concentration, and the dye loading pipette was kept on the cell at all times. Because no re-patching was undertaken this series of experiments was dubbed "Simple filling". In simple filling experiments 5 out of 7 blue dyes produced good optical signals (single AP) in less than 60 minutes after "break in". According to the time period spent for simple filling, some blue dyes (JPW-3080, PY-1261, PY-1266) were as fast as red dye JPW-3028, while others (JPW-1268, JPW-4090) were on average 15-20 minutes slower (Table 3).

Results—Voltage Sensitivity (ΔF/F)

All evaluations of signal amplitude (ΔF/F) were performed in basal dendrites 80-150 μm from the soma, using backpropagating action potential as a biological paradigm. Individual APs were triggered by short (1.5-2 ms) pulses of direct somatic current injection. Experimental measurements performed on 55 neurons stained with 7 voltage sensitive dyes showed that blue dyes JPW-4090, PY-1261, PY-1286 and PY-1266 had better sensitivity than red dye JPW-3028 (n=41). The fractional change ΔF/F (change in light intensity divided by the resting light intensity) obtained in present study using abovementioned blue dyes and laser illumination (633 nm) was in the range 10-13%. Compare this to 3-4% obtained in early experiments on basal dendrites using red dye and whole-field illumination with Xenon arc lamp (Antic, 2003).

Laser spot illumination effectively reduces background fluorescence. Background fluorescence no longer contributes to resting light intensity (F) and this is why laser experiments yield better ΔF/F than whole-field illumination technique. So, the comparison of laser-excited blue dye signal with arc lamp-excited red dye signal is somewhat unfair. In order to obtain a fair comparison we carried out a series of experiments in which red dyes were also spot-excited with laser light. When red dye JPW-3028 was excited with laser spot illumination (532 nm) the average ΔF/F from basal dendrites has risen to 6.14±1.67%; n=41 (Table 3). This ΔF/F was still smaller than average ΔF/F obtained with 4 blue dyes (JPW-4090, PY-1286, PY-1261 and PY-1266) excited with either 633 nm or 658 nm laser spot illumination (Table 3).

Figure 11A:
FIG. 11 is a comparison of signal amplitude and signal-to-noise ratio between blue (JPW-4090) and red (JPW-3028) voltage-sensitive dye: (A1) Whole-cell recording of a single AP. (A2) Simultaneous optical recording from the basal dendritic segment 100 μm away from the soma, using blue dye JPW-4090; (B1-B2) same as in A1-A2 except different neuron, different dye (red dye JPW-3028); Note that amplitude of the optical signal obtained with blue dye (A2) is approximately 3 times stronger than the one obtained with red dye (B2); Both signals are products of spatial averaging (3 pixels) and temporal averaging (4 sweeps); Panels A3 and B3 show two optical signals scaled to the same height. The signal-to-noise ratio in the blue dye recording is actually worse than in the red dye recording.
Figure 11B:
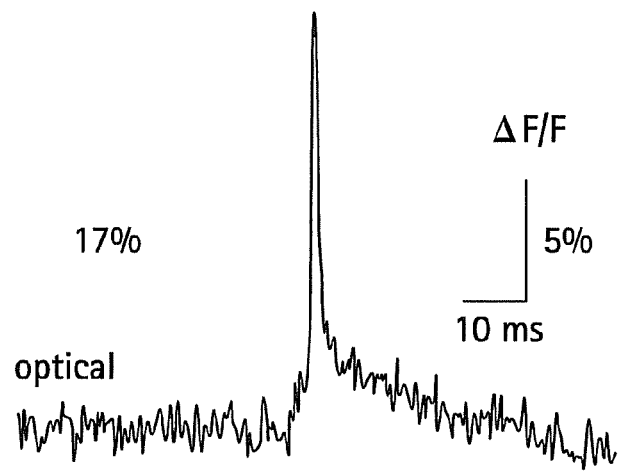
Figure 11C:
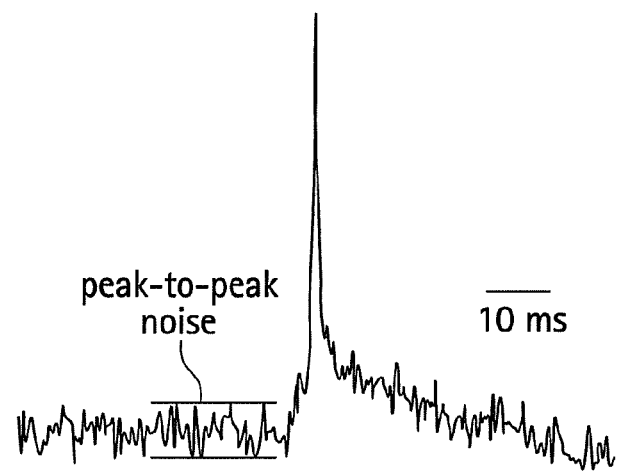
Figure 11D:
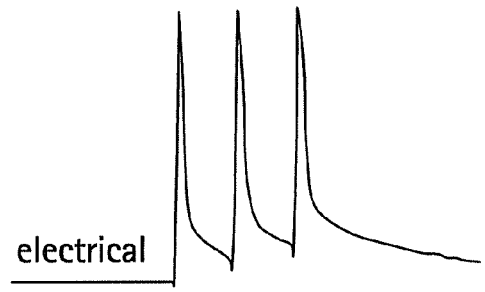
Figure 11E:
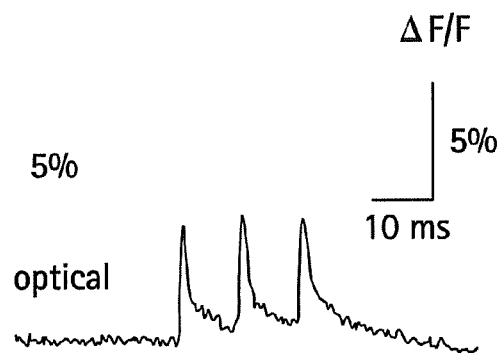
Figure 11F:
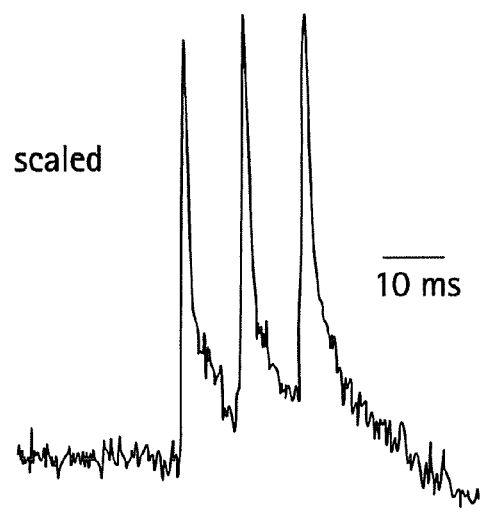

Better sensitivity of blue dyes (ΔF/F) does not necessarily translate into better signal-to-noise ratio. In the example shown in FIG. 11A, AP-associated optical signal captured with blue dye JPW-4090 in the basal dendrite (80 μm from the soma) measured 17% ΔF/F (base line-to-peak). In the basal dendrite of a different neuron filled with red dye JPW-3028, AP-associated optical signals measured only 5% ΔF/F (FIG. 11B2). Off line scaling of two signals (FIG. 4A3-B3) showed that in spite of the three-fold larger ΔF/F, blue-dye-signals still exhibited worse signal-to-noise ratio than red-dye-signals. For this reason, the average signal-to-noise ratios of the best blue dyes (6.93±1.88 for JPW-4090 and 5.13±2.31 for PY-1286; n=29) were not statistically better than the average S/N obtained in 41 neurons stained with red dye (Table 3).

Results—Light Scattering

Besides an increase in ΔF/F the laser excitation technique also improved the spatial resolution of our optical recordings. The spot laser illumination approach reduced the amount of light scattering in acute brain slice preparation. The previous experimental study (S. D. Antic, "Action potentials in basal and oblique dendrites of rat neocortical pyramidal neurons", *Journal of Physiology* 550, 35-50 (2003)) and present study were both performed on the same microscope, using identical optics and biological preparation. This allowed us to make direct comparisons. For example, in the experiments with red VSDs and whole-field illumination (S. D. Antic, "Action potentials in basal and oblique dendrites of rat neocortical pyramidal neurons", *Journal of Physiology* 550, 35-50 (2003)), the fluorescent light (and hence the optical signal) from one basal branch, was often scattered over 2-3 neighboring pixels. In present experiments the optical signal was only present at those pixels receiving direct fluorescent light from the region of interest (FIG. 12Aa, pixel 1). Pixels adjacent to the one receiving direct fluorescent light did not carry a detectable biological signal, due to a sharp fall in resting light intensity (FIG. 12B, pixels 2 and 3).

In addition to eliminating the smearing (scattering) of the optical signal, the laser spot illumination technique has proven excellent in eliminating the background fluorescence—fluorescent light emanating from areas out of focus and outside the region of interest (ROI). For instance, fluorescent objects of less than 20 μm away from the ROI were deliberately positioned outside the laser spot and therefore did not contribute any light to our ROI (FIG. 12A, lower). This was done by placing the edge of the illuminated spot (FIG. 12Ab, dashed circle) between the two bright objects (oblique and basal dendrite). This approach is very useful in regions of the dendritic tree with juxtaposed branches. In cortical layer 5 pyramidal cells, such regions are commonly found in the basilar and apical tuft dendritic arbors.

Results—Spatial and Temporal Averaging

In previous work (S. D. Antic, "Action potentials in basal and oblique dendrites of rat neocortical pyramidal neurons", *Journal of Physiology* 550, 35-50 (2003)), we typically averaged optical signals from 6-9 adjacent pixels (spatial averaging) in order to bring signal-to-noise ratio above 5 (red dye JPW-3028). Due to the sensitivity and brightness of the blue dyes, a signal-to-noise ratio greater than 5 was frequently obtained from a single pixel output (FIG. 12B, pixel 1) (n=13).

In terms of temporal averaging, the excellent sensitivity of blue dyes, naturally, reduced the demand for a large number of sweeps. In a recent study employing red voltage-sensitive dye (JPW-3028), in order to achieve reasonable signal-to-noise ratios from axons of cortical pyramidal cells, the authors had to average up to 200 sweeps (L. M. Palmer, G. J. Stuart, "Site of action potential initiation in layer 5 pyramidal neurons", J. Neurosci., 26, 1854-1863 (2006)). Extensive averaging is necessary when the voltage-dependent optical signal is very small and buried in the high-frequency noise. In studies of action potential initiation and propagation, extensive averaging carries several potential problems. First, the small jitter in the timing of AP and changes in AP shape from trial to trial produce an averaged result that is somewhat distorted in the time domain. Second, the fact that the signal is buried in noise precludes on line monitoring and detection of AP failures from trial to trial. The inclusion of failed and partially failed APs in the averaged result introduces distortions in amplitude and shape of the signal. Finally, repeated illumination of the same cellular compartment may cause photodynamic damage and severely impair the membrane physiology (S. Antic, G. Major, D. Zecevic, "Fast optical recordings of membrane potential changes from dendrites of pyramidal neurons", Journal of Neurophysiology, 82, 1615-1621 (1999)).

Figure 13C:
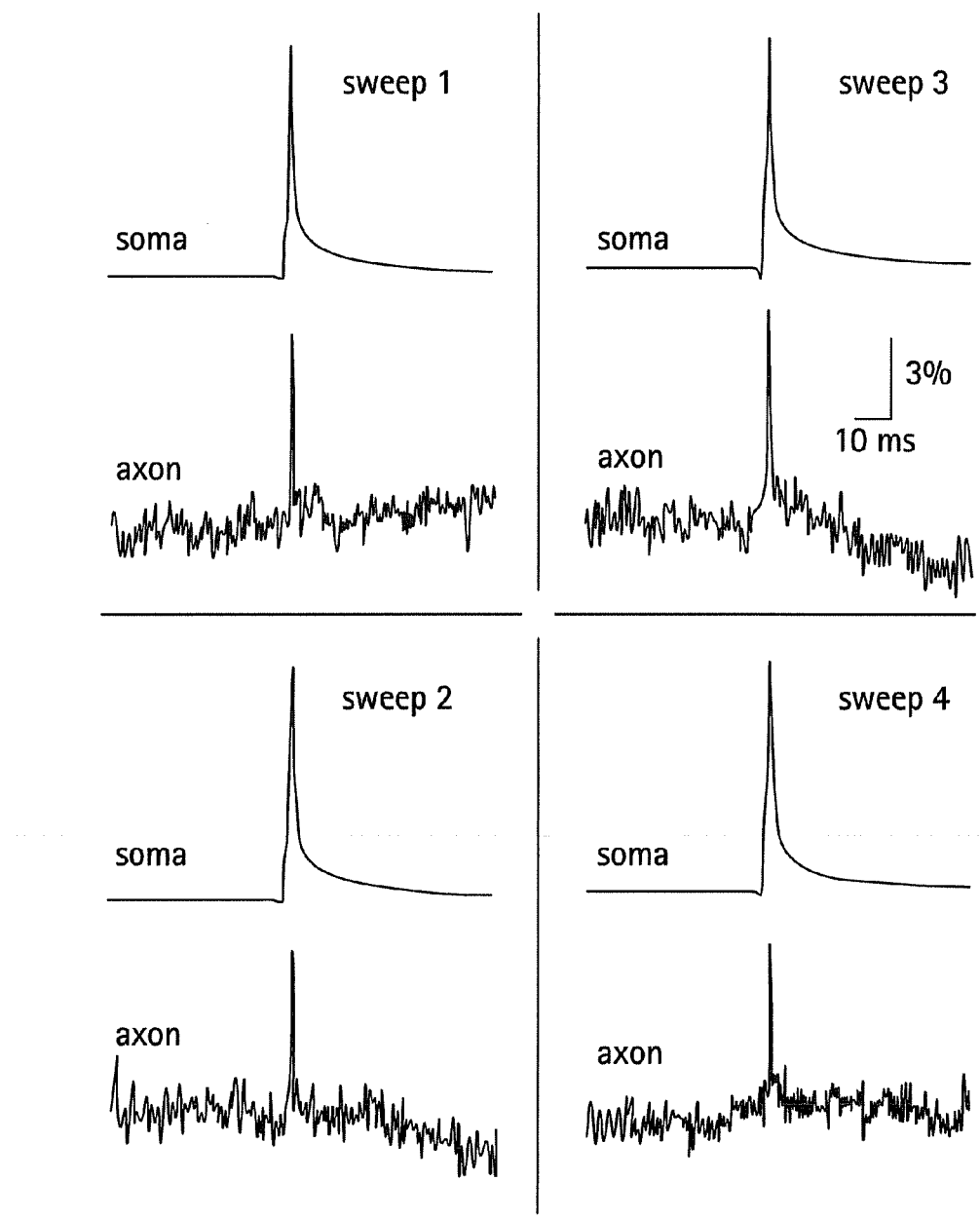
FIG. 13 relates to temporal averaging with blue VSDs: Excellent sensitivity of blue VSDs, combined with laser spot illumination approach, diminishes the need for extensive temporal averaging; (A) A single action potential was recorded in axonal segment 185 μm away from the cell body using only 9 averages; (B) Closer to the cell body (85 μm) only 6 sweeps were needed to produce signal-to-noise ratio>10; (C) Four out of 6 individual sweeps used to generate optical signal shown in B. Note that axonal AP can be detected in single sweep measurements (sweeps 1-4).

Blue voltage sensitive dyes greatly diminished our dependence on temporal averaging. In the present study we needed ~9 averages to record individual action potentials in axonal segments 200 μm away from the cell body, and achieve a signal-to-noise ratio around 10 (FIG. 13A) (n=12). In axonal regions at less than 100 μm away from the cell body excellent signal-to-noise ratios (~10) were regularly attained in less than 6 sweeps (FIG. 13B). Most importantly, blue voltage-sensitive dyes allowed us to reliably detect AP signal in single trial measurements (FIG. 13C, sweep 1-4). In summary, our new experimental design based on blue VSDs allows on-line monitoring of the success rate of AP invasion in trial-to-trial mode.

Results—Toxicity

Figure 14A:
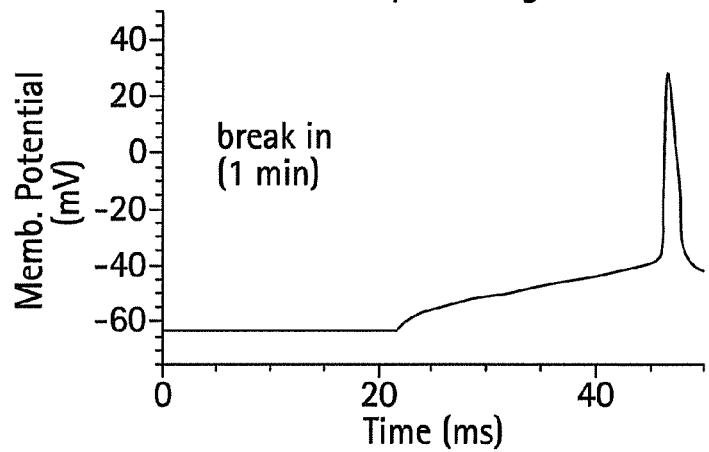
FIG. 14 relates to monitoring AP dynamics during the course of experiment: (A-F) Direct current injection (120 pA, 50 ms, standard pulse) was used to trigger somatic AP in different phases of the voltage-imaging experiment; Insets (D-F): simultaneous somatic (whole-cell) and dendrite or axonal (VSD) recording of current-evoked single AP; (G) Plot of AP half-width versus time during the entire course of experiment; APs were probed by standard current pulse during the dye injection phase (Dye loading) and during voltage-imaging (Optical recording session); Patch pipette was not on the cell during incubation.
Figure 14B:
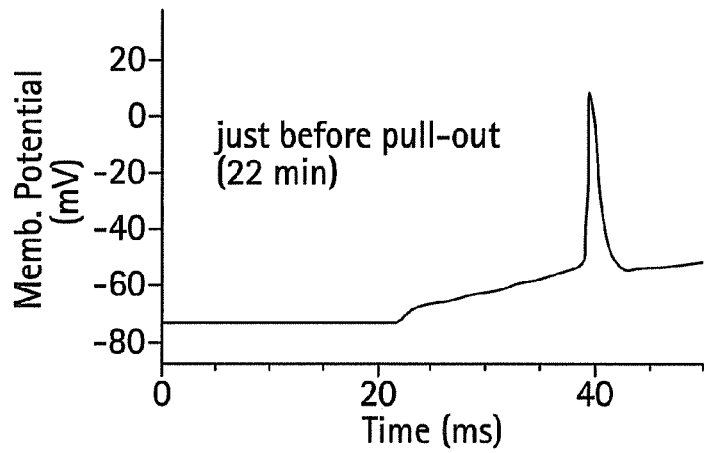
Figure 14C:
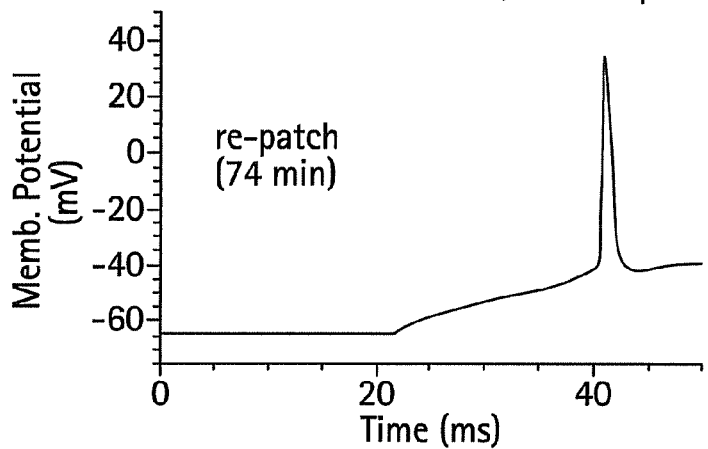
Figure 14D:
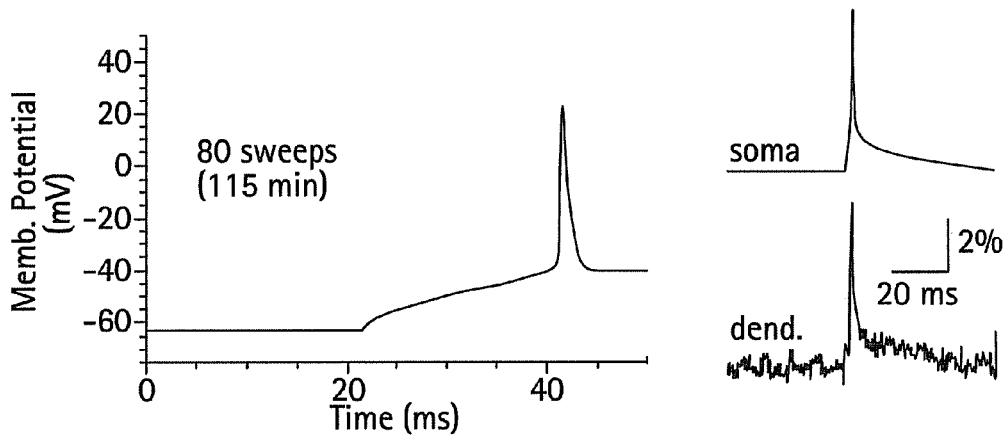
Figure 14E:
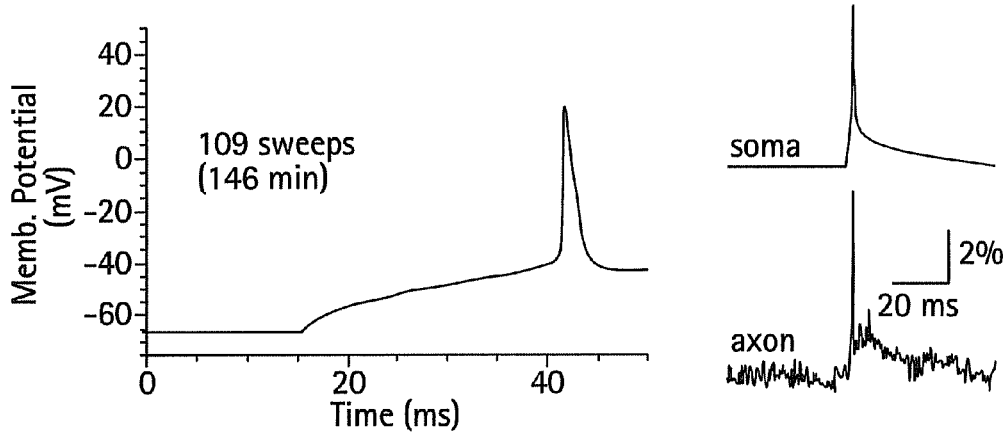
Figure 14F:
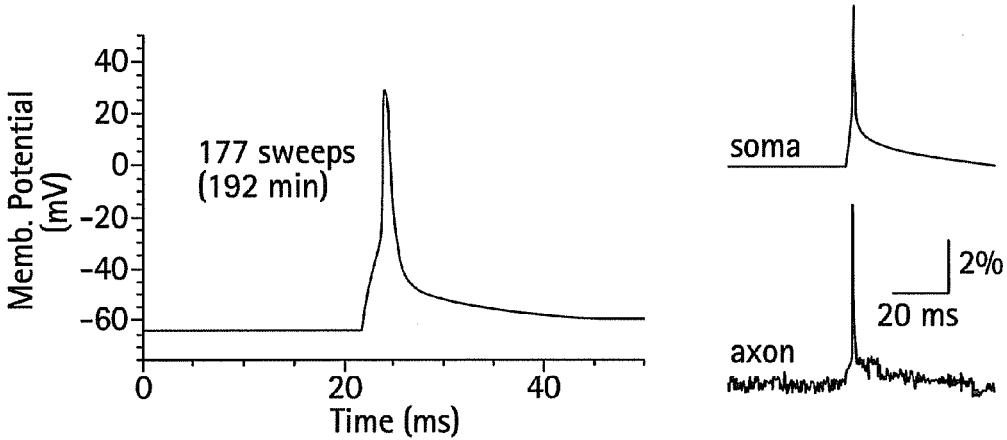
Figure 14G:
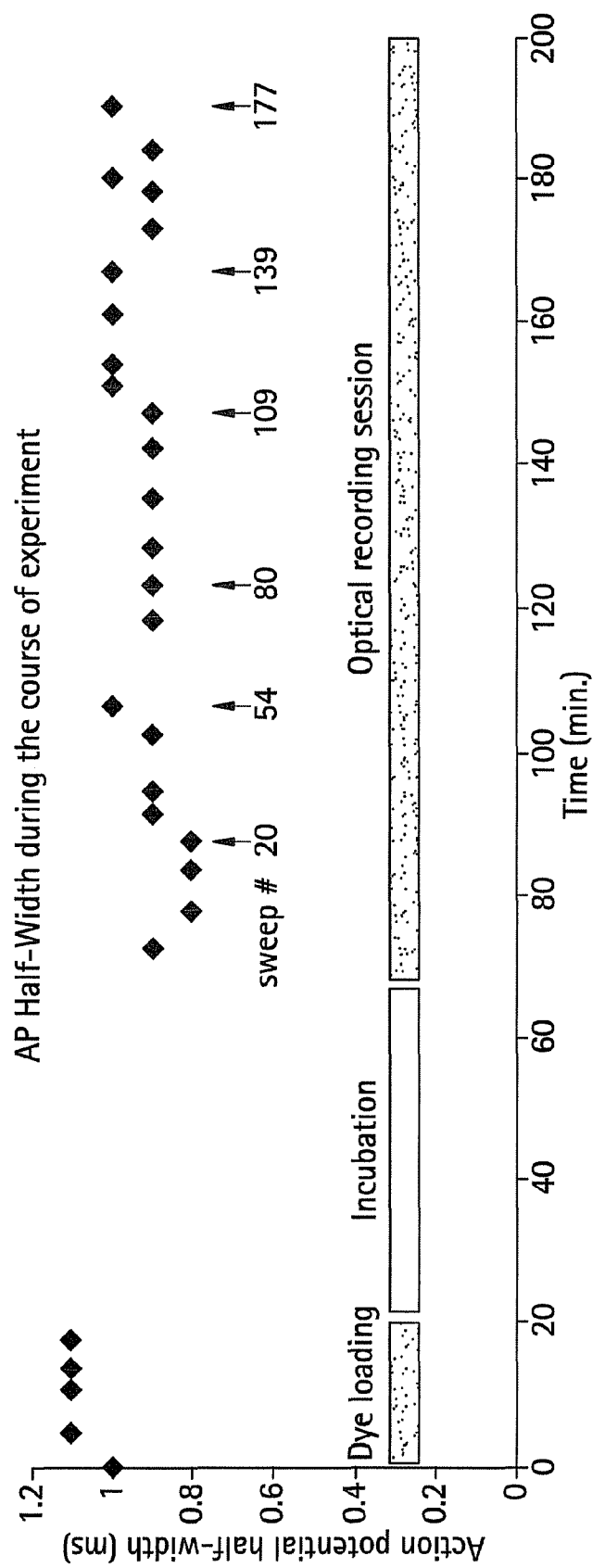
Figure 15A:
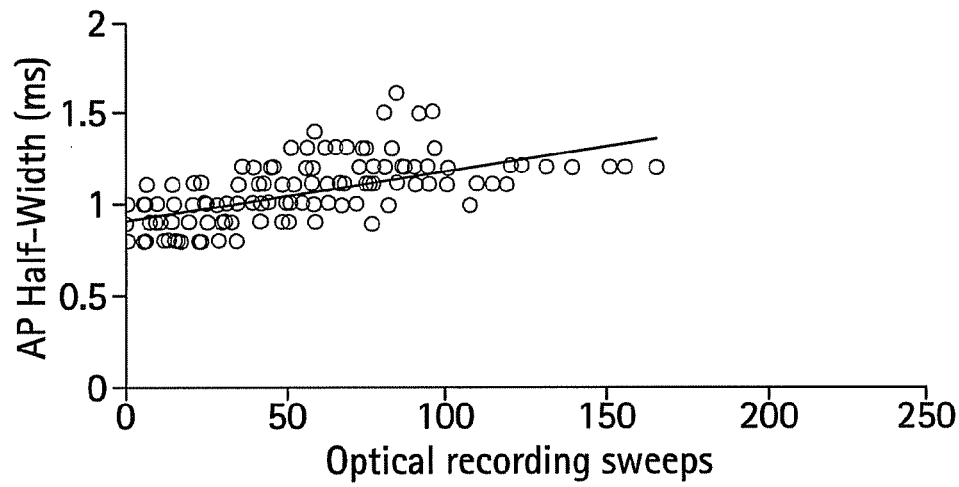
FIG. 15 relates to change of AP half-width during the optical recording session: (A) AP half-width is plotted versus the number of cumulative optical recording sweeps; Sweep duration=100 ms. Intracellularly applied red VS dye JPW-3028 was used for dendritic voltage imaging. Group data from 12 neurons; (B) Same data as in A; Instead of cumulative sweeps, time from re-patch (0 min) was used in X-axis; (C-D) Same as in A and B—but different intracellular dye (JPW-4090); Group data from 12 neurons; Black lines represent linear fits.
Figure 15B:
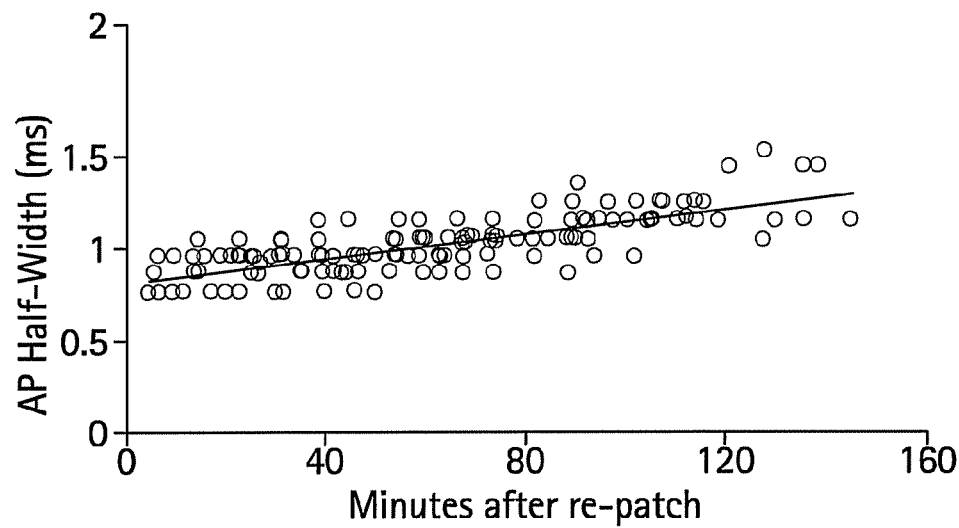
Figure 15C:
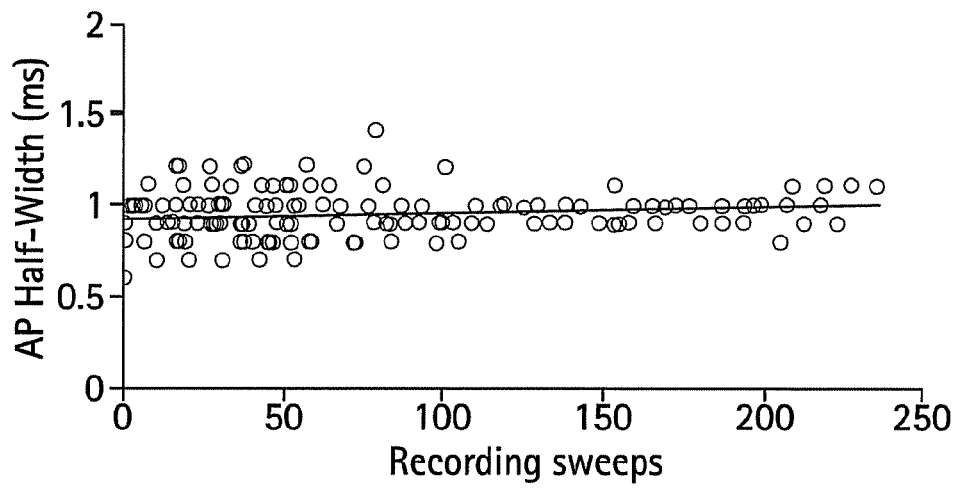
Figure 15D:
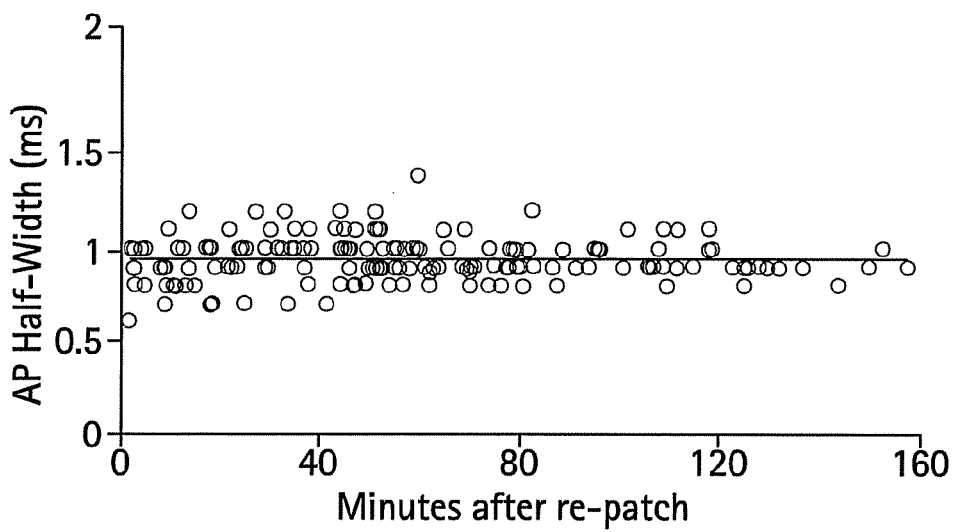
Figure 16:
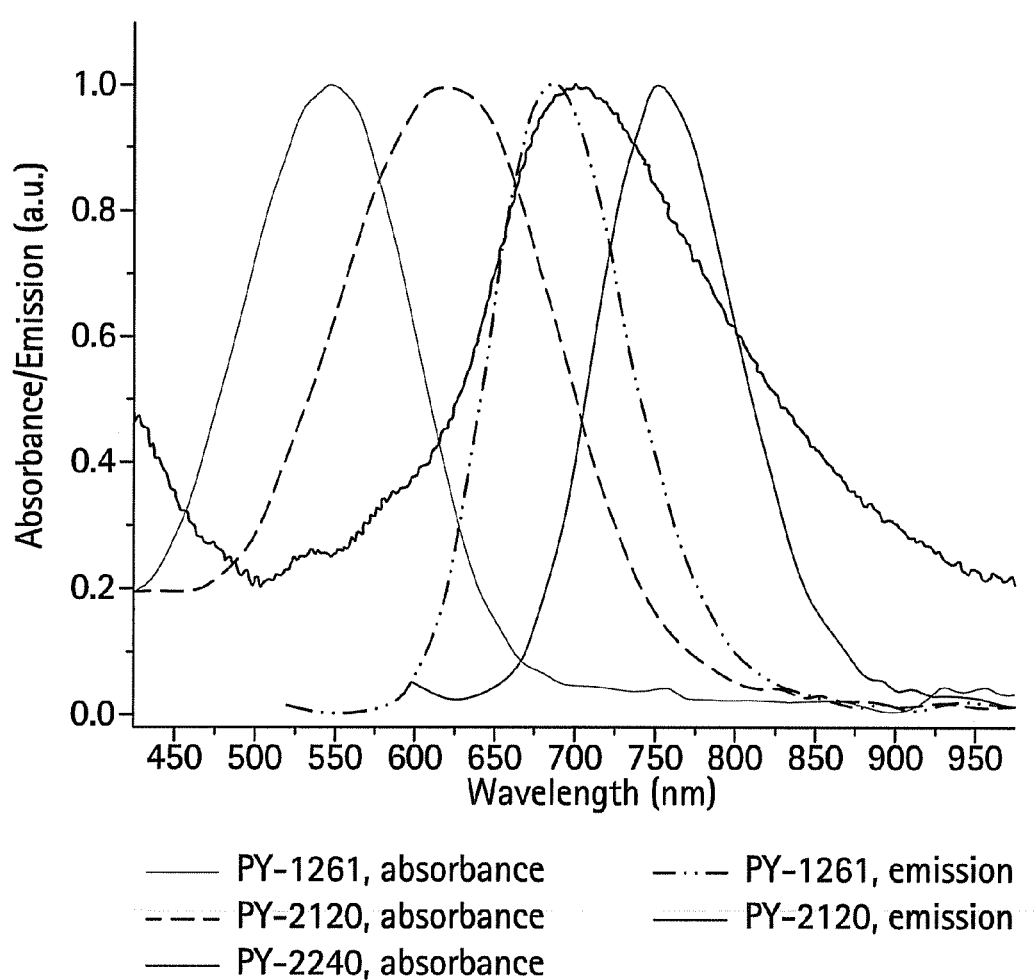
FIG. 16 consists of emission spectra of PY-1284 and PY-1261 in vesicle suspensions prepared from 1,2-dioleoyl-sn-glycero-3-phosphocholine (DOPC) or 7:3 DPPC/cholesterol in PBS buffer; lipid concentration=0.017 mg/mL.

Toxic effects of red voltage sensitive dyes (JPW-1114 and JPW-3028) are manifested by an increase in AP duration. S. Antic, G. Major, D. Zecevic, "Fast optical recordings of membrane potential changes from dendrites of pyramidal neurons", Journal of Neurophysiology, 82, 1615-1621 (1999). Accumulation of reactive oxygen species (free radicals), which interact with and damage neuronal plasmalemma, is the most likely mechanism. J. B. Feix, B. Kalyanaraman, "Production of singlet oxygen-derived hydroxyl radical adducts during merocyanine-540-mediated photosensitization: analysis by ESR-spin trapping and HPLC with electrochemical detection", *Archives of Biochemistry & Biophysics*, volume 291, pages 43-51 (1991). High intensity illumination during optical recording sessions excites large number of membrane bound dye molecules. Since styryl dyes have tendency to penetrate deep into the lipid bilayers (E. Fluhler, V. G. Burnham, L. M. Loew, "Spectra, membrane binding, and potentiometric responses of new charge shift probes", Biochemistry, 24, 5749-5755 (1985)), free radicals are produced literally inside the neuronal membrane. In the previous work it was difficult to obtain more than 25 illumination (recording) sweeps (100 ms each) from one neuron, before AP showed increase in half-width. S. D. Antic, "Action potentials in basal and oblique dendrites of rat neocortical pyramidal neurons", *Journal of Physiology* 550, 35-50 (2003). In present study, the number of optical recording sessions (100 ms each) surpassed the old result by a factor of 4. For example, in 8 neurons stained with blue dye JPW-4090 the number of optical recording sweeps exceeded 100 without causing any change in AP half-width (FIG. 14G, FIG. 8C). During 100 minutes-long optical recording sessions (FIG. 15D), we lost more neurons due to bad access resistance or mechanical drift of the patch pipette, than to photodynamic damage induced by blue VSDs. Since dye loading was always done at room temperature (21° C.) and re-patching at 34° C., we could not compare AP shape and size before and after dye loading. Therefore, in order to check the extent of dye toxicity we designed a group of experiments in which neurons were injected and incubated at 34° C. During the dye injection (loading phase), in regular time intervals (3-5 min) direct current pulses was used to slowly charge the membrane and trigger an AP (FIG. 14A). Identical current pulse was then applied at the end of dye loading phase, just before the electrode pull-out (FIG. 14B) and after the 50-90 min incubation period (FIG. 14C, re-patch). Optical recordings were performed on basal dendrites and axons in a standard protocol (typically, a total of 5-6 regions, 3 to 25—sweeps averaging per region). To avoid AP jitter in optical recordings we used shorter and stronger current pulses (FIG. 14D, E, F, insets). However, from time to time we returned to AP-testing current injection protocol (FIG. 14D, E), while keeping the count on the number of cumulative high-intensity light exposures (# sweeps). The plot of AP half-width versus the entire course of the experiment (time), including the dye loading phase, and measurement performed in the first minute after the "break in" (point 0 min), shows that blue dye JPW-4090, did not induce any AP broadening up to 177 optical sweeps, or 192 minutes since the beginning of the dye injection (FIG. 14G). All of the blue dyes (Table 1) seem to exert minimal toxic effects on AP duration. As in the case of JPW-4090, recording sessions more often ended due to problems with whole-cell recordings, than with photodynamic damage; yielding on average 114±67 (mean±s.d.; n=12) sweeps. In experiments using red VSD dye JPW-3028 we managed to record 86±28 sweeps before the AP half-width grew by more than 15% from the control value (n=12). The slope of the linear fit for JPW-3028 (FIG. 15A, black line; y=0.0027) was notably larger than the one obtained with JPW-4090 (FIG. 15C; y=0.0003). These data show that under current experimental conditions blue VSDs exerted less photodynamic damage than red VSDs. Additional experimental details can be found in Ping Yan, Aifang Xie, Meide Wei, and Leslie M. Loew, "Amino(oligo)thiophene-Based Environmentally Sensitive Biomembrane Chromophores", *Journal of Organic Chemistry*, published on web Jul. 30, 2008.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

All ranges disclosed herein are inclusive of the endpoints, and the endpoints are independently combinable with each other.

The use of the terms "a" and "an" and "the" and similar referents in the context of describing the invention (especially in the context of the following claims) are to be construed to cover both the singular and the plural, unless otherwise indicated herein or clearly contradicted by context. Further, it should further be noted that the terms "first," "second," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity).

The invention claimed is:

1. An amino (oligo) thiophene dye having the structure

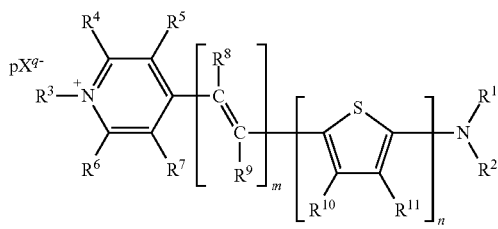

wherein m is 1, 2, 3, or 4; n is 2, 3, 4, 5, or 6; $R^1$ and $R^2$ are each independently hydrogen or optionally substituted $C_1$-$C_{10}$ alkyl, $C_3$-$C_7$ cycloalkyl, or phenyl; $R^3$ is optionally substituted $C_1$-$C_{10}$ alkyl; $R^4$, $R^5$, $R^6$, and $R^7$ are each independently hydrogen or fluorine; or $R^4$ and $R^5$ collectively form a fused aromatic ring, and/or $R^6$ and $R^7$ collectively form a fused aromatic ring; each occurrence of $R^8$, $R^9$, $R^{10}$, and $R^{11}$ is independently hydrogen or halogen, or $R^{10}$ and $R^{11}$ collectively form ethylenedioxy (—OCH$_2$CH$_2$O—); provided that at least two adjacent thiophene groups can, optionally, be linked via a fused ring to form a dithiophene unit having the structure

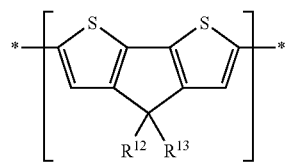

wherein $R^{12}$ and $R^{13}$ are each independently hydrogen or optionally substituted $C_1$-$C_6$ alkyl; $X^{q-}$ is an anionic counterion wherein q is 1 or 2 or 3; and p is 0, 1, 2, 3, or 4.

2. The amino (oligo) thiophene dye of claim 1, wherein m is 1.

3. The amino (oligo) thiophene dye of claim 1, wherein n is 2 or 3.

4. The amino (oligo) thiophene dye of claim 1, wherein $R^1$ and $R^2$ are each independently $C_1$-$C_4$ alkyl or $C_1$-$C_4$ perfluoroalkyl.

5. The amino (oligo) thiophene dye of claim 1, wherein $R^3$ is quaternary ammonium-substituted $C_1$-$C_{10}$ alkyl or quaternary ammonium-substituted $C_1$-$C_{10}$ perfluoroalkyl.

6. The amino (oligo) thiophene dye of claim 1, wherein $R^3$ is sulfonate-substituted $C_1$-$C_{10}$ alkyl or sulfonate-substituted $C_1$-$C_{10}$ perfluoroalkyl.

7. The amino (oligo) thiophene dye of claim 1, wherein at least one of $R^8$ and $R^9$ is fluorine.

8. The amino (oligo) thiophene dye of claim 1, wherein $X^{q-}$ is selected from the group consisting of hydroxide, fluoride, chloride, bromide, and iodide, sulfite, sulfate, acetate, trifluoroacetate, propionate, succinate, glycolate, stearate, lactate, malate, tartrate, citrate, ascorbate, pamoate, maleate, hydroxymaleate, phenylacetate, glutamate, benzoate, salicylate, sulfanilate, 2-acetoxybenzoate, fumarate, toluenesulfonate, methanesulfonate, ethanesulfonate, ethane disulfonate, benzenesulfonate, toluenesulfonate, oxalate, malonate, succinate, glutarate, adipate, and isethionate.

9. The amino (oligo) thiophene dye of claim 1, wherein $X^{q-}$ is bromide.

10. The amino (oligo) thiophene dye of claim 1, exhibiting optical properties that are sensitive to its molecular environment.

11. The amino (oligo) thiophene dye of claim 10, wherein the optical environmental sensitivity is a second harmonic generation environmental sensitivity of at least 3 percent per 50 millivolts when stimulated with a 1064 nanometer femtosecond fiber laser.

12. The amino (oligo) thiophene dye of claim 10, wherein the optical environmental sensitivity is a two photon fluorescence environmental sensitivity of at least 3 percent per 50 millivolts at 615-665 nanometers.

13. An amino (oligo) thiophene dye having the structure

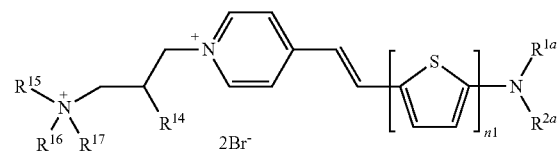

wherein $R^{1a}$ and $R^{2a}$ are each independently $C_1$-$C_6$ alkyl; $R^{14}$ is hydrogen or hydroxy; $R^{15}$, $R^{16}$, and $R^{17}$ are each independently methyl, ethyl, or 2-hydroxyethyl; and n1 is 2, or 3.

14. An amino (oligo-)thiophene dye having a structure selected from the group consisting of
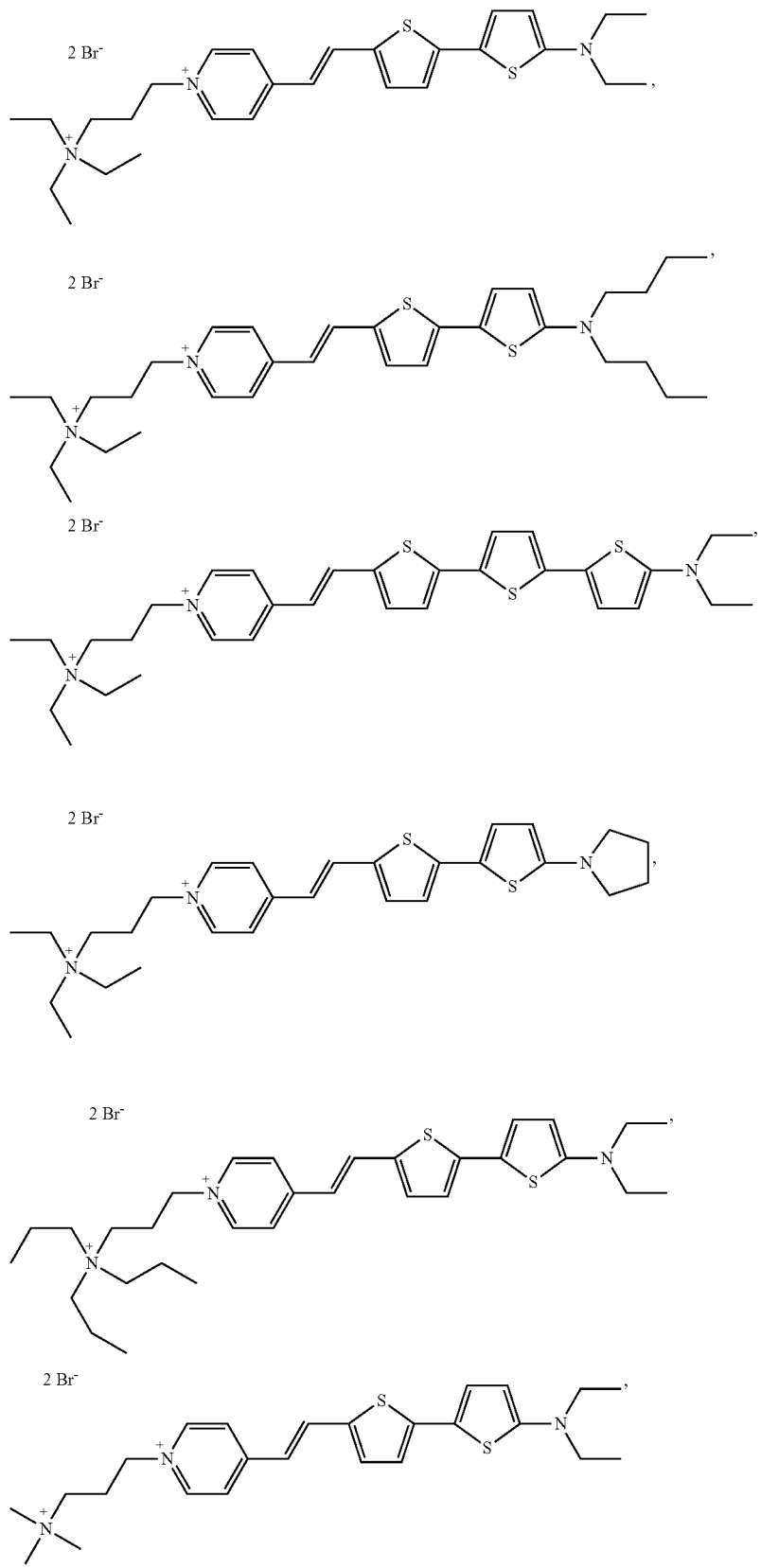

-continued
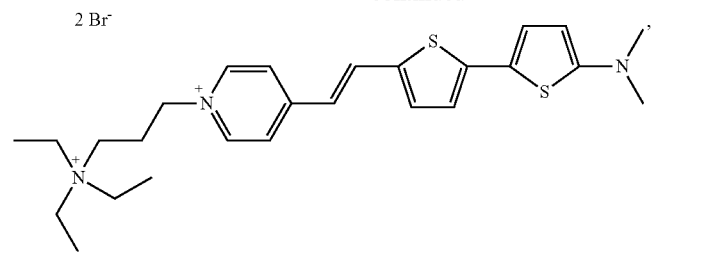
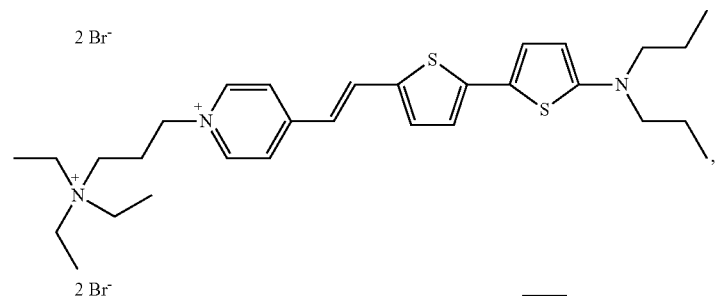
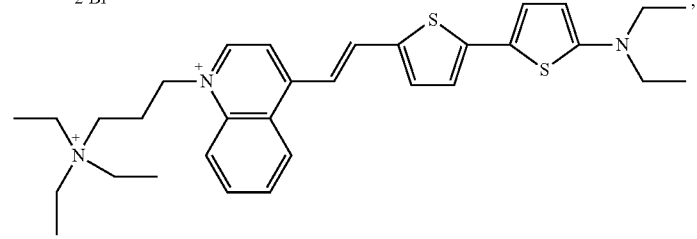
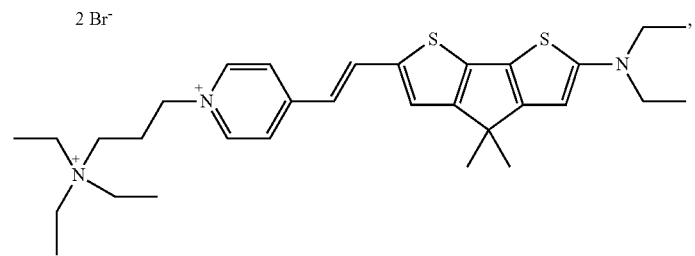
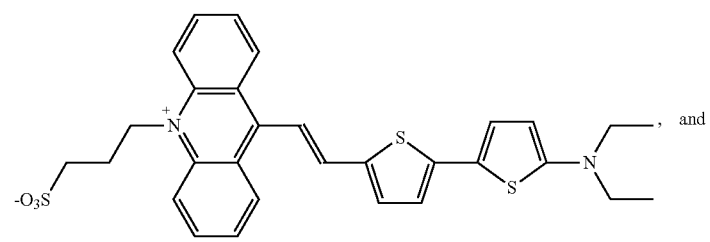, and
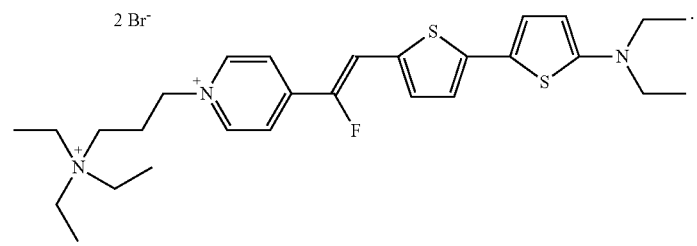.

15. A method of preparing an amino-(oligo-)-thiophene dye, comprising:

reacting an amine with a bromine-substituted -(oligo-)-thiophene to form an amino-substituted -(oligo-)-thiophene; and reacting the amino-substituted -(oligo-)-thiophene with a 4-methyl-N-alkyl-pyridinium salt to form the amino -(oligo-)-thiophene dye;

wherein the amine has the structure $HN(R^1)(R^2)$, wherein $R^1$ and $R^2$ are each independently hydrogen or optionally substituted $C_1$-$C_{10}$ alkyl, $C_3$-$C_7$ cycloalkyl, or phenyl;

wherein the bromine-substituted oligo thiophene has the structure

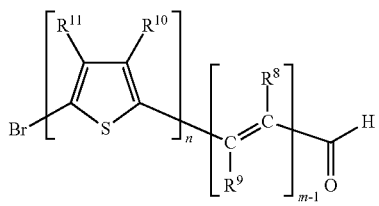

wherein m is 1, 2, 3, or 4; n is 2, 3, 4, 5, or 6; each occurrence of $R^8$, $R^9$, $R^{10}$, and $R^{11}$ is independently hydrogen or halogen, or $R^{10}$ and $R^{11}$ collectively form ethylenedioxy (—OCH$_2$CH$_2$O—), provided that at least two adjacent thiophene groups can, optionally, be linked via a fused ring to form a dithiophene unit having the structure

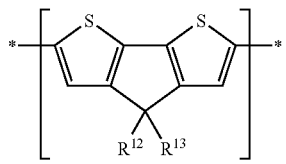

wherein $R^{12}$ and $R^{13}$ are each independently hydrogen or optionally substituted $C_1$-$C_6$ alkyl;

wherein the amino-substituted oligo thiophene has the structure

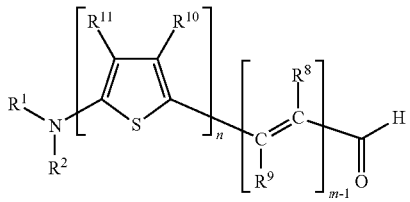

wherein $R^1$, $R^2$, $R^8$, $R^9$, $R^{10}$, $R^{11}$, m, and n are as defined above; and wherein the 4-methyl-N-alkyl-pyridinium salt has the structure

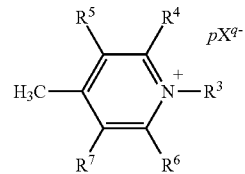

wherein $R^3$ is optionally substituted $C_1$-$C_{10}$ alkyl; $R^4$, $R^5$, $R^6$, and $R^7$ are each independently hydrogen or fluorine; or $R^4$ and $R^5$ collectively form a fused aromatic ring, and/or $R^6$ and $R^7$ collectively form a fused aromatic ring; $X^{q-}$ is an anionic counterion wherein q is 1 or 2 or 3; and p is 0, 1, 2, 3, or 4; and wherein the amino -(oligo-)-thiophene dye has the structure

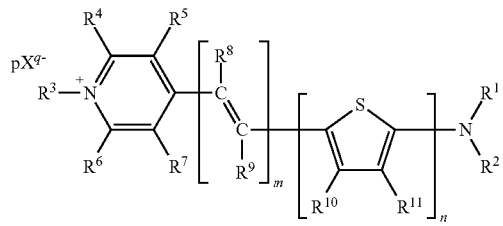

wherein $R^1$-$R^{11}$, X, m, n, p, and q are as defined above.

16. A biosensor comprising an amino -(oligo-)-thiophene dye of claim 1 and, optionally, further comprising a conjugate of a protein and an amino -(oligo-)-thiophene dye of claim 1; wherein the protein of the conjugate is covalently linked to the amino -(oligo-)-thiophene dye.

* * * * *